(12) United States Patent
Chen et al.

(10) Patent No.: US 9,133,218 B2
(45) Date of Patent: Sep. 15, 2015

(54) PESTICIDALLY ACTIVE PYRIDYL- AND PYRIMIDYL-SUBSTITUTED THIAZOLE DERIVATIVES

(71) Applicant: Syngenta Participations AG, Basel (CH)

(72) Inventors: Ruifang Chen, Shanghai (CN); Laura Quaranta, Stein (CH); Andrew Edmunds, Stein (CH); Andre Jeanguenat, Stein (CH); Aurelien Bigot, Stein (CH); Sebastian Rendler, Stein (CH); Roger Graham Hall, Stein (CH); Long Lu, Shanghai (CN); Peter Renold, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/405,568

(22) PCT Filed: Jun. 4, 2013

(86) PCT No.: PCT/CN2013/000668
§ 371 (c)(1),
(2) Date: Dec. 4, 2014

(87) PCT Pub. No.: WO2013/181931
PCT Pub. Date: Dec. 12, 2013

(65) Prior Publication Data
US 2015/0141423 A1 May 21, 2015

(30) Foreign Application Priority Data
Jun. 7, 2012 (EP) ..................................... 12171127

(51) Int. Cl.
| | | |
|---|---|---|
| C07D 417/14 | (2006.01) |
| C07D 513/04 | (2006.01) |
| C07D 491/052 | (2006.01) |
| A01N 43/78 | (2006.01) |
| A01N 43/90 | (2006.01) |
| C07D 471/04 | (2006.01) |
| A01N 43/84 | (2006.01) |
| C07D 498/04 | (2006.01) |
| A01N 47/24 | (2006.01) |
| A01N 51/00 | (2006.01) |

(52) U.S. Cl.
CPC .............. *C07D 513/04* (2013.01); *A01N 43/78* (2013.01); *A01N 43/84* (2013.01); *A01N 43/90* (2013.01); *A01N 47/24* (2013.01); *A01N 51/00* (2013.01); *C07D 417/14* (2013.01); *C07D 471/04* (2013.01); *C07D 491/052* (2013.01); *C07D 498/04* (2013.01)

(58) Field of Classification Search
CPC . C07D 417/14; C07D 513/04; C07D 491/052
USPC ............... 546/114, 115, 117, 118; 514/235.2, 514/301, 302, 303
See application file for complete search history.

(56) References Cited

U.S. PATENT DOCUMENTS

| | | | |
|---|---|---|---|
| 8,809,547 B2 * | 8/2014 | Bretschneider et al. ...... | 548/202 |
| 2011/0098287 A1 | 4/2011 | Bretschneider et al. | |
| 2011/0212949 A1 | 9/2011 | Bretschneider et al. | |

OTHER PUBLICATIONS

International Search Report for International Patent Application No. PCT/CN2013/000668 dated Sep. 12, 2013.

* cited by examiner

*Primary Examiner* — Niloofar Rahmani
(74) *Attorney, Agent, or Firm* — R. Kody Jones

(57) ABSTRACT

Disclosed are pesticidally active pyridyl- and pyrimidyl-substituted thiazole derivatives, processes for their preparation, compositions comprising those compounds, and their use for controlling insects.

13 Claims, No Drawings

PESTICIDALLY ACTIVE PYRIDYL- AND PYRIMIDYL-SUBSTITUTED THIAZOLE DERIVATIVES

RELATED APPLICATION INFORMATION

This application is a 371 of International Application No. PCT/CN2013/000668, filed 4 Jun. 2013, which claims priority to EP Patent Application No. 12171127.9, filed 7 Jun. 2012, the contents of which are incorporated herein by reference herein.

The present invention relates to insecticidally active pyridyl- and pyrimidyl-substituted thiazole derivatives to processes for their preparation, to compositions comprising those compounds, and to their use for controlling insects or representatives of the order Acarina.

2-(3-Pyridyl)-thiazole derivatives with pesticidal action are known and described, for example, in U.S. Pat. No. 4,080,457, WO 2009/149858, WO 2010/129497, WO 2010/006713, WO 2011/138285 and WO 2012/000896.

There have now been found novel pyridyl- and pyrimidyl-substituted thiazole derivatives with pesticidal properties.

The present invention accordingly relates to compounds of formula I,

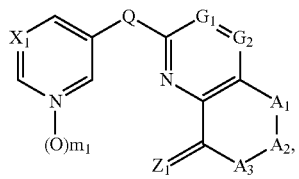

(I)

wherein
$X_1$ is nitrogen or $CR_1$;
$G_1$ is nitrogen or $CR_2$;
$G_2$ is nitrogen or $CR_3$;
or $G_1$-$G_2$ together is —S—, —O—, —NH—, or N—CH$_3$;
$A_1$ is oxygen, S(O)$n_1$, S(O)(=NR$_4$), C=O, NR$_5$, CR$_6$R$_7$, —CR$_8$CR$_9$— or a direct bond;
$A_2$ is oxygen, S(O)$n_2$, NR$_{10}$ or CR$_{11}$R$_{12}$;
$A_3$ is oxygen, NR$_{13}$, CR$_{14}$R$_{15}$ or —CR$_{16}$CR$_{17}$—;
or $A_2$-$A_3$ together represents a group —CR$_{18}$=CR$_{19}$—;
with the provisos that:
a) not more than 1 substituent A can be oxygen or sulpher;
b) not more than 2 substituents A can be nitrogen; and
c) 2 substituents A as nitrogen can be adjacent to each other or separated by a sulphur or carbon substituent;
$R_1$ is hydrogen or halogen;
$R_2$ and $R_3$, independently from each other, are hydrogen, halogen, $C_1$-$C_3$alkyl or $C_1$-$C_3$haloalkyl;
$R_4$, $R_5$, $R_{10}$ and $R_{13}$, independently from each other, are hydrogen, cyano, $C_1$-$C_2$alkyl, $C_3$-$C_6$cycloalkyl, $C_1$-$C_2$haloalkyl, C(O)$C_1$-$C_3$alkyl, (CO)OC$_1$-$C_3$alkyl, SO$_2$NHC$_1$-$C_3$alkyl, SO$_2$N(C$_1$-$C_3$alkyl), SO$_2$C$_1$-$C_3$alkyl, SO$_2$-phenyl, wherein the said phenyl can be mono- or polysubstituted on the phenyl ring by substituents selected from the group consisting of $C_1$-$C_3$alkyl, $C_1$-$C_3$haloalkyl, $C_1$-$C_3$alkoxy, $C_1$-$C_3$haloalkoxy, halogen, cyano and nitro;
$R_6$, $R_7$, $R_8$, $R_9$, $R_{11}$, $R_{12}$, $R_{14}$, $R_{15}$, $R_{16}$ and $R_{17}$, independently from each other, are hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_1$-$C_4$alkylcarbonyl, $C_1$-$C_6$alkoxycarbonyl, $C_1$-$C_6$alkylaminocarbonyl, $C_3$-$C_6$dialkylaminocarbonyl, $C_1$-$C_6$alkoxycarbonyloxy, $C_1$-$C_6$alkylaminocarbonyloxy, $C_3$-$C_6$dialkylaminocarbonyloxy, $C_1$-$C_4$alkoxyimino-$C_1$-$C_4$alkyl, —CONHSO$_2$—$C_1$-$C_6$-alkyl, —CONHSO$_2$N($C_1$-$C_6$-alkyl)$_2$, or are a three- to ten-membered, monocyclic or fused bicyclic ring system which may be aromatic, partially saturated or fully saturated, said three- to ten-membered, monocyclic or fused bicyclic ring system can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_6$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_1$-$C_4$alkylcarbonyl, $C_1$-$C_6$alkoxycarbonyl, $C_1$-$C_6$alkylaminocarbonyl, and $C_2$-$C_8$dialkylaminocarbonyl;

$R_{18}$ and $R_{19}$, independently from each other, are hydrogen, halogen, nitro, cyano, hydroxy, CHO, $C_1$-$C_6$alkyl, $C_2$-$C_6$alkenyl, $C_2$-$C_6$alkynyl, $C_1$-$C_6$alkoxy, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkylsulfonyl, $C_1$-$C_4$alkylsulfonyl-$C_1$-$C_4$alkyl, $C_1$-$C_4$alkylcarbonyl, $C_1$-$C_6$alkoxycarbonyl, $C_1$-$C_6$alkylaminocarbonyl, $C_3$-$C_6$dialkylaminocarbonyl, $C_1$-$C_6$alkoxycarbonyloxy, $C_1$-$C_6$alkylaminocarbonyloxy, $C_3$-$C_6$dialkylaminocarbonyloxy, $C_1$-$C_4$alkoxyimino-$C_1$-$C_4$alkyl, —CONHSO$_2$—$C_1$-$C_6$-alkyl, —CONHSO$_2$N($C_1$-$C_6$-alkyl)$_2$, or are a three- to ten-membered, monocyclic or fused bicyclic ring system which may be aromatic, partially saturated or fully saturated, said three- to ten-membered, monocyclic or fused bicyclic ring system can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_1$-$C_4$alkylcarbonyl, $C_1$-$C_6$alkoxycarbonyl, $C_1$-$C_6$alkylaminocarbonyl, and $C_2$-$C_8$dialkylaminocarbonyl;

$Z_1$ is oxygen, NOR$_{20}$, NR$_{21}$, N—NR$_{22}$R$_{23}$, or N—N(R$_{24}$)SO$_2$(R$_{25}$),
$R_{20}$, $R_{21}$, $R_{22}$ and $R_{25}$ independently from each other, are hydrogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkyl-$C_3$-$C_6$cycloalkylamino, $C_1$-$C_4$alkylcarbonyl, $C_1$-$C_6$alkoxycarbonyl, $C_1$-$C_6$alkylaminocarbonyl, $C_3$-$C_6$dialkylaminocarbonyl, —CONHSO$_2$—$C_1$-$C_6$-alkyl, —CONHSO$_2$N($C_1$-$C_6$-alkyl)$_2$ or are a five- to ten-membered monocyclic or fused bicyclic ring system which may be aromatic, saturated or partially saturated and may contain 1 to 4 heteroatoms selected from the group consisting of nitrogen, oxygen and sulfur, where the ring system is attached directly or via a $C_1$-$C_4$alkylene, $C_2$-$C_4$alkenyl-$C_1$-$C_4$alkylene, $C_2$-$C_4$alkynyl-$C_1$-$C_4$alkylene, —NH—$C_1$-$C_4$alkylene, —N($C_1$-$C_4$alkyl)$C_1$-$C_4$alkylene, SO—$C_1$-$C_4$alkylene, SO—$C_1$-$C_4$alkylene, —SO$_2$—$C_1$-$C_4$alkylene or O—$C_1$-$C_4$alkylene group to the heteroatom substituent, and where each ring system may not contain more than two oxygen atoms and not more than two sulfur atoms and the ring system for its part may be mono-, di- or trisubstituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, hydroxyl, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, halogen, cyano, nitro, phenyl and benzylthio, said phenyl and benzylthio can be mono- or polysubstituted on the phenyl ring by substituents selected from the group consisting of $C_1$-$C_3$alkyl, $C_1$-$C_3$haloalkyl, $C_1$-$C_3$alkoxy, $C_1$-$C_3$haloalkoxy, halogen, cyano and nitro, and where the substituents on the nitrogen in the heterocyclic ring are different from halogen;

$R_{23}$ and $R_{24}$ are hydrogen or $C_1$-$C_3$alkyl;

Q is a ring system $Q_1$

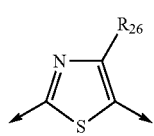

(Q$_1$)

wherein $R_{26}$ is hydrogen, halogen, $C_1$-$C_3$alkyl, $C_1$-$C_3$haloalkyl or is a three- to four-membered ring which can be partially saturated or fully saturated and can contain one heteroatom selected form the group consisting of nitrogen, oxygen and sulphur; said three- to four-membered ring system can be mono- to polysubstituted by substituents independently selected from the group consisting of halogen, methyl and trifluoromethyl; or $R_{26}$ is $C_2$-$C_6$alkenyl which can be mono- to polysubstituted by substituents independently selected from the group consisting of halogen, methyl and trifluoromethyl; or $R_{26}$ is $C_2$-$C_6$alkynyl which can be substituted by substituents selected from the group consisting of halogen, methyl and $C_1$-$C_2$haloalkyl;

$m_1$ is 0 or 1; and $n_1$ and $n_2$, independently from each other, are 0, 1 or 2; and agrochemically acceptable salts, enantiomers, tautomers and N-oxides of those compounds.

Compounds of formula I which have at least one basic centre can form, for example, acid addition salts, for example with strong inorganic acids such as mineral acids, for example perchloric acid, sulphuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulphinyl is, for example, methylsulphinyl, ethylsulphinyl, propylsulphinyl, isopropylsulphinyl, n-butylsulphinyl, isobutylsulphinyl, sec-butylsulphinyl, tert-butylsulphinyl; preferably methylsulphinyl and ethylsulphinyl.

Alkylsulphonyl is, for example, methylsulphonyl, ethylsulphonyl, propylsulphonyl, isopropylsulphonyl, n-butylsulphonyl, isobutylsulphonyl, sec-butylsulphonyl or tert-butylsulphonyl; preferably methylsulphonyl or ethylsulphonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

In the context of this invention, with regard to the definition of a ring system, the definition "where the ring system is attached directly or via a $C_1$-$C_4$alkylene, $C_2$-$C_4$alkenyl-$C_1$-$C_4$alkylene, $C_2$-$C_4$alkynyl-$C_1$-$C_4$alkylene, —NH—$C_1$-$C_4$alkylene, —N($C_1$-$C_4$alkyl)$C_1$-$C_4$alkylene, SO—$C_1$-$C_4$alkylene, $SO_2$—$C_1$-$C_4$alkylene, —$SO_2$—$C_1$-$C_4$alkylene or O—$C_1$-$C_4$alkylene group to the heteroatom substituent," the attachment of the ring system is on the left side of said definition, for example the group $NOR_{20}$ for the substituent $Z_1$ can be N—O—$CH_2$—$CH_2$—NH-pyridyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

In the context of this invention "halo-substituted phenyl" in the definition of the substituents, means for example a phenyl group which is mono- to polysubstituted by substituents selected from the group consisting of fluoro, chloro, bromo and iodo. Preferably "halo-substituted phenyl" is phenyl which is mono-di or tri-substituted by chloro, in particular mono-substituted by chloro.

According to this invention, a three- to ten-membered- or five- to ten-membered monocyclic or fused bicyclic ring system which may be aromatic, partially saturated or fully saturated; said ring system can contain 1 to 4 hetero atoms selected from the group consisting of nitrogen, oxygen and sulfur, it not being possible for each ring system to contain more than 2 oxygen atoms and more than 2 sulfur atoms; is, depending of the number of ring members, for example, selected from the group consisting of

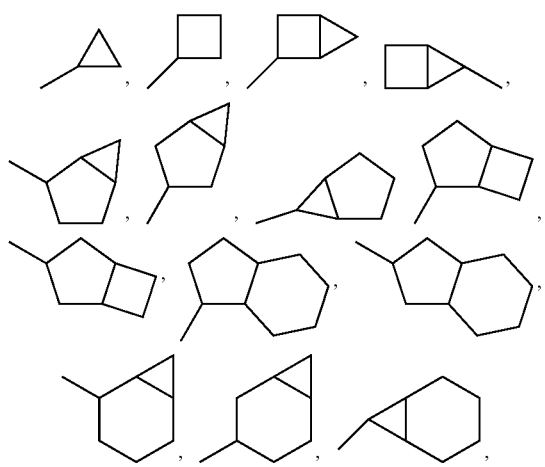

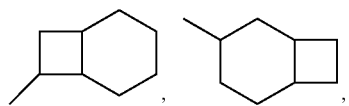

cyclopentyl, cyclohexyl, where said cycloalkyl groups for their part may be preferably unsubstituted or substituted by $C_1$-$C_6$alkyl or halogen, or is phenyl, benzyl, naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

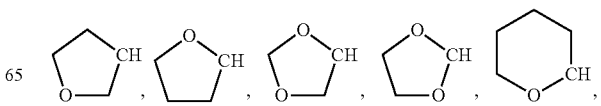

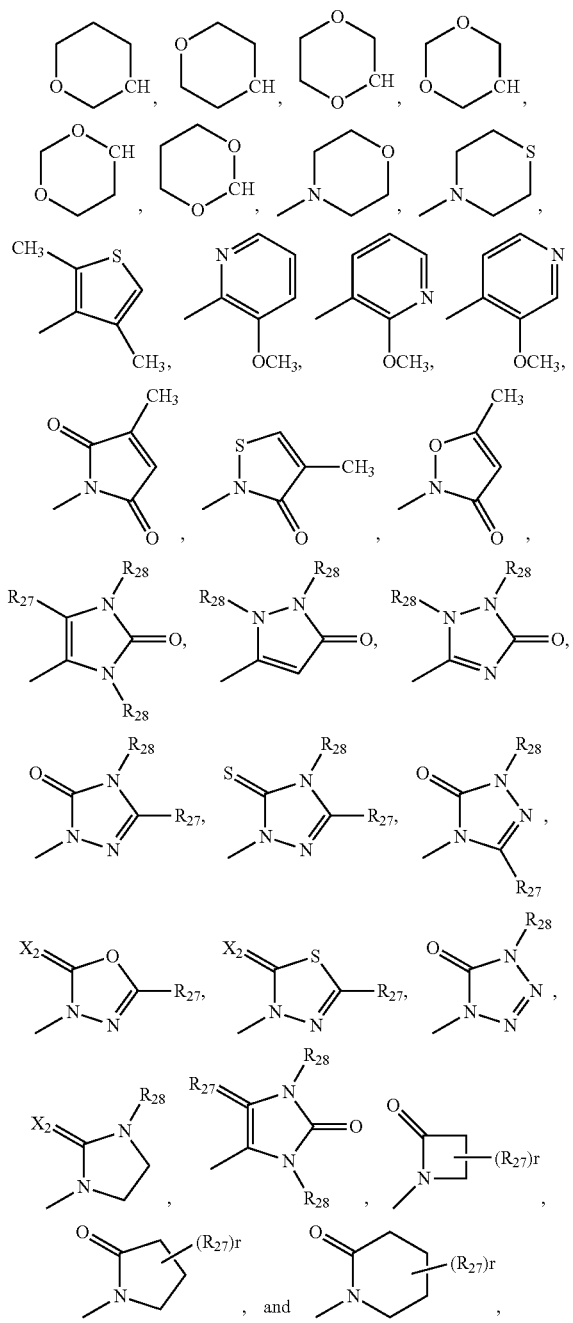

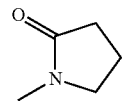

wherein each $R_{28}$ is hydrogen or methyl and each $R_{27}$ is hydrogen, $C_1$-$C_3$alkyl, $C_1$-$C_3$alkoxy, $C_1$-$C_3$alkylthio or trifluoromethyl, $X_2$ is oxygen or sulfur and r=1, 2, 3 or 4.

Where no free valency is indicated in those definitions, for example as in

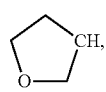

the linkage site is located at the carbon atom labelled "CH" or in a case such as, for example, at the bonding site indicated at the bottom left.

In preferred compounds of formula I,
$X_1$ is CH or C—F;
$A_1$ is oxygen, S(O)$n_1$, C=O, NR$_5$, CR$_6$R$_7$, —CR$_5$CR$_9$— or a direct bond;
$A_2$ is CR$_{11}$R$_{12}$; and
$A_3$ is CR$_{14}$R$_{15}$ or —CR$_{16}$CR$_{17}$— and
$R_{26}$ is hydrogen, halogen or $C_1$-$C_3$alkyl.

In further preferred compounds of formula I,
$X_1$ is CH or C—F;
$G_1$ is CR$_2$;
$G_2$ is CR$_3$; or
$G_1$-$G_2$ together is —S—, —O—;
$A_1$ is oxygen, S(O)$n_1$, C=O, NR$_5$, CR$_6$R$_7$, —CR$_8$CR$_9$— or a direct bond;
$A_2$ is CR$_{11}$R$_{12}$;
$A_3$ is CR$_{14}$R$_{15}$ or —CR$_{16}$CR$_{17}$—; and
$R_{26}$ is hydrogen, halogen or $C_1$-$C_3$alkyl.

In further preferred compounds of formula I,
$X_1$ is CH;
$G_1$ is CH;
$G_2$ is CH; or
$G_1$-$G_2$ together is —S—;
$A_1$ is oxygen, S(O)$n_1$, C=O, NR$_5$, CR$_6$R$_7$, —CR$_5$CR$_9$— or a direct bond;
$A_2$ is CR$_{11}$R$_{12}$;
$A_3$ is CR$_{14}$R$_{15}$ or —CR$_{16}$CR$_{17}$—; and
$R_{26}$ is hydrogen, halogen or $C_1$-$C_3$alkyl.

In further preferred compounds of formula I,
$X_1$ is CH;
$G_1$ is CH;
$G_2$ is CH; or
$G_1$-$G_2$ together is —S—;
$A_1$ is oxygen, S(O)$n_1$, C=O, NR$_5$, CR$_6$R$_7$, —CR$_5$CR$_9$— or a direct bond;
$A_2$ is CR$_{11}$R$_{12}$;
$A_3$ is CR$_{14}$R$_{15}$ or —CR$_{16}$CR$_{17}$—;
$R_{26}$ is hydrogen, halogen or $C_1$-$C_3$alkyl; and
$Z_1$ is NOR$_{20}$, N—NR$_{22}$R$_{23}$, or N—N(R$_{24}$)SO$_2$(R$_{25}$).

In further preferred compounds of formula I,
$X_1$ is CH;
$G_1$ is CH;
$G_2$ is CH; or
$G_1$-$G_2$ together is —S—;
$A_1$ is oxygen, S(O)$n_1$, C=O, NR$_5$, CR$_6$R$_7$, —CR$_8$CR$_9$— or a direct bond;
$A_2$ is CH$_2$;
$A_3$ is CH$_2$ or —CH$_2$CH$_2$—;
$R_{26}$ is hydrogen, halogen, $C_1$-$C_3$alkyl; and
$Z_1$ is NOR$_{20}$, N—NR$_{22}$R$_{23}$, or N—N(R$_{24}$)SO$_2$(R$_{25}$).

In further preferred compounds of formula I,
$X_1$ is CH;
$G_1$ is CH;
$G_2$ is CH;
$A_1$ is oxygen, S(O)$n_1$, C=O, NR$_5$, CH$_2$, —CH$_2$CH$_2$— or a direct bond;
$A_2$ is CH$_2$;
$A_3$ is CH$_2$ or —CH$_2$CH$_2$—;
$R_{26}$ is hydrogen, halogen or $C_1$-$C_3$alkyl; and
$Z_1$ is NOR$_{20}$, N—NR$_{22}$R$_{23}$, or N—N(R$_{24}$)SO$_2$(R$_{25}$).

In further preferred compounds of formula I,
$X_1$ is CH;
$G_1$ is CH;
$G_2$ is CH; or
$G_1$-$G_2$ together is —S—;
$A_1$ is oxygen, $S(O)n_1$, C=O, $NR_5$, $CH_2$, —$CH_2CH_2$— or a direct bond;
$A_2$ is $CH_2$;
$A_3$ is $CH_2$,
$R_{26}$ is hydrogen, halogen, $C_1$-$C_3$alkyl; and
$Z_1$ is $NOR_{20}$.

In further preferred compounds of formula I,
$X_1$ is CH;
$G_1$ is CH;
$G_2$ is CH;
$A_1$ is oxygen, $S(O)n_1$, $NR_5$, $CH_2$ or a direct bond;
$A_2$ is $CH_2$;
$A_3$ is $CH_2$,
$R_{24}$ is hydrogen, halogen or $C_1$-$C_3$alkyl; and
$Z_1$ is $NOR_{20}$, N—$NR_{22}R_{23}$, or N—$N(R_{24})SO_2(R_{25})$.

Preferred compounds of formula I are represented by the compounds of formula Iaa

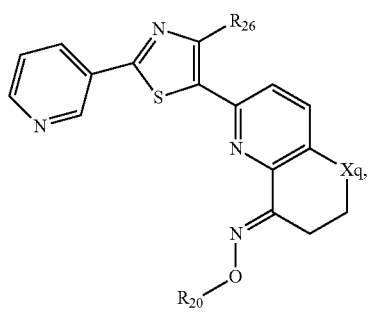
(Iaa)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Ibb

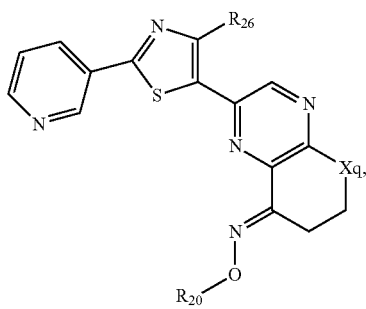
(Ibb)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Icc

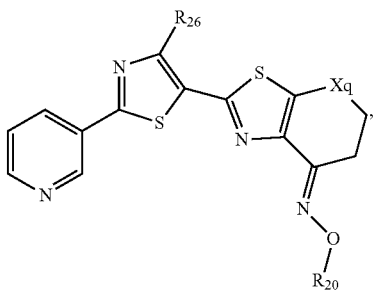
(Icc)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Idd

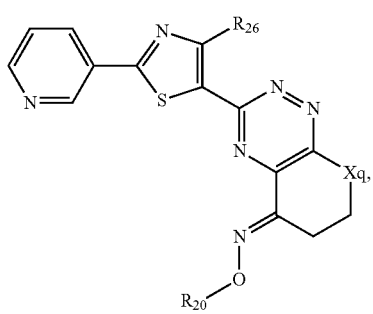
(Idd)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Iee

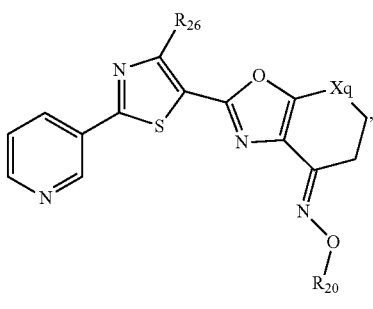
(Iee)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Iff

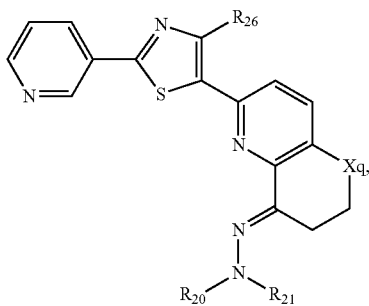

(Iff)

$R_{20}$ is hydrogen or $C_1$-$C_6$alkyl;

$R_{21}$ is hydrogen, $C_1$-$C_6$alkyl, $C_1$-$C_6$alkoxycarbonyl or $C_1$-$C_6$alkylsulfonyl;

$R_{26}$ is hydrogen or $C_1$-$C_6$alkyl, and

Xq is oxygen, —$CH_2$—, —N($C_1$-$C_6$alkyl)- or —N($C_1$-$C_6$alkylsulfonyl)-.

Further preferred compounds of formula I are represented by the compounds of formula Igg

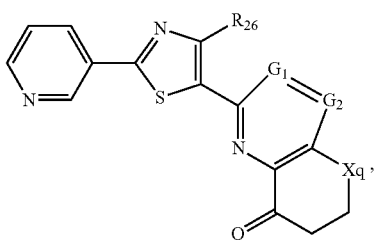

(Igg)

wherein $G_1$ is CH;

$G_2$ is CH;

$R_{26}$ is hydrogen or $C_1$-$C_6$alkyl, and

Xq is oxygen, —$CH_2$—, —N($C_1$-$C_6$alkyl)- or —N($C_1$-$C_6$alkylsulfonyl)-.

Especially preferred compounds of formula I are selected from the compounds of formula I-1

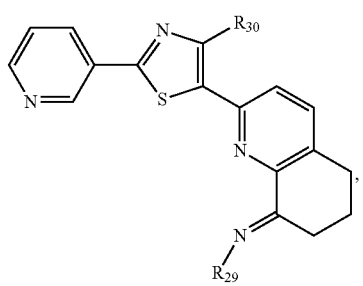

(I-1)

wherein $R_{29}$ is OH, $C_1$-$C_6$alkoxy, $C_2$-$C_6$alkenyloxy, or $N(R_{31})R_{32}$, wherein $R_{31}$ is hydrogen;

$R_{32}$ is $C_1$-$C_6$alkoxycarbonyl; and $R_{30}$ is $C_1$-$C_6$alkyl; and the compounds of formula I-2

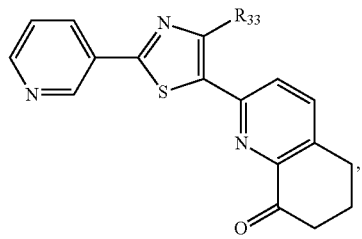

(I-2)

wherein $R_{33}$ is $C_1$-$C_6$alkyl.

An especially preferred group of compounds of formula I is represented by the group consisting of the compounds of formula I-3

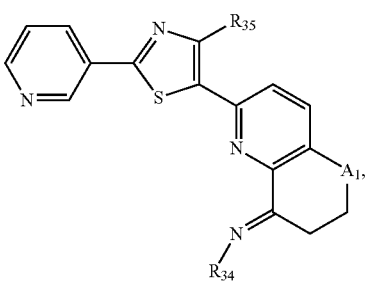

(I-3)

wherein $R_{34}$ is $C_1$-$C_6$alkoxy, $C_1$-$C_6$haloalkoxy, phenyl-$C_1$-$C_6$alkoxy, wherein the phenyl group itself can be mono- or disubstituted by substituents selected from the group consisting of halogen and $C_1$-$C_6$haloalkyl, or is dioxolanyl-$C_1$-$C_6$alkoxy or pyrrolidinyl-$C_1$-$C_6$alkoxy wherein the pyrrolidine group can be N-substituted by $C_1$-$C_4$ alkyl, or is morpholinyl-$C_1$-$C_6$alkoxy, $C_2$-$C_6$alkenyloxy, $C_2$-$C_6$haloalkenyloxy, hydroxy, phenyl-$C_2$-$C_6$alkynyloxy, $C_3$-$C_6$cycloalkyloxy, phenylthio-$C_1$-$C_6$alkoxy, wherein the phenyl group itself can be substituted by halogen, or is pyridyl-$C_1$-$C_6$alkoxy, wherein the pyridine group itself can be mono- or disubstituted by halogen, or is triazolyl-$C_1$-$C_6$alkoxy, wherein the triazole group itself can be mono- or disubstituted by substituents selected from the group consisting of $C_1$-$C_6$alkyl and $C_1$-$C_6$haloalkyl, tetrahydropyranyl-$C_1$-$C_6$alkoxy, 1,3-dioxolan-2-yl-$C_1$-$C_6$alkoxy or $N(R_{36})R_{37}$, wherein $R_{36}$ is hydrogen or $C_1$-$C_6$alkyl and $R_{37}$ is phenyl which can be mono- or disubstituted by substituents selected from the group consisting of halogen and $C_1$-$C_6$alkoxy, or is $C_1$-$C_6$haloalkyl, $C_1$-$C_6$alkoxycarbonyl, $C_1$-$C_6$alkylsulfonyl, pyrimidinyl, pyridyl;

$R_{35}$ is hydrogen, $C_1$-$C_6$alkyl; and
$A_1$ is oxygen or —$CH_2$—;
the compounds of formula I-4

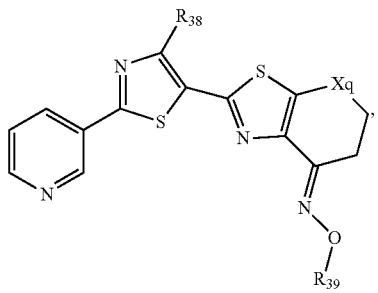

(I-4)

wherein
$R_{38}$ is $C_1$-$C_6$alkyl;
$R_{39}$ is $C_1$-$C_6$alkyl, $C_2$-$C_6$alkenyl and Xq is sulphur;
and the compounds of formula I-5

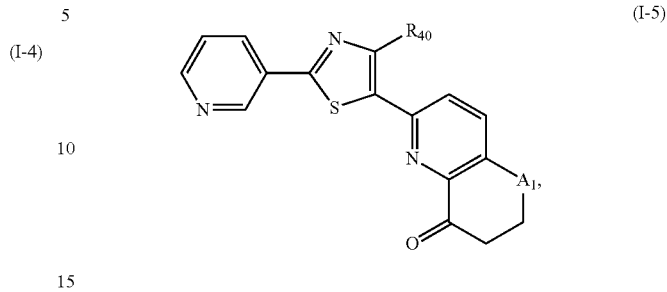

(I-5)

wherein
$R_{40}$ is hydrogen or $C_1$-$C_6$alkyl; and
$A_1$ is oxygen or —$CH_2$—.

The process according to the invention for preparing compounds of formula I is carried out in principle by methods known to those skilled in the art, or those shown in schemes 1-4.

Scheme 1:

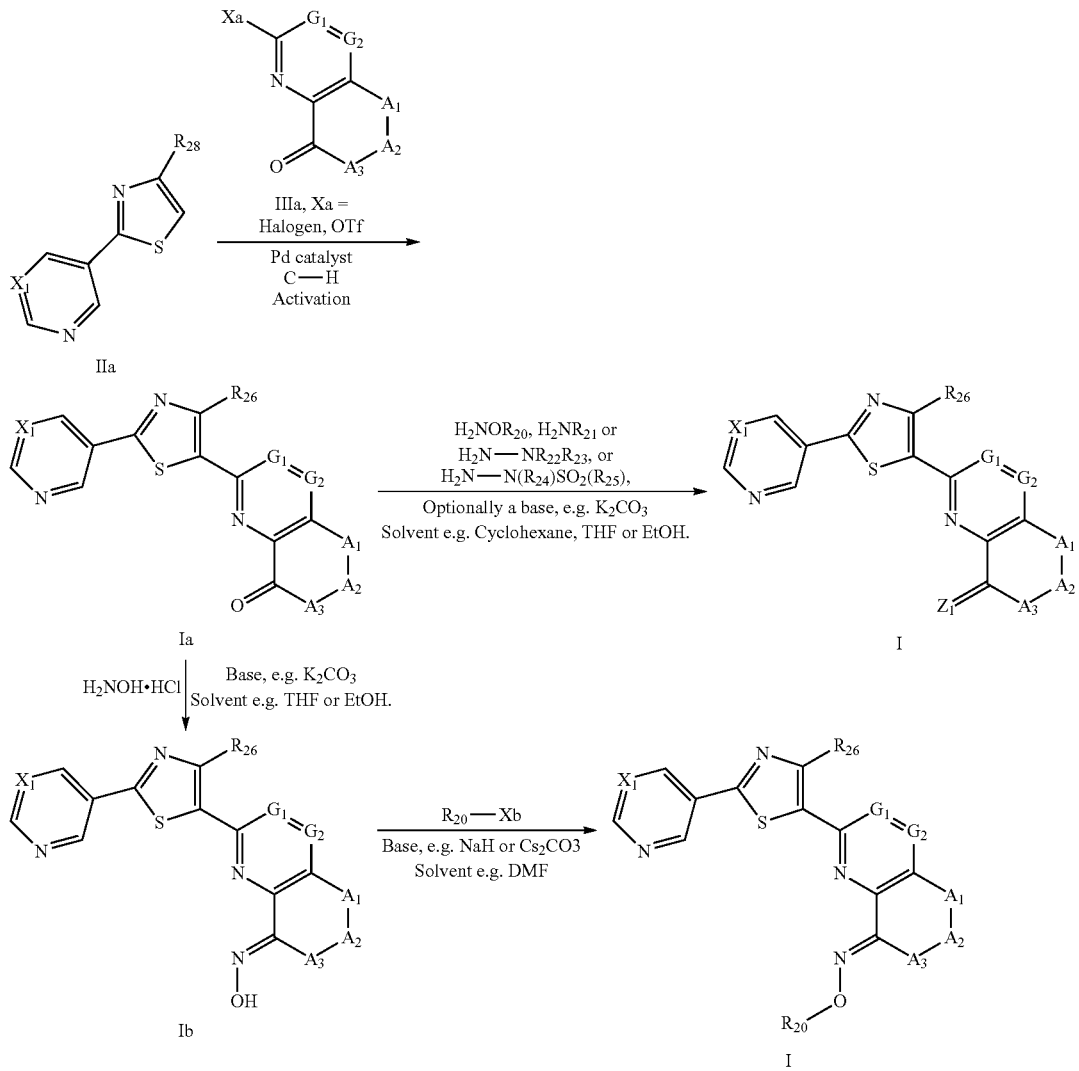

In scheme 1, compounds of formula IIa (prepared as, for example in WO 2010/006713) can be coupled to compounds of formula IIIa wherein $G_1$, $G_2$, $A_1$, $A_2$, $A_3$, $X_1$ and $R_{26}$ are defined as described for formula I, and Xa is a leaving group such as halogen or triflate using C—H activation methodology. Here, a compound of formula IIa is treated with a compound of formula IIIa, in an inert solvent, such as DMF, or tetrahydrofurane, with a palladium catalyst, such as Pd(OAc)$_2$, with an appropriate ligand, such as tri-t-butyl phosphine, optionally in the presence of a base such as potassium carbonate, at temperatures between 25-150° C. Such C—H activation technology is known to those skilled in the art, and has been described in, for example, e.g. L. Ackermann et al. *Angew. Chem. Int Ed.*, 48, 9792, 2009, J. Q. Yu, Z. Shi Eds., *Topics in Current Chemistry*, 2010, vol. 292, Springer, or US pat. Appl. 2011212949. Compounds of formula I so obtained can be condensed with either $H_2NOR_{20}$, $H_2NR_{21}$, $H_2N$—$NR_{22}R_{23}$, $H_2N$—$N(R_{24})SO_2(R_{25})$, optionally in the presence of a base, for example potassium carbonate, or a dehydrating agent, such as 0.4 nm molecular sieves in an inert solvent, such as tetrahydrofuran, or hexane, or protic solvents, for example ethanol, at temperatures between 25° C. and 150° C., preferably between 25° C. and 80° C. Such chemistries are well known in the literature, for example for compounds where $Z_1$ is $N(R_{24})SO_2(R_{25})$ can be prepared according to Ito et al *Bull. Chem. Soc.* Japan, 51, 953, 1978 or Wu et al, *Synthesis*, 249, 1996. For compounds where $Z_1$ is N—$OR_{20}$ a whole range of methods are known for their preparation and to those skilled in the art as exemplified for example in "*Reaktionen der organischen Synthese*", Cesare Fern, Georg Thieme Verlag, Stuttgart, 1978, p. 540-541.

Similarly, compounds of formula I where $Z_1$ is N—$NR_{22}R_{23}$, are also readily prepared to those skilled in the art and more specifically as described in "*Reaktionen der organischen Synthese*", Cesare Fern, Georg Thieme Verlag, Stuttgart, 1978, p. 537-538.

A further synthesis of compounds of formula I are illustrated in scheme 2.

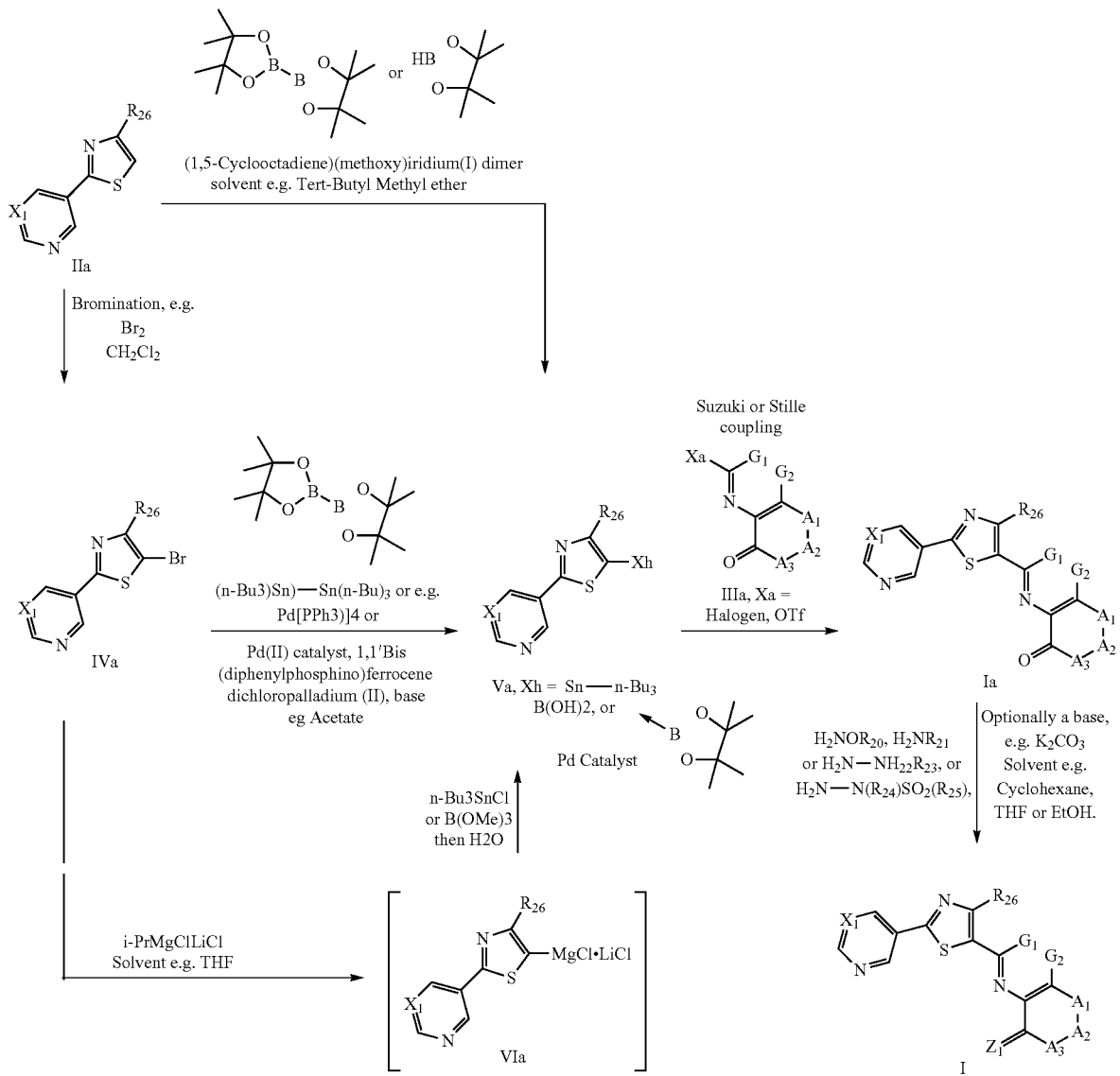

In scheme 2, compounds of formula IIa, prepared as described in for example WO 2010006713, can be converted directly to compounds of formula Va (wherein Xh is pinacolborane) by activating the C—H bond of IIa with an iridium catalyst, e.g. (1,5-Cyclooctadiene)(methoxy)iridium(I) dimer and bis(pinacolato)diboron or pinacolborane in an inert solvent such as tert-butyl methyl ether as described in, for example, *J. Am. Chem. Soc.* 122, 12868, 2000, or *Chem. Rev.*, 110, 890, 2010. Alternatively compound IIa can be converted to the bromide IVa by treatment with bromine in an inert solvent such as dichloromethane. The resultant IVa upon treatment with hexabutylditin, in an inert solvent, such as dioxane, and Tetrakis(triphenylphosphine)palladium(0), in the presence of lithium chloride at elevated temperatures leaves to compounds of the formula Va wherein Xh is Sn(n-Butyl)3 (see for example *J. Med. Chem*, 48(6), 1886, 2005). In a yet another method to prepare Va wherein Xh is Sn(n-Butyl)3, the bromide can be metallated with a Grignard reagent, for example i-PrMgCl.LiCl, in tetrahydrofurane at low temperatures, and the intermediate organo magnesium compound VIa treated with tri-n-butyl tin chloride to give the product IVa, wherein Xh is tri-n-butyl tin.

In a similar fashion, compounds IVa where Xh is a boronic acid, or pinacolborane can be made from the bromine by a using a palladium coupling with bis(pinacolato)diboron as described in for example WO 2009151598, or by quenching the organo magnesium compound VIa, with trimethoxy borane, followed by aqueous work-up. Compounds of formula Va can then be converted to compounds of formula Ia by Stille or Suzuki coupling as described in scheme 1. The compounds of formula Ia can be converted to compounds of formula I as described in scheme 1.

A further synthesis for compounds of formula I is illustrated in scheme 3:

Scheme 3:
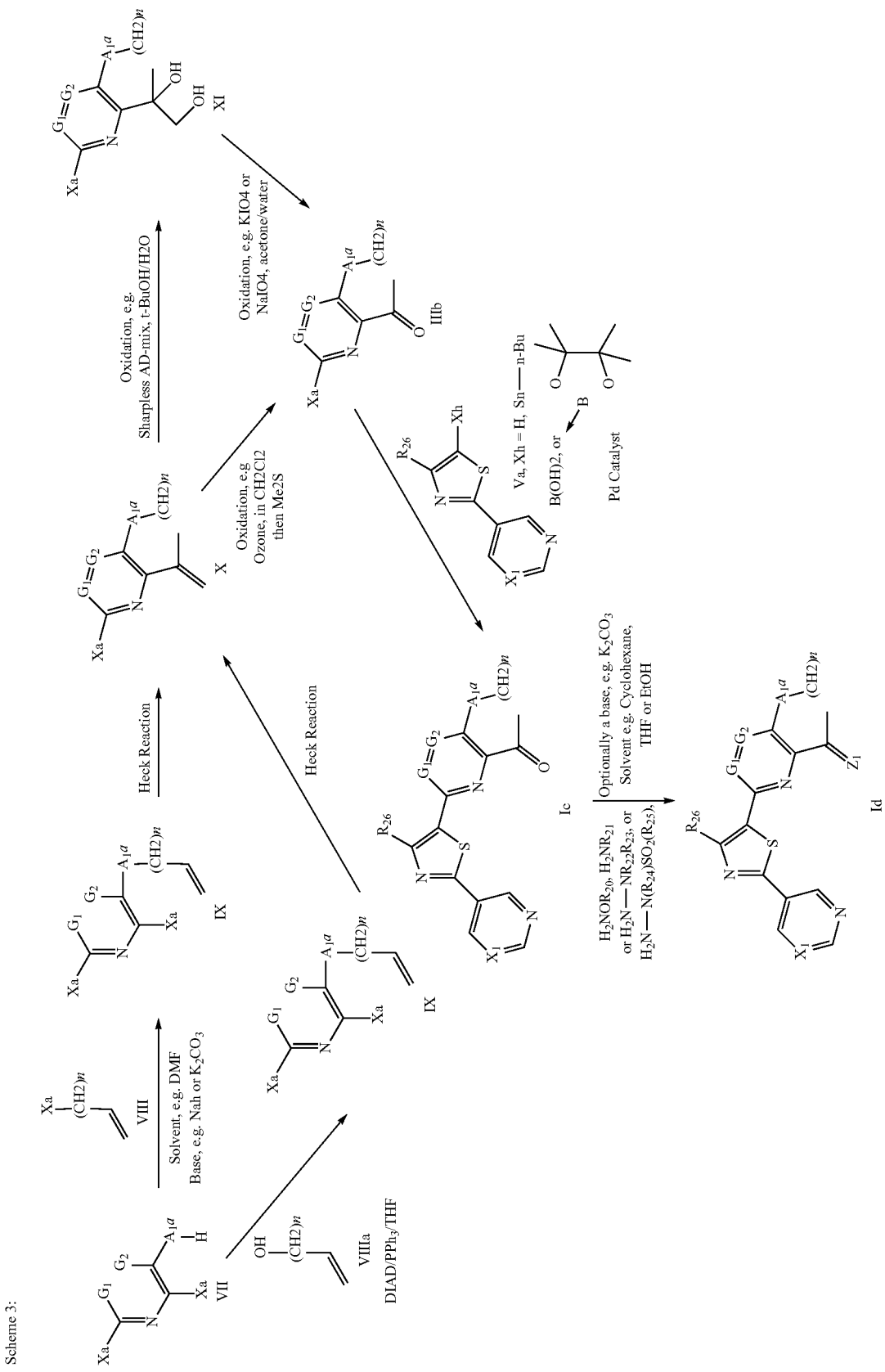

In scheme 3, a compound of formula VII, wherein Xa is halogen, n is 1, 2, or 3, and $A_{1a}$ is oxygen, sulpher, $NR_5$, or $SO_2NR_{10}$, and wherein $G_1$, $G_2$, $R_5$, and $R_{10}$ are as defined for formula I, is converted to a compound of formula IX by alkylation with a compound of formula VII (wherein Xa is halogen, and n is 1, 2, or 3) by treatment with a base, for example potassium carbonate, in an aprotic solvent, for example dimethylformamide by methods known to those skilled in the art. Alternatively, compounds of formula IX can be prepared by Mitsunobu reaction of a compound of formula VII and a compound of formula VIIIa, in THF. Such Mitsunobu reactions are well precedented in the literature (see for example K. C. Kumara Swamy et al, Chem. Rev, 2009, 109, 2551-2651). Compounds of formula IX are converted to compounds of formula X by Heck reaction. Typically this reaction requires a palladium catalyst (for example Palladium (II) acetate and a base (for example potassium acetate) in a solvent (for example dimethyl formamide) at elevated temperatures. In the case of compounds of formula IX the olefinic reaction partner and the aromatic halide reaction partner are both located in the same molecule so the Heck reaction is intramolecular. Such intramolecular Heck reactions have been reported in the literature (see Overman, L. E. In Metal-catalyzed Cross-coupling Reactions, Ed Diederich, F.; Wiley-VCH: New York, 1998, pp. 231-269 and Gibson, S. E., Middleton, R. *J. Contemp. Org. Synth.* 1996, 3, 447-471). Compounds of formula IX can be converted to compounds of formula IIIb directly by treatment with ozone in an inert solvent such as methylene chloride, followed by reductive work-up with for example dimethyl sulfide or in a stepwise fashion by first dihydroxylating the double bond of compounds of formula X to give compounds of formula XI using for example conditions reported in J. Org. Chem. 1992, 57, 2768-2771 and then oxidatively cleaving the 1,2-diol function in compounds of formula XI with for example an alkali metal salt of periodate in a solvent mixture such as acetone and water. The remaining steps of the synthesis of compounds of formula Id, wherein, n is 1, 2, or 3, and $A_{1a}$ is oxygen, sulpher, $NR_5$, or $SO_2NR_{10}$, $X_1$, $Z_1$, $G_1$, $G_2$, $R_5$, $R_{26}$ and $R_{10}$ are as defined for formula I, is completed by the methods described in scheme 1 and scheme 2.

Alternatively compounds of formula 1d can be prepared as shown in scheme 4 which utilizes the same chemistry as shown in scheme 3 but in a different order resulting in the novel intermediates XII and XIII (wherein, n is 1, 2, or 3, and $A_{1a}$ is oxygen, sulpher, $NR_5$, or $SO_2NR_{10}$, $X_1$, $Z_1$, $G_1$, $G_2$, $R_5$, $R_{26}$ and $R_{10}$ are as defined for formula I)

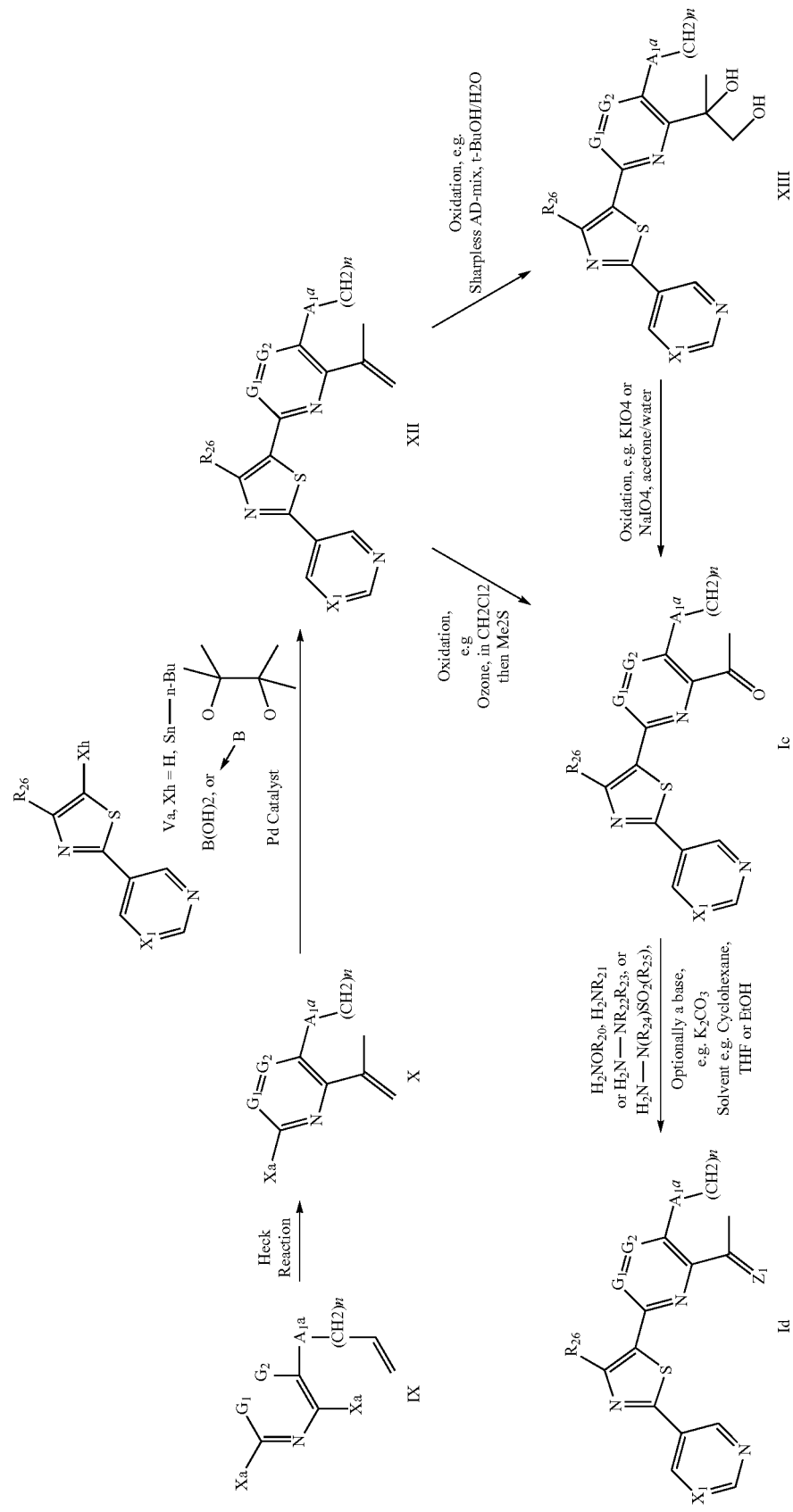

Synthesis of compounds of formula I wherein $X_1$, $Z_1$, $G_1$ is sulpher $G_2$ is a direct bond, $A_1$ is $S(O)n_1$, $A_2$ and $A_3$ are methylene, and $Z_1$ and $X_1$ are described for formula I, i.e preparation of compounds of formula Ie can be prepared as described in scheme 5 and the preparative examples.

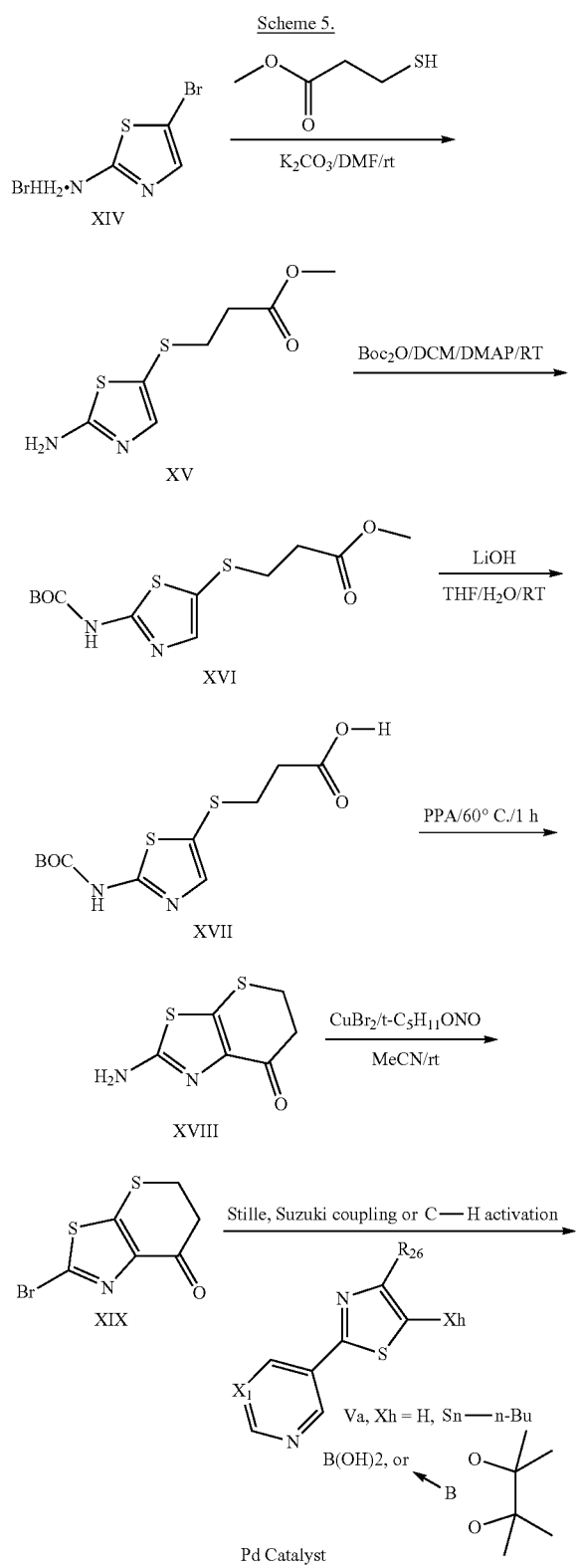

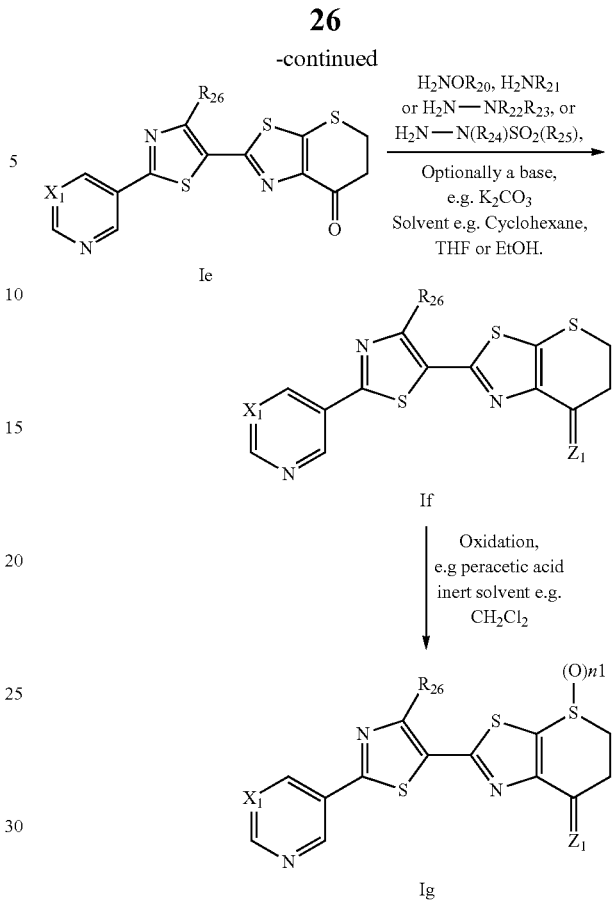

In compounds Ia, Ib, Ic, Id, Ie, If, Ig, IIa, IIIa, IVa, Va, and VIa, $G_1$, $G_2$, $A_1$, $A_2$, $A_3$, $X_1$, $Z_1$ and $R_{26}$ are as defined as in formula I. For preparing all further compounds of the formula I functionalized according to the definitions of $G_1$, $G_2$, $A_1$, $A_2$, $A_3$, $X_1$, $R_{24}$, and $Z_1$ there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereose-lective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity. The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp., *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp., *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp., *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp., *Empoasca* spp., *Eriosoma larigerum*, *Erythroneura* spp., *Gascardia* spp., *Glycaspis brimblecombei*, *Hyadaphis pseudobrassicae*, *Hyalopterus* spp., *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp., *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis* geminate from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example, *Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp; from the order Thysanura, for example, *Lepisma saccharina*.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice). The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonizing nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetestoxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera). Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II0 (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); Nature-Gard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain *Coleoptera* insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration numberC/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment of the invention, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823,U.S. Pat. No. 5,631,072, WO 2005/64072, WO2006/128870, EP 1724392, WO2005113886 or WO 2007/090739.

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type. In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp.,

*Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., Psorergatesspp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and Laminosioptes spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettablepowders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-me-thylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopo-lypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylpheno-xypolyethoxyethanol, polyethylene glycol or octylphenoxypolyethoxyethanol. Also suitable are fatty acid esters of polyoxyethylene sorbitan, such as polyoxyethylene sorbitan trioleate. The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl-ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutyl-naphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:
active ingredient: 1 to 95%, preferably 5 to 20%
surfactant: 1 to 30%, preferably 10 to 20 cYO
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

"M.p." means melting point in ° C.

Example P1

Preparation of 2-[4-methyl-2-(3-pyridyl)thiazol-5-yl]-6,7-dihydro-5H-quinolin-8-one (Compound 7.01)

A mixture of 2-chloro-6,7-dihydro-8(5H)-quinolinone (0.100 g, 0.551 mmol, prepared as described in J. Org. Chem., 55, 4789-91, 1990) and 4-methyl-2-(3-pyridyl)thiazole (0.116 g, 0.661 mmol, WO 2010006713), potassium acetate (0.0648 g, 0.661 mmol) in DMA (2.8 mL) was stirred at ambient temperature under argon. To this solution was added [1,2-Bis(dppe)]Cl$_2$Pd(II) (0.0159 g, 0.0275 mmol) and the solution irradiated in a microwave reactor at a temperature of 170° C. for 20 min. LCMS analysis showed the product and starting materials. Further irradiation at 190° C. led to no change and thus a further 0.0648 g of potassium acetate, and 0.0159 g mol of [1,2-Bis(dppe)]Cl$_2$Pd(II) were added and irradiation continued at 180° C. for 20 min. LC-MS showed reaction completion. The reaction mixture was diluted with water and extracted with ethyl acetate. The organic phase was then washed with successively saturated aqueous NaHCO$_3$ and brine, the organic phase dried over anhydrous Na$_2$SO$_4$, filtered and concentrated in vacuo. Purification by flash chromatography eluting with 0 to 100% ethyl acetate and then 10% MeOH in CH$_2$Cl$_2$ gave the title product (55 mg, 31%) as a beige solid.

LCMS: 0.81 Min, 322 (M+1)

$^1$H NMR (400 MHz, CHLOROFORM-d) d ppm 2.18-2.31 (m, 2H); 2.79 (s, 3H); 2.84 (t, J=6.42 Hz, 2H) 3.07 (t, J=6.42 Hz, 2H) 7.35-7.43 (m, 1H) 7.65-7.72 (m, 1H) 7.72-7.78 (m, 1H) 8.25 (d, J=8.07 Hz, 1H) 8.66 (d, J=3.67 Hz, 1H) 9.21 (s, 1H).

Alternative Synthesis Using Stille Coupling:

Step a: tributyl-[4-methyl-2-(3-pyridyl)thiazol-5-yl] stannane

In a dry flask under argon, 5-bromo-4-methyl-2-(3-pyridyl)thiazole (15.00 g, 55.85 mmol) was dissolved in THF (140 mL), and with cooling to keep the temperature at 25°-30° C., treated dropwise with i-PrMgCl.LiCl (TurboGrignard, 60 mL, 78.19 mmol,). The resulting mixture was allowed to stir at ambient temperature for 1 hour. The reaction mixture was then cooled to 10° C., and tri-n-butyl tin chloride (19 mL, 67.02 mmol) was added over 5 min. The reaction was stirred for 30 min at ambient temperature and then at reflux (66° C.) for 18 hours. The reaction mixture was quenched with saturated NH$_4$Cl solution and diluted with ethyl acetate. Then aqueous layer was extracted 3 times with ethyl acetate and the combined organic layers washed with brine, dried over MgSO$_4$, filtrated and evaporated. Purification by Combi flash chromatography with a column of 24 g and a gradient cyclohexane: 0-100% ethyl acetate to give the title compound as a yellow solid (9.17 g, 26%).

Step b: 2-[4-methyl-2-(3-pyridyl)thiazol-5-yl]-6,7-dihydro-5H-quinolin-8-one (Compound 7.01)

In a MW vial, 2-chloro-6,7-dihydro-5H-quinolin-8-one (0.215 g, 1.18 mmol) and tributyl-[4-methyl-2-(3-pyridyl)thiazol-5-yl]stannane (0.500 g, 1.07 mmol) were stirred in 1,4-dioxane (3.6 mL, 1.07 mmol) at ambient temperature. This yellow solution was degassed with an argon flux for 10 min and Tetrakis(PPh3)Pd(O) (0.124 g, 0.107 mmol) was added. The solution was irradiated in MW at 160° C. for 40 min. The crude was diluted with dichloromethane, NaOH (1 M) and NaHCO3 sat aq were added and aqueous layer was extracted 3 times with dichloromethane. The organic phase was then washed with brine, dried over Na$_2$SO$_4$ anhydrous, filtered and concentrated. Purification by column with a gradient of dichloromethane+0-10% methanol gave the title compound as a beige solid, yield: 92%. LCMS: 0.81 Min, 322 (M+1).

Example P2

2-[4-methyl-2-(3-pyridyl)thiazol-5-yl]-6,7-dihydro-5H-quinolin-8-one oxime (Compound 1.025)

A solution of 2-[4-methyl-2-(3-pyridyl)thiazol-5-yl]-6,7-dihydro-5H-quinolin-8-one (0.024 g, 0.067 mmol) was dissolved in ethanol (1 mL) and pyridine (0.054 mL, 0.053 g, 0.67 mmol) was added at ambient temperature. To this was added H2N—OH.HCl (0.0070 g, 0.10 mmol) and the resulting yellowish suspension was stirred at ambient temperature monitoring by LCMS. The reaction was complete after 2 hours. The reaction mixture was diluted with water and extracted ethyl acetate. The organic phase was then washed with brine, dried over anhydrous Na$_2$SO$_4$, filtered and concentrated in vacuo. Purification by flash chromatography eluting with a 5 to 10% MeOH: CH$_2$Cl$_2$, gradient gave 13 mg (58%) of the title compound as a yellow solid, and as a single isomer with mp=212-215° C.

LCMS (+ve); 0.83 min, 337 (M+1).

$^1$H NMR (400 MHz, CHLOROFORM-d) δ ppm 1.92-2.01 (m, 2H); 2.75-2.77 (m, 2H); 2.86 (t, J=6.0 Hz, 2H); 2.98 (t, J=6.0 Hz, 2H); 7.52-7.60 (m, 2H); 8.28 (dt, J=7.79, 1.97 Hz, 1H); 8.65 (dd, J=4.77, 1.47 Hz, 1H); 9.21 (d, J=1.47 Hz, 1H).

Example P3

Methyl N-[(E)-[2-[4-methyl-2-(3-pyridyl)thiazol-5-yl]-6,7-dihydro-5H-quinolin-8-ylidene]amino]carbamate (Compound 6.011)

A solution of 2-[4-methyl-2-(3-pyridyl)thiazol-5-yl]-6,7-dihydro-5H-quinolin-8-one (0.030 g, 0.093 mmol), methyl N-aminocarbamate hydrochloride (0.018 g, 014 mmol)) and acetic acid (1drop) were dissolved in methanol (0.9 mL) at ambient temperature and the resulting orange solution was stirred at 75° C. for 1 hour: LC-MS after this time showed reaction completion. The mixture was diluted with ethyl acetate, and then washed successively with saturated aqueous NaHCO$_3$ and then water. The organic phase was, dried over anhydrous Na$_2$SO$_4$, filtered and concentrated in vacuo. Purification by flash chromatography eluting with 0%-10% Methanol: Dichlormethane gradient gave the title product (29 mg, 79%) as yellow-orange solid. mp: 194-200° C.

LCMS (+ve); 0.94 min, 394 (M+1)

$^1$H NMR (400 MHz, CHLOROFORM-d) δ ppm; 2.05 (quin, J=6.0 Hz, 2H); 2.78 (s, 3H); 2.87 (br. s., 2H); 2.94 (t, J=6.0 Hz, 2H); 3.91 (br. s., 3H); 7.42 (dd, J=7.70, 4.4 Hz, 1H); 7.60 (d, J=8.1 Hz, 1H); 7.73 (d, J=8.1 Hz, 1H) 8.28 (d, J=7.70 Hz, 1H) 8.68 (d, J=4.4 Hz, 1H); 9.21 (br. s., 1H); 14.01 (br. s., 1H).

LCMS (+ve); 0.94 min, 394 (M+1)

Example P4

2-[2-(3-pyridyl)thiazol-5-yl]-6,7-dihydro-5H-quinolin-8-one (Compound 7.002)

Step a: 2-(3-pyridyl)-5-(4,4,5,5-tetramethyl-1,3,2-dioxaborolan-2-yl)thiazole

A screw cap vial was charged with bis-pinacolato-diboron (1.894 g, 1.10 equiv., 7.459 mmol), 4-tert-butyl-2-(4-tert-butyl-2-pyridyl)pyridine (0.182 g, 0.1 equiv., 0.678 mmol), di-mu-methoxobis(1,5-cyclooctadiene)diiridium (0.091 g, 0.02 equiv., 0.135 mmol) and tert-butyl dimethyl ether (TBME, 10 mL) under argon. The mixture was stirred at ambient temperature for 5 min until a deep red color appeared. To this solution was added 2-(3-pyridyl)thiazole (1.10 g, 1 equiv., 6.78 mmol), the vial was sealed and heated in the microwave to 80° C. for 5 min. The mixture was cooled down, the volatiles removed under reduced pressure and the residue purified by column chromatography on silica gel (eluant gradient: Heptane/ethyl acetate 1:0 to 1:1) to provide the title compound (1.14 g, 3.96 mmol, 58%) as brownish crystals.

$^1$H-NMR (CDCl3, 400 MHz) δ=9.32 (m, 1H), 8.68 (dd, 1H), 8.32 (s, 1H), 8.30 (m, 1H), 7.42 (dd, 1H), 1.30 (s, 12H).

Step b: Preparation of 2-[2-(3-pyridyl)thiazol-5-yl]-6,7-dihydro-5H-quinolin-8-one (Compound 7.002)

A screw cap vial was charged with acetonitrile (8 mL), water (2.5 mL) and Na$_2$CO$_3$ (1.41 g, 13.0 mmol, 4.7 equiv.) and degassed by bubbling nitrogen through for 10 min. Then 2-(3-pyridyl)-5-(4,4,5,5-tetramethyl-1,3,2-dioxaborolan-2-yl)thiazole (800 mg, 2.78 mmol, 1.0 equiv.), 2-chloro-6,7-dihydro-5H-quinolin-8-one (807 mg, 4.44 mmol, 1.6 equiv.) and Pd(PPh$_3$)$_4$ (161 mg, 0.139 mmol, 0.05 equiv.) were added and the mixture was heated to 80° C. for 18 hours. Water was added to the mixture, the aqueous phase was extracted twice with ethyl acetate, the combined organic phase were washed with brine, dried over Na$_2$SO$_4$ and concentrated in vacuo. The residue was purified by column chromatography on silica gel (eluant gradient: Heptane/ethyl acetate 1:0 to 0:1) to afford the title compound (180 mg, 0.58 mmol, 21%) as brown crystals. LCMS (+ve); 0.76 min, 308 (M+1)

Example P5

N-methoxy-6-[4-methyl-2-(3-pyridyl)thiazol-5-yl]-2,3-dihydropyrano[3,2-b]pyridin-4-imine (Compound 1.032)

Step a: 2,6-dibromopyridin-3-ol

To a 3N aqueous NaOH solution (790 ml) was added bromine (40.7 ml, 0.789 mol) at 0° C. An ice cooled solution of pyridine-3-ol (25 g, 0.263 mol) in 150 ml 10% NaOH solution was then added slowly and the mixture was stirred at ambient temperature for 18 hours, filtered and the filtrate was acidified with conc. HCl to pH 2. The precipitate was filtered off, washed with H$_2$O, and dissolved in Ethyl acetate (300 mL). The solution was dried over MgSO$_4$ and concentrated in vacuo. Purification by silica column flash chromatography (petroleum/Ethyl acetate, 3/1) to give the title product as an off white solid (23.6 g, 36%). $^1$H NMR (400 Mz, DMSO-d$^6$): δ: 7.23 (d, J=7.5, 1H); 7.45 (d, J=9, 1H); δ 11.13 (s, 1H), Step b: 2,6-dibromo-3-but-3-enoxy-pyridine To a stirred mixture of 2,6-dibromopyridin-3-ol (47.3 g, 0.188 mol) and but-3-en-1-ol (13.8 g, 0.191 mol) in anhydrous THF (200 mL) at 0° C. was added PPh$_3$ (59.4 g, 0.226 mol), followed by diisopropylazo dicarboxylate (DIAD, 41.77 g, 0.207 mol). The mixture was heated at reflux for 1 hour and then concentrated in vacuo to give a dark brown oil. The oil was dissolved in Ethyl acetate, washed with saturated NaHCO$_3$ solution and brine, dried with Na$_2$SO$_4$, and concentrated in vacuo. Petroleum (300 mL) was added to the crude product mixture. The white solid was removed by filtration, and the filtrate was purified by silica gel chromatography (petroleum/Ethyl acetate, 30/1) to afford compound the title compound as oil (49 g, 85%). $^1$H NMR (400 Mz, DMSO-d$^6$): δ: 2.62-2.59 (m, 2H); 4.07-4.03 (t, J=6, 2H); 5.22-5.11 (m, 1H); 5.96-5.83 (m, 1H); 7.01 (d, J=7.2); 7.33 (d, J=9.3, 1 H).

Step c: 6-bromo-4-methylene-2,3-dihydropyrano[3,2-b]pyridine

To a stirred mixture of PPh$_3$ (67.6 g, 0.258 mol), KOAc (42 g, 0.43 mol), Pd(OAc)$_2$ (1.94 g, 8.6 mmol) and Et$_4$NCl (28.6 g, 0.172 mmol), was added 2,6-dibromo-3-(but-3-enyloxy)pyridine (26.4 g, 0.086 mol) in anhydrous DMF (300 mL). The mixture was heated at 105° C. for 18 hours. After cooling to ambient temperature, the mixture was dissolved in Ethyl acetate, washed with water and brine, dried over Na$_2$SO$_4$, and concentrated in vacuo. The crude product was purified by silica gel chromatography (petroleum) to afford the title compound as oil (4.35 g, 22%). $^1$H NMR (400 Mz, DMSO-d$^6$): δ

2.74 (t, J=5.4, 2H); 4.20 (t, J=6, 2H); 5.12 (s, 1H); 5.98 (s, 1H); 7.24 (d, J=7.5, 1H); 7.40 (d, J=7.5, 1H).

Step d: 4-methylene-6-[4-methyl-2-(3-pyridyl)thiazol-5-yl]-2,3-dihydropyrano[3,2-b]pyridine To a stirred mixture of $Pd_2(dba)_3$ (270 mg, 0.3 mmol), xantphos (870 mg, 1.5 mmol), $K_2CO_3$ (1.52 g, 11 mmol) and 3-(4-methylthiazol-2-yl)pyridine (1.76 g, 10 mmol) in a sealed tube was added 6-bromo-4-methylene-2,3-dihydropyrano[3,2-b]pyridine (2.49 g, 11 mmol) in 1,4-dioxance (30 mL). The mixture was stirred at 120° C. for 18 hours. The mixture was diluted with Ethyl acetate and $H_2O$, the organic layer was washed with brine and water, dried over $Na_2SO_4$, and concentrated in vacuo. The crude product was purified by silica gel chromatography (petroleum/Ethyl acetate=3/1) to give the title compound as red solid (710 mg, 22%). $^1H$ NMR (400 Mz, DMSO-d$^6$): δ: 2.69 (s, 3H); 2.81 (t, J=6, 2H); 4.25 (t, J=5.1, 2H); 5.16 (s, 1H); 6.16 (s, 1H); 7.38 (d, J=8.7, 1H); 7.55-7.50 (m, 1H); 7.6 (d, J=8.7, 1H); 8.31-8.27 (m, 1H); 8.66-8.64 (m, 1H); 9.12 (s, 1H).

Step e: 4-(hydroxymethyl)-6-[4-methyl-2-(3-pyridyl)thiazol-5-yl]-2,3-dihydropyrano[3,2-b]pyridin-4-ol AD-mix-alpha (15.7 g, 1.44 g/mmol) was added to t-BuOH/$H_2O$ (60 mL/60 mL), stirred at ambient temperature for 5 min. $MeSO_2NH_2$ (1.06 g, 11.12 mmol) was added to the reaction mixture. The mixture was cooled with ice, 4-methylene-6-[4-methyl-2-(3-pyridyl)thiazol-5-yl]-2,3-dihydropyrano[3,2-b]pyridine (3.5 g, 10.9 mmol) in THF (35 mL) was added slowly to the above solution. Sodium sulfite (17 g) was added. After 15 min at 0° C., the ice bath was removed and the reaction mixture was stirred at ambient temperature for 45 min. The mixture was diluted with DCM (100 mL) and $H_2O$ (100 mL) and the two layers were separated. The organic layer was washed with brine, dried over $Na_2SO_4$, filtered and concentrated, which was used directly for the next step.

Step f: 6-[4-methyl-2-(3-pyridyl)thiazol-5-yl]-2,3-dihydropyrano[3,2-b]pyridin-4-one (Compound 7.004)

The crude 4-(hydroxymethyl)-6-[4-methyl-2-(3-pyridyl)thiazol-5-yl]-2,3-dihydropyrano[3,2-b]pyridin-4-ol from step e was dissolved in a 1:1 mixture of dioxane (40 mL) and $H_2O$ (40 mL), and sodium periodate (2.22 g, 10.76 mmol) was added. The reaction mixture was stirred at ambient temperature for 1 h. The reaction mixture was diluted with dichloromethane (50 mL) and $H_2O$ (50 mL) and the two layers were separated. The organic layer was dried over $Na_2SO_4$, filtered and concentrated. The resulting residue was purified by silica gel chromatography ($CH_2Cl_2$/MeOH=100/1) to afford the title compound as a yellow solid (1.7 g, two-step yield: 48%). $^1H$ NMR (400 Mz, $CDCl_3$): 2.76 (s, 3H); 3.02 (t, J=6.6, 2H); 4.66 (t, J=6.9, 2H); 7.49 (d, J=9, 1 H); 7.62-7.58 (m, 1H); 7.75 (d, J=8.7, 1 H); 8.45 (d, J=7.8, 1 H); 8.71 (d, J=3.9, 1H); 9.28 (s, 1H).

Step g: N-methoxy-6-[4-methyl-2-(3-pyridyl)thiazol-5-yl]-2,3-dihydropyrano[3,2-b]pyridin-4-imine (Compound 1.032)

6-[4-methyl-2-(3-pyridyl)thiazol-5-yl]-2,3-dihydropyrano[3,2-b]pyridin-4-one (100 mg, 0.31 mmol), compound H2N—OH.HCl (51 mg, 0.62 mmol) and KOAc (61 mg, 0.62 mmol) were suspended in methanol (3 mL) under $N_2$. The reaction mixture was refluxed for 18 hours and purified by chromatography on silica (Ethyl acetate) to get the pure compound as yellow solid (84 mg, 78%). $^1H$ NMR (400 Mz, $CDCl_3$): 2.68 (s, 3H); 2.97 (t, 2H); 4.00 (s, 3H); 4.28 (t, 2H); 7.55-7.46 (m, 2H); 7.72-7.69 (m, 1H); 8.231-8.29 (m, 2H); 8.66-8.65 (m, 1H); 9.13 (s, 1H). Mpt 148-149° C.

Example P6

N-methoxy-2-[4-methyl-2-(3-pyridyl)thiazol-5-yl]-5,6-dihydrothiopyrano[3,2-d]thiazol-7-imine (Compound 3.050)

Step a: methyl 3-(2-aminothiazol-5-yl)sulfanylpropanoate $K_2CO_3$ (14.0 g, 100 mmol) was added to a solution of 5-bromothiazol-2-amine hydrobromide (13.0 g, 50 mmol) in 90 ml of dry DMF at 0° C. under nitrogen. After 0.5 h, methyl 3-sulfanylpropanoate (6.0 g, 50 mmol) was added dropwise to the mixture over the course of 30 min and stirred at ambient temperature for 48 h. Then the mixture was diluted with 500 ml of water and extracted with TBME. The combined organic layers were dried over sodium sulfate, filtered and concentrated in vacuum. The residue was purified by column chromatography on silica gel to give the title compound (7.6 g, 70% yield) $^1H$ NMR (400 Mz, $CDCl_3$) δ2.53 (t, 2H), 2.75 (t, 2H), 3.58 (s, 3H), 7.25 (s, 1H).

Step b: methyl 3-[2-(tert-butoxycarbonylamino)thiazol-5-yl]sulfanylpropanoate $Boc_2O$ (12.0 g, 55.0 mmol) was added dropwise to the mixture of methyl 3-(2-aminothiazol-5-yl)sulfanylpropanoate (9.0 g, 41.2 mmol), $Et_3N$ (12 ml, 86.7 mmol) and DMAP (1.2 g, 10.0 mmol) in 45 ml of $CH_2Cl_2$ at 0° C. under nitrogen. After the addition, the mixture was stirred at ambient temperature for 18 hours and directly concentrated in vacuo. The residue was purified by column chromatography on silica gel to give the title compound (9.0 g, 68% yield) $^1H$ NMR (400 Mz, $CDCl_3$) δ1.58 (s, 9H), 2.62 (t, 2H), 2.92 (t, 2H), 3.68 (s, 3H), 7.35 (s, 1H).

Step c: 3-[2-(tert-butoxycarbonylamino)thiazol-5-yl]sulfanylpropanoic acid

Methyl 3-[2-(tert-butoxycarbonylamino)thiazol-5-yl]sulfanylpropanoate (9.0 g, 28.3 mmol) was dissolved in THF/$H_2O$ (3:1, 200 ml) and LiOH (1.4 g, 57.0 mmol) and the reaction mixture stirred at ambient temperature for 18 hours. The solvent was evaporated under vacuum then diluted with water and acidified with 1 M HCl to pH (4~5). The solid formed was filtered, and washed with water and dried to give the title compound as a yellow solid (7.0 g, 80% yield) $^1H$ NMR (400 Mz, $CDCl_3$) δ1.57 (s, 9H), 2.69 (t, 2H), 2.98 (t, 2H), 7.33 (s, 1H).

Step d: 2-amino-5,6-dihydrothiopyrano[3,2-d]thiazol-7-one

3-[2-(tert-butoxycarbonylamino)thiazol-5-yl]sulfanylpropanoic acid (300 mg, 1.0 mmol) was dissolved in polyphosphoric acid (3.08 g, 14 mmol) and heated at 60~80° C. for 2 hours. The reaction mixture was diluted with ice-cold water and neutralized with NaHCO₃ to pH (8~9) and the solid formed, filtered and washed with water and dried to give the title compound a yellow solid (150 mg, 80% yield) $^1$H NMR (400 Mz, d$^6$-DMSO) δ2.67 (t, 2H), 3.34 (t, 2H), 7.18 (s, 2H).

Step e:
2-bromo-5,6-dihydrothiopyrano[3,2-d]thiazol-7-one

To a stirred solution of 2-amino-5,6-dihydrothiopyrano[3,2-d]thiazol-7-one (160 mg, 0.86 mmol) in MeCN (15 ml) was added CuBr₂ (200 mg, 0.90 mmol) and tert-butyl nitrite (160 mg, 1.36 mmol). After stirring at ambient temperature for 18 hours, the reaction mixture was poured into 10% of HCl (10 ml), and extracted with Ethyl acetate. The combined organic layers were dried over sodium sulfate, filtered and concentrated in vacuo. The residue was purified by column chromatography on silica gel to give the title compound (150 mg, 70% yield). $^1$H NMR (400 Mz, CDCl₃): 2.96 (t, 2H), 3.40 (t, 2H). ESI-MS: 251 (M+1).

Step f: 2-[4-methyl-2-(3-pyridyl)thiazol-5-yl]-5,6-dihydrothiopyrano[3,2-d]thiazol-7-one (compound 7.011)

Tri-n-butyl-[4-methyl-2-(3-pyridyl)thiazol-5-yl]stannane (560 mg, 1.2 mmol, prepared as described previously) and 2-bromo-5,6-dihydrothiopyrano[3,2-d]thiazol-7-one (300 mg, 1.20 mmol), Tris(dibenzylideneacetone)dipalladium(0) (54 mg, 0.06 mmol) and Tri(2-furyl)phosphine (54 mg, 0.23 mmol) were dissolved in 10 ml of dioxane and placed in a steel tube. The mixture were evacuated, flushed with N₂ 3 times and heated at 100° C. for 18 hours. After cooling to ambient temperature, the mixture was filtered and the filtrate was concentrated in vacuo. The residue was purified with chromatography (Ethyl acetate: Petroleum ether=2/1) to give the title compound (83 mg, 20% yield). $^1$H NMR (400 Mz, CDCl₃): δ2.79 (s, 3H), 3.04 (t, 2H), 3.46 (t, 2H), 7.43-7.45 (m, 1H), 8.43 (d, 1H), 8.69 (d, 1H), 9.20 (s, 1H).

Step g: N-methoxy-2-[4-methyl-2-(3-pyridyl)thiazol-5-yl]-5,6-dihydrothiopyrano[3,2-d]thiazol-7-imine Compound 3.050

2-[4-methyl-2-(3-pyridyl)thiazol-5-yl]-5,6-dihydrothiopyrano[3,2-d]thiazol-7-one (150 mg, 0.43 mmol), O-Methylhydroxylamine Hydrochloride (83 mg, 0.86 mmol) and KOAc (86 mg, 0.87 mmol) were suspended in methanol (5 mL) under N₂. The reaction mixture was refluxed overnight, then cooled to ambient temperature, filtered and the filtrate was concentrated in vacuo. The residue was purified by chromatography on silica (Ethyl acetate: Petroleum ether=1:1) to give the title compound as a yellow solid (50 mg, 30%). $^1$H NMR (400 Mz, CDCl₃): δ2.75 (s, 3H), 3.14-3.17 (m, 4H), 4.08 (s, 3H), 7.40-7.43 (m, 1H), 8.24 (d, 1H), 8.67 (d, 1H), 9.18 (s, 1H). ESI-MS(+): 375 (M+H)⁺, 397 (M+Na)⁺.

In the drawings, free radicals signify a methyl group. Double bonds without substituents at the free radicals are substituted by hydrogen. For example, compound No 1.005

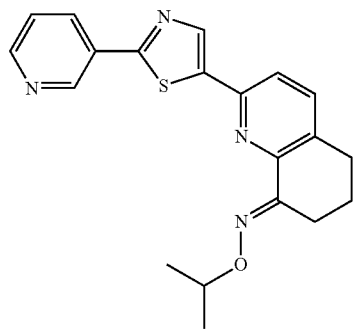
(compound No. 1.005)

can also be drawn as

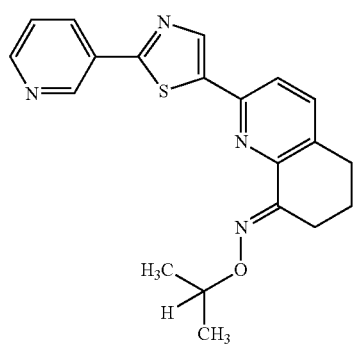
(compound No. 1.005)

Compound 1.006

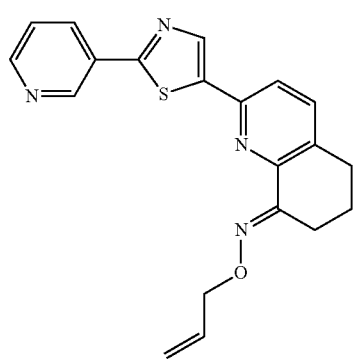
(compound No. 1.006)

can also be drawn as

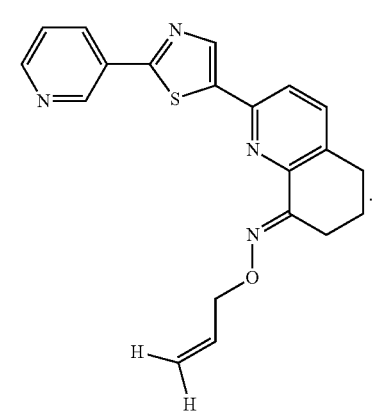
(compound 1.006)

TABLE 1
Examples of compound of formula (Iaa)
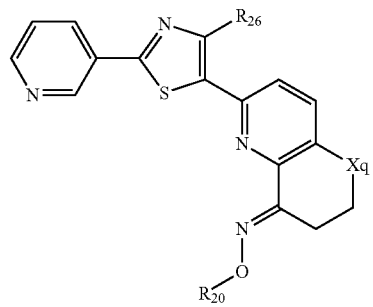
Formula Iaa
| Comp. No. | R$_{26}$ | R$_{20}$ | Xq | Structure | Phys. Data LCMS/NMR or Mpt |
|---|---|---|---|---|---|
| 1.001 | H | H | CH$_2$ | 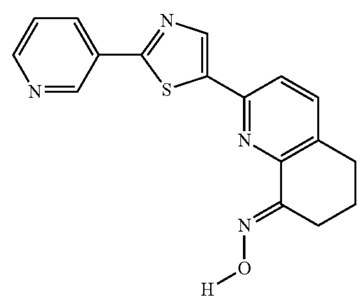 | |
| 1.002 | H | CH$_3$ | CH$_2$ | 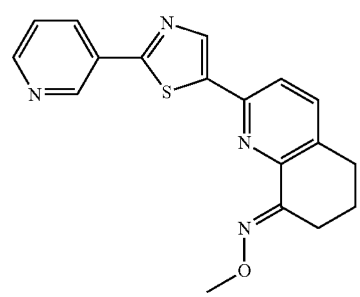 | Mpt 157-159° C. |
| 1.003 | H | CH$_3$CH$_2$ | CH$_2$ | 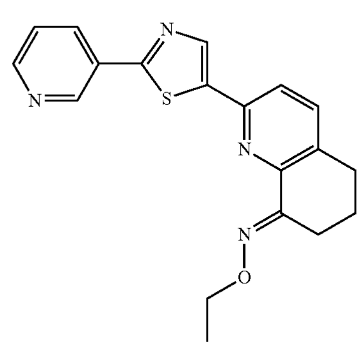 | $^1$H NMR (400 MHz, CHLOROFORM-d) δ ppm: 1.42 (t, 3H); 1.91 (m, 2H); 2.83 (t, 2H); 2.90 (t, 2H); 4.48 (q, 2H); 7.43 (dd, 1H); 7.55 (d, 1H); 7.62 (d, 1H); 8.32 (m, 2H); 8.7 (s, 1H); 9.68 (s, 1H). |

TABLE 1-continued
Examples of compound of formula (Iaa)
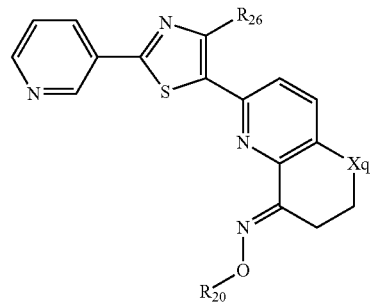
Formula Iaa
| Comp. No. | $R_{26}$ | $R_{20}$ | Xq | Structure | Phys. Data LCMS/NMR or Mpt |
|---|---|---|---|---|---|
| 1.004 | H | $CH_3CH_2CH_2$ | $CH_2$ | 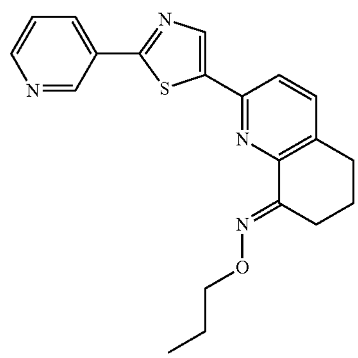 | |
| 1.005 | H | $(CH_3)_2CH$ | $CH_2$ | 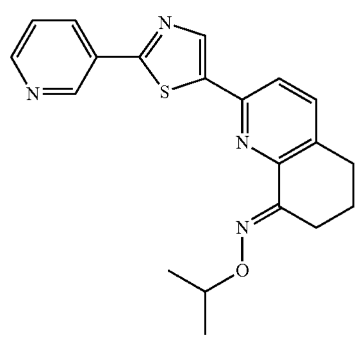 | |
| 1.006 | H | $CH_2=CH_2$ | $CH_2$ | 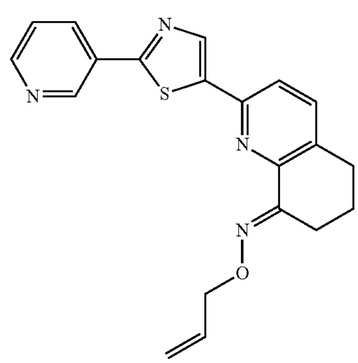 | |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.007 | H | H | O | | |
| 1.008 | H | $CH_3$ | O | | |
| 1.009 | H | $CH_3CH_2$ | O | | |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.010 | H | $CH_3CH_2CH_2$ | O | 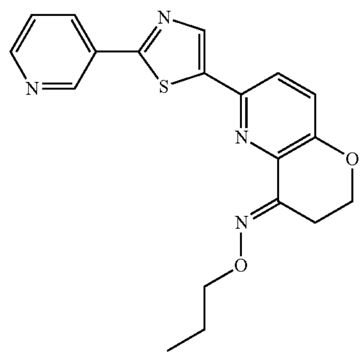 [SMILES: CCCO/N=C1\CCOc2ccc(-c3cnc(-c4cccnc4)s3)nc21] | |
| 1.011 | H | $(CH_3)_2CH$ | O | 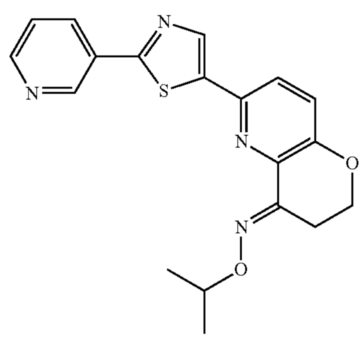 [SMILES: CC(C)O/N=C1\CCOc2ccc(-c3cnc(-c4cccnc4)s3)nc21] | |
| 1.012 | H | $CH_2=CH_2$ | O | 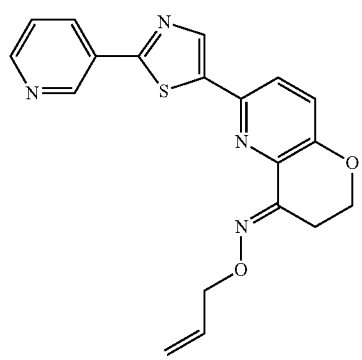 [SMILES: C=CCO/N=C1\CCOc2ccc(-c3cnc(-c4cccnc4)s3)nc21] | |

TABLE 1-continued

Examples of compound of formula (Iaa)

Formula Iaa

| Comp. No. | R$_{26}$ | R$_{20}$ | Xq | Structure | Phys. Data LCMS/NMR or Mpt |
|---|---|---|---|---|---|
| 1.013 | H | H | N—CH$_3$ | 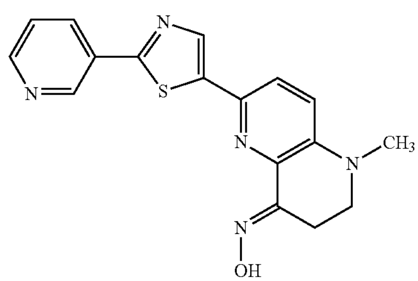 | |
| 1.014 | H | CH$_3$ | N—CH$_3$ | 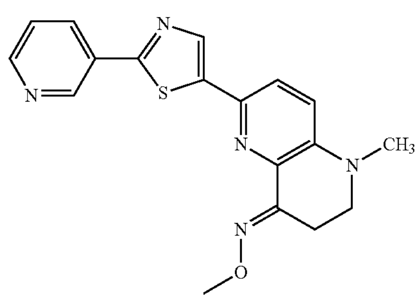 | |
| 1.015 | H | CH$_3$CH$_2$ | N—CH$_3$ | 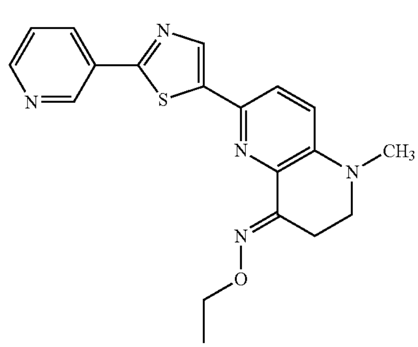 [SMILES: CCO/N=C1\CCN(C)c2ccc(-c3cnc(-c4cccnc4)s3)nc21] | |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.016 | H | CH$_3$CH$_2$CH$_2$ | N—CH$_3$ | 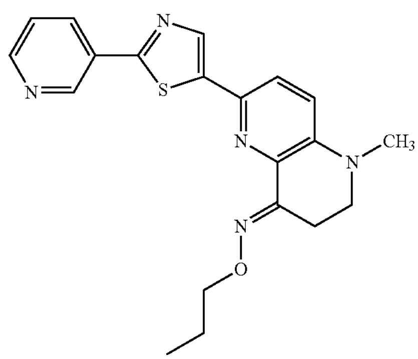 [SMILES: CCCO/N=C1\CCN(C)c2ccc(-c3cnc(-c4cccnc4)s3)nc21] | |
| 1.017 | H | (CH$_3$)$_2$CH | N—CH$_3$ | 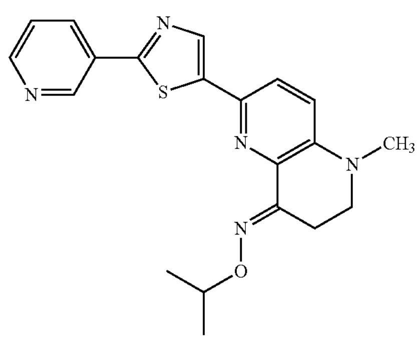 [SMILES: CC(C)O/N=C1\CCN(C)c2ccc(-c3cnc(-c4cccnc4)s3)nc21] | |
| 1.018 | H | CH$_2$C=CH$_2$ | N—CH$_3$ | 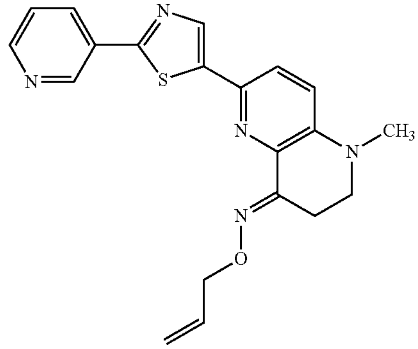 [SMILES: C=CCO/N=C1\CCN(C)c2ccc(-c3cnc(-c4cccnc4)s3)nc21] | |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.019 | H | H | N—SO$_2$CH$_3$ | 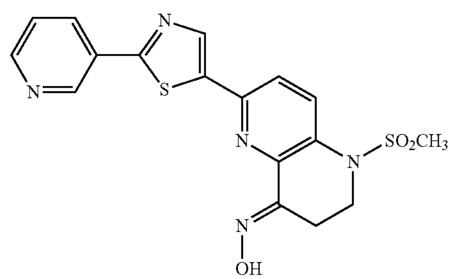 | |
| 1.020 | H | CH$_3$ | N—SO$_2$CH$_3$ | 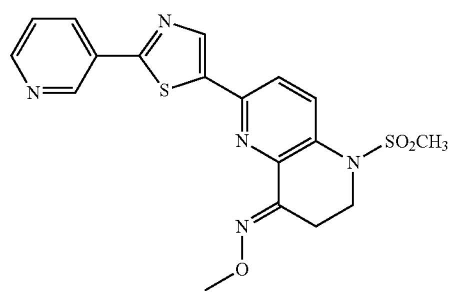 | |
| 1.021 | H | CH$_3$CH$_2$ | N—SO$_2$CH$_3$ | 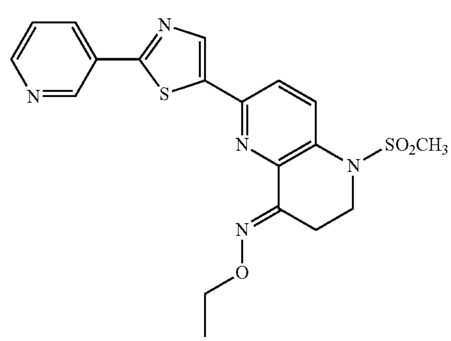 [SMILES: CCO/N=C1\CCN(S(C)(=O)=O)c2ccc(-c3cnc(-c4cccnc4)s3)nc21] | |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.022 | H | $CH_3CH_2CH_2$ | $N-SO_2CH_3$ | 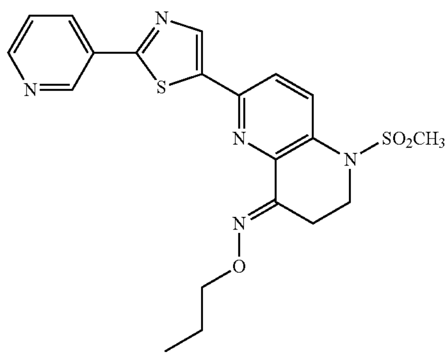 [SMILES: CCCO/N=C1\CCN(S(C)(=O)=O)c2ccc(-c3cnc(-c4cccnc4)s3)nc21] | |
| 1.023 | H | $(CH_3)_2CH$ | $N-SO_2CH_3$ | 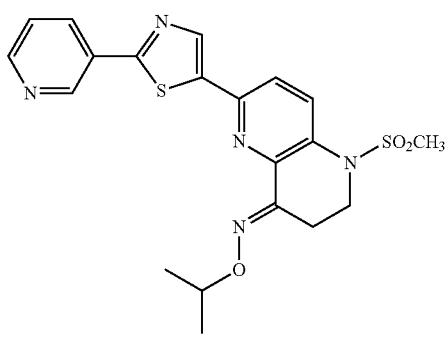 [SMILES: CC(C)O/N=C1\CCN(S(C)(=O)=O)c2ccc(-c3cnc(-c4cccnc4)s3)nc21] | |
| 1.024 | H | $CH_2C=CH_2$ | $N-SO_2CH_3$ | 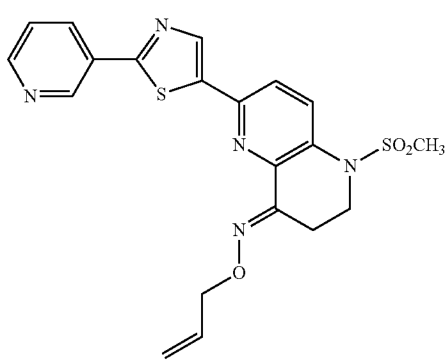 [SMILES: C=CCO/N=C1\CCN(S(C)(=O)=O)c2ccc(-c3cnc(-c4cccnc4)s3)nc21] | |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.025 | $CH_3$ | H | $CH_2$ | 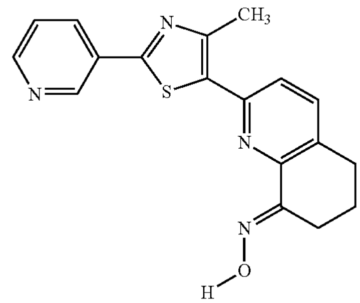 | $^1$H NMR (400 MHz, CHLOROFORM-d) δ ppm 1.92-2.01 (m, 2H); 2.75-2.77 (m, 2H); 2.86 (t, J = 6.0 Hz, 2H); 2.98 (t, J = 6.0 Hz, 2H); 7.52-7.60 (m, 2H); 8.28 (dt, J = 7.79, 1.97 Hz, 1H); 8.65 (dd, J = 4.77, 1.47 Hz, 1H); 9.21 (d, J = 1.47 Hz, 1H). LCMS: 0.83 min, 337 (M + 1). |
| 1.026 | $CH_3$ | $CH_3$ | $CH_2$ | 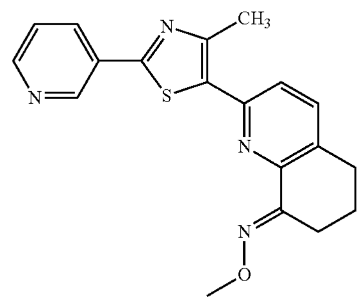 | $^1$H NMR(400 MHz, CHLOROFORM-d) δ ppm 1.85-1.96 (m, 2H); 2.78 (s, 3H); 2.82 (t, J = 6.0 Hz, 2H); 2.87 (t, J = 6.0 Hz, 2H); 4.14 (s, 3H); 7.38 (dd, J = 8.07, 4.77 Hz, 1H); 7.47-7.60 (m, 2H); 8.26 (d, J = 8.07 Hz, 1H); 8.64 (d, J = 4.07 Hz, 1H); 9.19 (s, 1H). LCMS: 0.99 min, 351 (M + 1). |
| 1.027 | $CH_3$ | $CH_3CH_2$ | $CH_2$ | 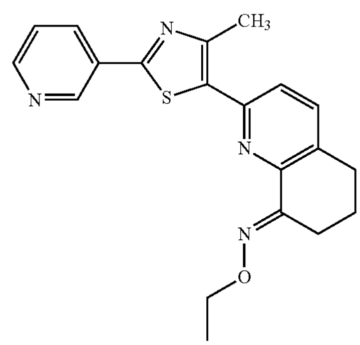 | $^1$H NMR (400 MHz, CHLOROFORM-d) δ ppm 1.39 (t, J = 7.21 Hz, 3H); 1.91 (quin, J = 6.24 Hz, 2H); 2.80 (s, 3H); 2.82 (t, J = 6.60 Hz, 2H); 2.89 (t, J = 6.60 Hz, 2H); 4.41 (q, J = 7.21 Hz, 2H); 7.38 (dd, J = 7.70, 4.40 Hz, 1H) 7.47-7.58 (m, 2H); 8.27 (d, J = 7.70 Hz, 1H); 8.65 |

TABLE 1-continued

Examples of compound of formula (Iaa)

Formula Iaa

| Comp. No. | R26 | R20 | Xq | Structure | Phys. Data LCMS/NMR or Mpt |
|---|---|---|---|---|---|
| | | | | | (d, J = 4.40 Hz, 1H); 9.20 (s, 1H). LCMS: 1.07 min, 365 (M + 1). Mpt 128-130° C. |
| 1.028 | $CH_3$ | $CH_3CH_2CH_2$ | $CH_2$ | 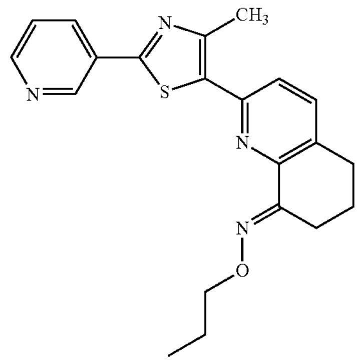 | 1H NMR(400 MHz, CHLOROFORM-d) δ ppm 1.01 (t, J = 7.52 Hz, 3H); 1.80 (m, 3H); 1.91 (quin, J = 6.42 Hz, 3H); 2.80 (s, 3H); 2.84 (t J = 6.42 Hz, 2H); 2.89 (t, J = 6.42 Hz, 3H); 4.32 (t, J = 7.52 Hz, 3H); 7.38 (dd, J = 7.70, 4.40 Hz, 1H); 7.45-7.58 (m, 2H); 8.26 (d, J = 7.70 Hz, 1H); 8.64 (d, J = 4.40 Hz, 1H); 9.19 (s, 1H). LCMS: 1.14 min, 379 (M + 1). |
| 1.029 | $CH_3$ | $(CH_3)_2CH$ | $CH_2$ | 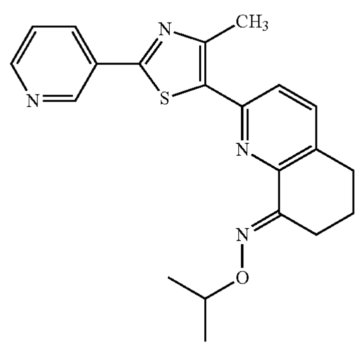 | $^1$H NMR(400 MHz, CHLOROFORM-d) δ ppm 1.38 (d, J = 6.14 Hz, 7H); 1.91 (quin, J = 6.60 Hz, 2H); 2.81 (t, J = 6.60 Hz, 2H); 2.83 (s, 3H); 2.88 (t, J = 6.60 Hz, 2H); 4.65 (m, 1H); 7.39 (dd, J = 8.07, 4.77 Hz, 1H); 7.45-7.57 (m, 2H); 8.27 (d, J = 8.07 Hz, 1H); 8.65 (d, J = 4.77 Hz, 1H); 9.20 (s, 1H). Mpt. 164-168° C. LCMS: 1.15 min, 379 (M + 1). |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.030 | $CH_3$ | $CH_2C{=}CH_2$ | $CH_2$ | 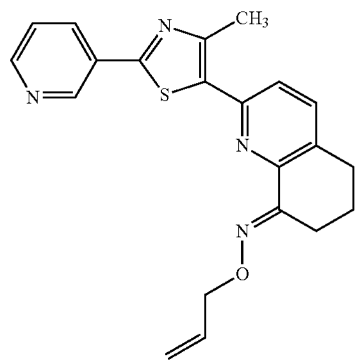 | $^1$H NMR(400 MHz, CHLOROFORM-d) δ ppm 1.91 (quin, J = 6.24 Hz, 2H); 2.80 (s, 3H); 2.81-2.85 (t, J = 6.42 Hz, 2H); 2.91 (t, J = 6.42 Hz, 2H); 4.87 (d, J = 5.50 Hz, 2H) 5.27 (d, J = 10.27 Hz, 1H); 5.40 (d, J = 17.24 Hz, 1H); 6.05-6.18 (m, 1H); 7.38 (dd, J = 8.07, 4.95 Hz, 1H); 7.47-7.57 (m, 2H); 8.26 (d, J = 8.07 Hz, 1H); 8.65 (d, J = 4.40 Hz, 1H); 9.19 (s, 1H). LCMS: 1.09 min, 377 (M + 1). |
| 1.031 | $CH_3$ | H | O | 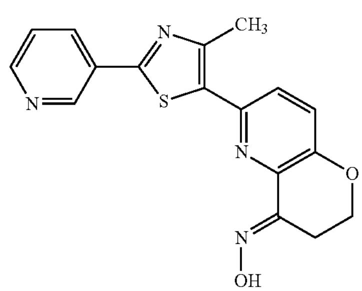 | Mpt 240-243° C. |
| 1.032 | $CH_3$ | $CH_3$ | O | 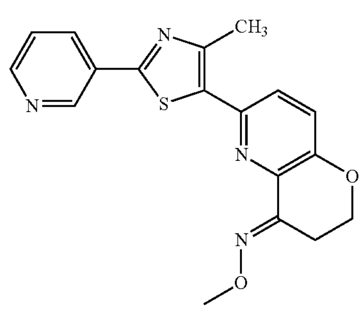 | $^1$H NMR (400 MHz, CHLOROFORM-d) δ ppm: 2.68 (s, 3H); 2.97 (t, 2H); 4.00 (s, 3H); 4.28 (t, 2H); 7.55-7.46 (m, 2H); 7.72-7.69 (m, 1H); 8.231-8.29 (m, 2H); 8.66-8.65 (m, 1H); 9.13 (s, 1H). Mpt 148-149° C. |

TABLE 1-continued
Examples of compound of formula (Iaa)
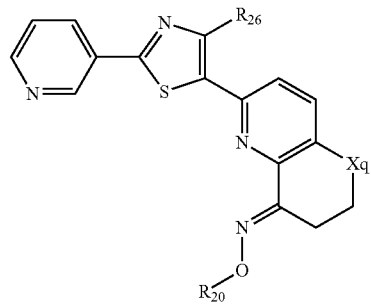
Formula Iaa
| Comp. No. | $R_{26}$ | $R_{20}$ | Xq | Structure | Phys. Data LCMS/NMR or Mpt |
|---|---|---|---|---|---|
| 1.033 | $CH_3$ | $CH_3CH_2$ | O | | Mpt 80-83° C. |
| 1.034 | $CH_3$ | $CH_3CH_2CH_2$ | O | | |
| 1.035 | $CH_3$ | $(CH_3)_2CH$ | O | | Mpt 143-145° C. |

TABLE 1-continued
Examples of compound of formula (Iaa)
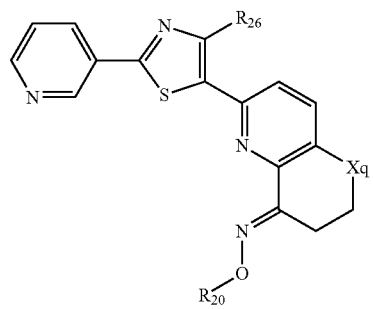
Formula Iaa
| Comp. No. | R$_{26}$ | R$_{20}$ | Xq | Structure | Phys. Data LCMS/NMR or Mpt |
|---|---|---|---|---|---|
| 1.036 | CH$_3$ | CH$_2$C=CH$_2$ | O | 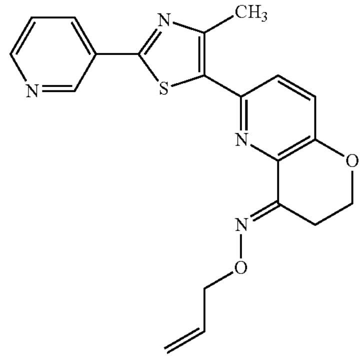 [SMILES: C=CCO/N=C1\CCOc2ccc(-c3sc(-c4cccnc4)nc3C)nc21] | Mpt 98-100° C. |
| 1.037 | CH$_3$ | H | N—CH$_3$ | 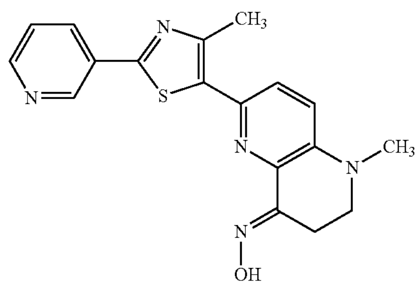 | |
| 1.038 | CH$_3$ | CH$_3$ | N—CH$_3$ | 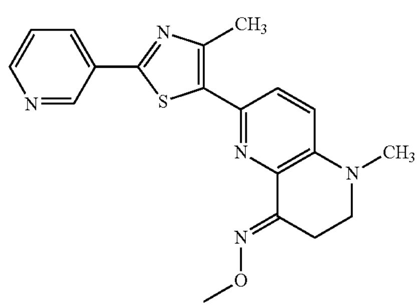 | |

TABLE 1-continued
Examples of compound of formula (Iaa)
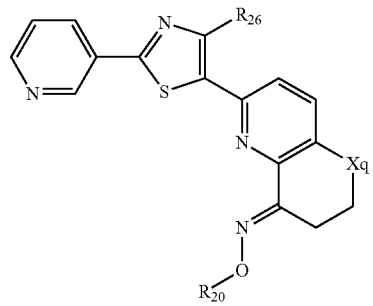
Formula Iaa
| Comp. No. | $R_{26}$ | $R_{20}$ | Xq | Structure | Phys. Data LCMS/NMR or Mpt |
|---|---|---|---|---|---|
| 1.039 | $CH_3$ | $CH_3CH_2$ | N—$CH_3$ | 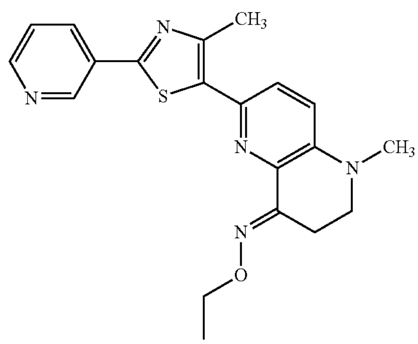 [SMILES: CCO/N=C1\CCN(C)c2ccc(-c3sc(-c4cccnc4)nc3C)nc21] | |
| 1.040 | $CH_3$ | $CH_3CH_2CH_2$ | N—$CH_3$ | 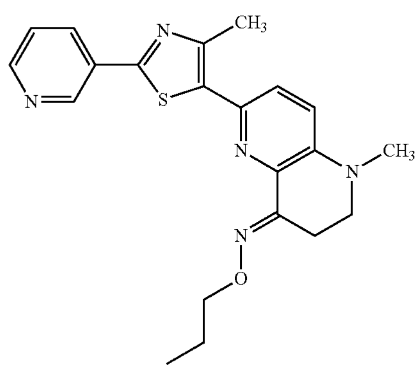 [SMILES: CCCO/N=C1\CCN(C)c2ccc(-c3sc(-c4cccnc4)nc3C)nc21] | |
| 1.041 | $CH_3$ | $(CH_3)CH_2CH_2$ | N—$CH_3$ | 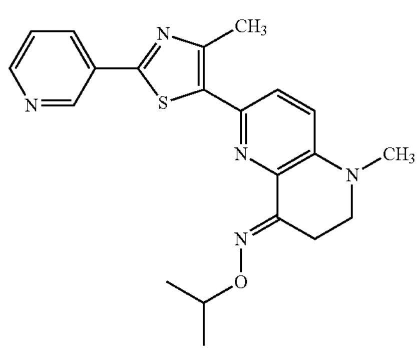 [SMILES: Cc1nc(-c2cccnc2)sc1-c1ccc2c(n1)/C(=N/OC(C)C)CCN2C] | |

TABLE 1-continued
Examples of compound of formula (Iaa)
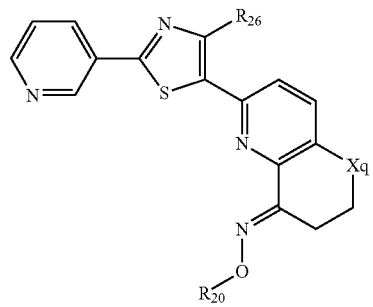
Formula Iaa
| Comp. No. | $R_{26}$ | $R_{20}$ | Xq | Structure | Phys. Data LCMS/NMR or Mpt |
|---|---|---|---|---|---|
| 1.042 | $CH_3$ | $CH_2C=CH_2$ | $N-CH_3$ | 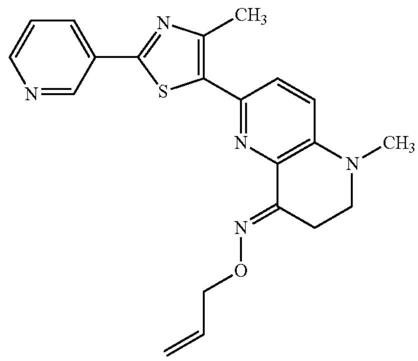 [SMILES: C=CCO/N=C1\CCN(C)c2ccc(-c3sc(-c4cccnc4)nc3C)nc21] | |
| 1.043 | $CH_3$ | H | $N-SO_2CH_3$ | 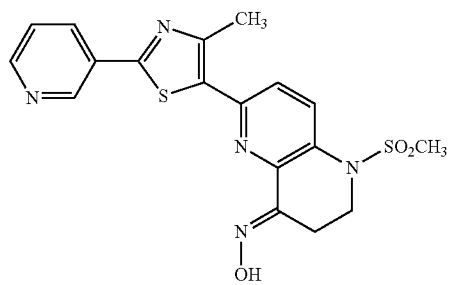 | |
| 1.044 | $CH_3$ | $CH_3$ | $N-SO_2CH_3$ | 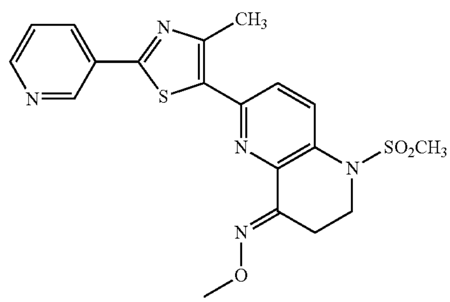 | |

TABLE 1-continued
Examples of compound of formula (Iaa)
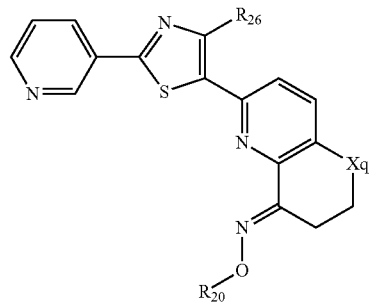
Formula Iaa
| Comp. No. | R26 | R20 | Xq | Structure | Phys. Data LCMS/NMR or Mpt |
|---|---|---|---|---|---|
| 1.045 | CH3 | CH3CH2 | N—SO2CH3 | 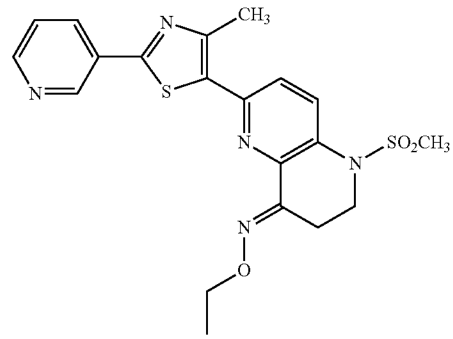 [SMILES: CCO/N=C1\CCN(S(C)(=O)=O)c2ccc(-c3sc(-c4cccnc4)nc3C)nc21] | |
| 1.046 | CH3 | CH3CH2CH2 | N—SO2CH3 | 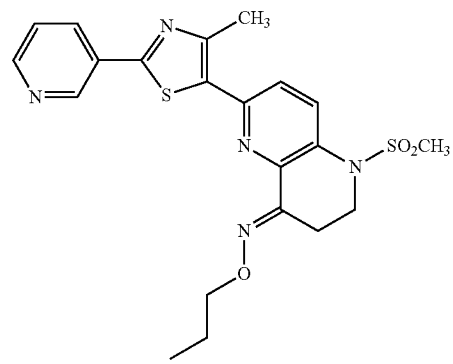 [SMILES: CCCO/N=C1\CCN(S(C)(=O)=O)c2ccc(-c3sc(-c4cccnc4)nc3C)nc21] | |
| 1.047 | CH3 | (CH3)2CH | N—SO2CH3 | 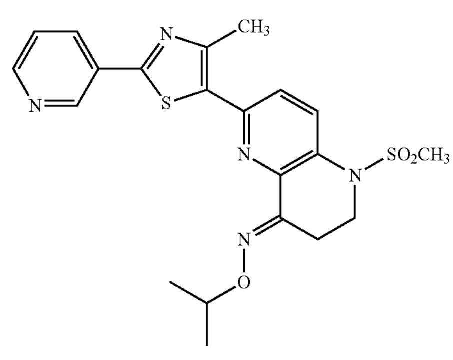 [SMILES: Cc1nc(-c2cccnc2)sc1-c1ccc2c(n1)/C(=N/OC(C)C)CCN2S(C)(=O)=O] | |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.048 | $CH_3$ | $CH_2C{=}CH_2$ | $N{-}SO_2CH_3$ | 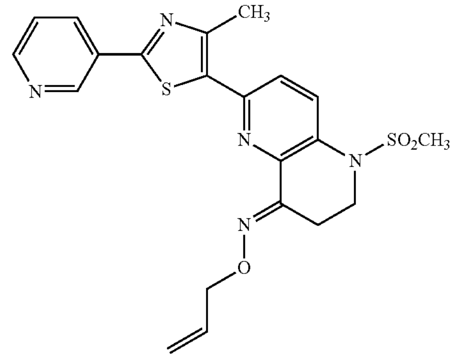 [SMILES: C=CCO/N=C1\CCN(S(C)(=O)=O)c2ccc(-c3sc(-c4cccnc4)nc3C)nc21] | |
| 1.049 | $CH_3$ | $PhCH2CH_2CH_2$ | $CH_2$ | 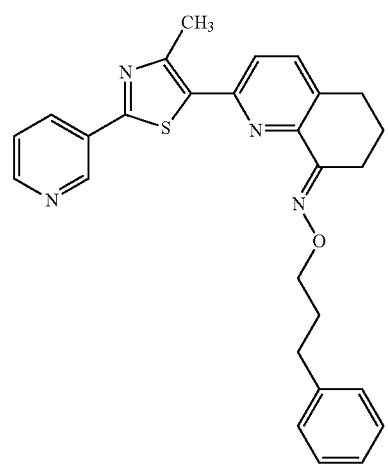 | LCMS: 1.28 min, 455 (M + 1). |
| 1.050 | $CH_3$ | $F2CHCH_2$ | $CH_2$ | 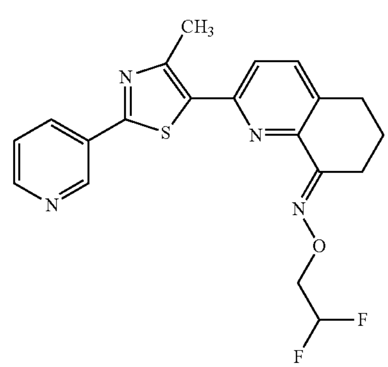 | LCMS: 1.63 min, 401 (M + 1). |

TABLE 1-continued

Examples of compound of formula (Iaa)

Formula Iaa

| Comp. No. | R26 | R20 | Xq | Structure | Phys. Data LCMS/NMR or Mpt |
|---|---|---|---|---|---|
| 1.051 | CH3 | | CH2 | 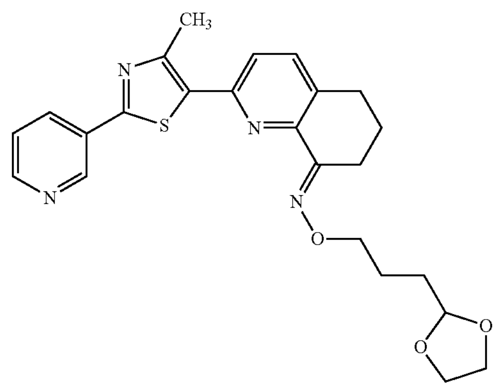 [SMILES: Cc1nc(-c2cccnc2)sc1-c1ccc2c(n1)/C(=N/OCCCC1OCCO1)CCC2] | LCMS: 1.72 min, 451 (M + 1). |
| 1.052 | CH3 | | CH2 | 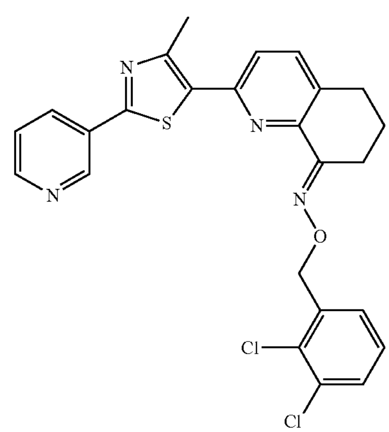 | LCMS: 1.44 min, 409 (M + 1). |
| 1.053 | CH3 | | CH2 | 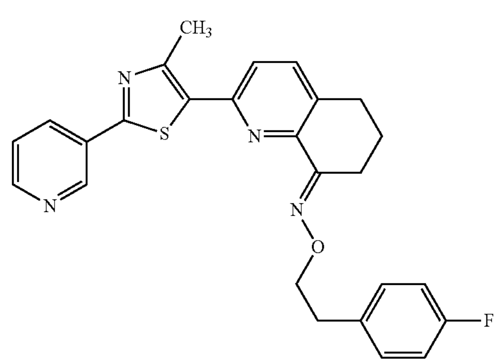 [SMILES: Cc1nc(-c2cccnc2)sc1-c1ccc2c(n1)/C(=N/OCCc1ccc(F)cc1)CCC2] | LCMS: 2.0 min, 459 (M + 1). |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.054 | $CH_3$ | (1-methylpyrrolidin-2-yl)ethyl | $CH_2$ | 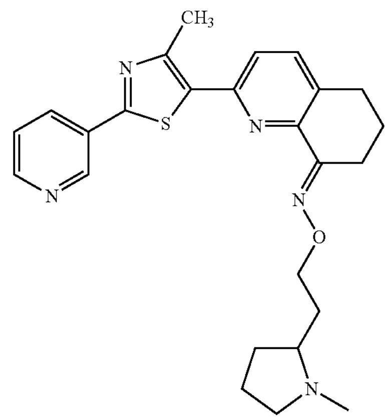 | LCMS: 1.01 min, 448 (M + 1). |
| 1.055 | $CH_3$ | 2-fluorobenzyl | $CH_2$ | 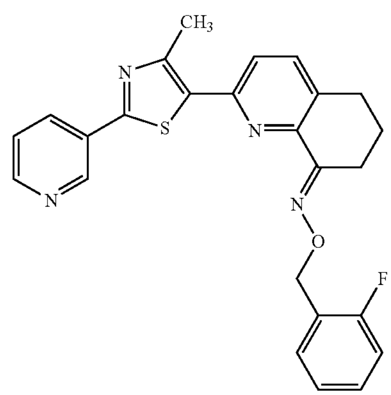 | LCMS: 1.92 min, 445 (M + 1). |
| 1.056 | $CH_3$ | 2-(2-fluorophenyl)ethyl | $CH_2$ | 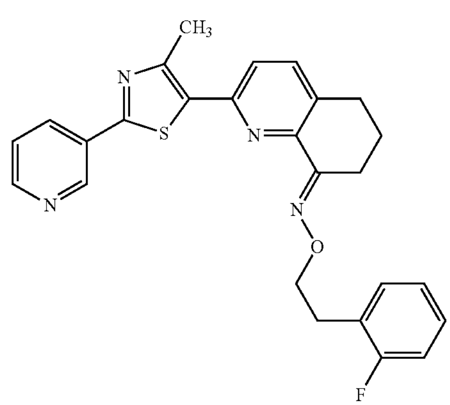 | LCMS: 1.13 min, 459 (M + 1). |

TABLE 1-continued

Examples of compound of formula (Iaa)

Formula Iaa

| Comp. No. | $R_{26}$ | $R_{20}$ | Xq | Structure | Phys. Data LCMS/NMR or Mpt |
|---|---|---|---|---|---|
| 1.057 | $CH_3$ | (3,3,3-trifluoropropyl) | $CH_2$ | 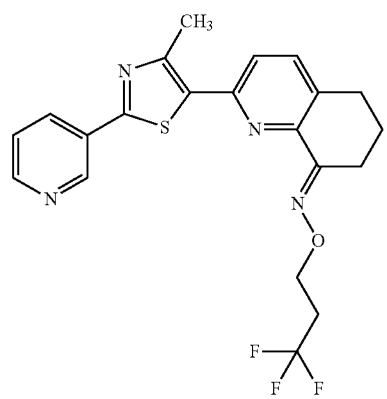 | LCMS: 0.99 min, 433 (M + 1). |
| 1.058 | $CH_3$ | (4-fluorobenzyl) | $CH_2$ | 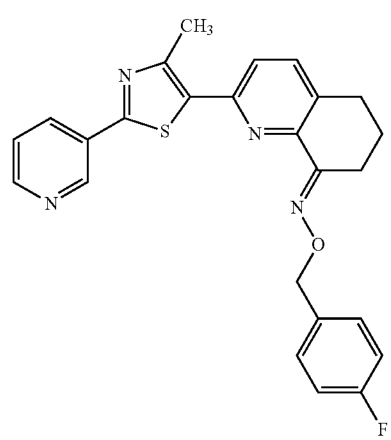 | LCMS: 1.92 min, 445 (M + 1). |

TABLE 1-continued
Examples of compound of formula (Iaa)
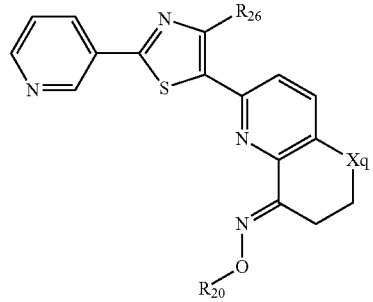
Formula Iaa
| Comp. No. | $R_{26}$ | $R_{20}$ | Xq | Structure | Phys. Data LCMS/NMR or Mpt |
|---|---|---|---|---|---|
| 1.059 | $CH_3$ | morpholinoethyl | $CH_2$ | 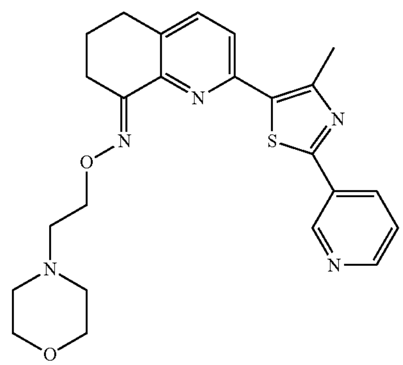 | LCMS: 0.86 min, 450 (M + 1). |
| 1.060 | $CH_3$ | 2-fluoroethyl | $CH_2$ | 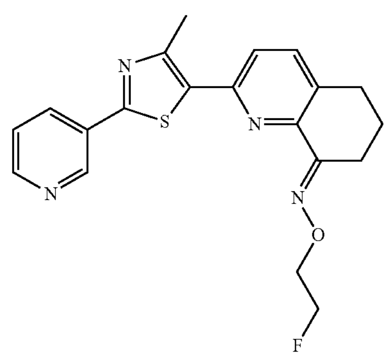 | LCMS: 0.86 min, 383 (M + 1). |
| 1.061 | $CH_3$ | 3,4,4-trifluorobut-3-enyl | $CH_2$ | 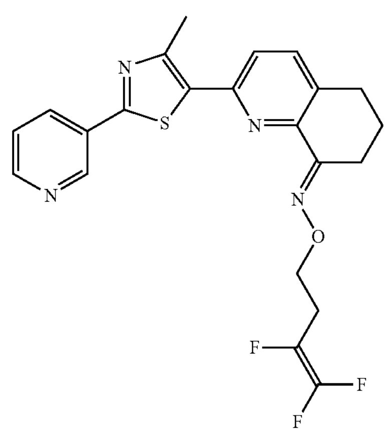 | LCMS: 1.03 min, 444 (M + 1). |

TABLE 1-continued
Examples of compound of formula (Iaa)
Formula Iaa
| Comp. No. | $R_{26}$ | $R_{20}$ | Xq | Structure | Phys. Data LCMS/NMR or Mpt |
|---|---|---|---|---|---|
| 1.062 | $CH_3$ | 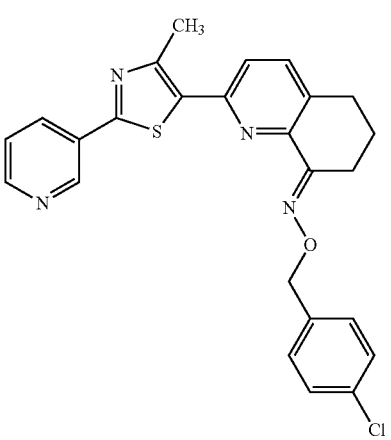 | $CH_2$ | 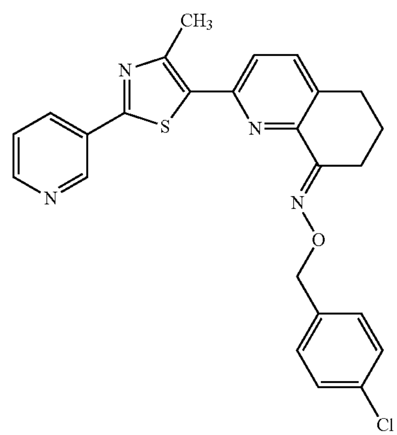 | LCMS: 2.05 min, 461 (M + 1). |
| 1.063 | $CH_3$ | 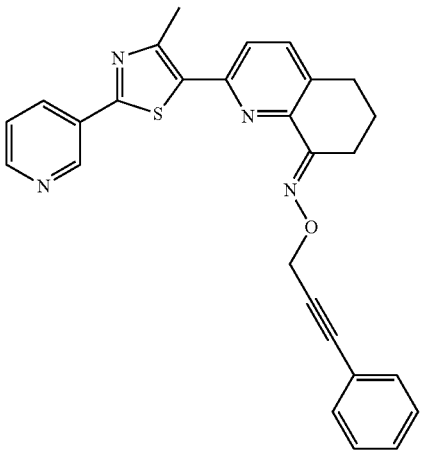 | $CH_2$ | 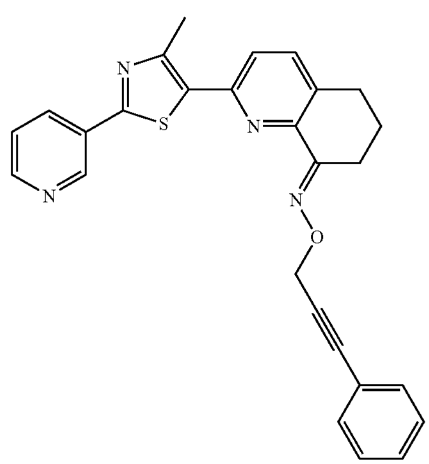 | LCMS: 1.98 min, 451 (M + 1). |

TABLE 1-continued

Examples of compound of formula (Iaa)

Formula Iaa

| Comp. No. | R$_{26}$ | R$_{20}$ | Xq | Structure | Phys. Data LCMS/NMR or Mpt |
|---|---|---|---|---|---|
| 1.064 | CH$_3$ | (cyclohexylmethyl) | CH$_2$ | (structure) | LCMS: 2.27 min, 433 (M + 1). |
| 1.065 | CH$_3$ | (2-(4-fluorophenylthio)ethyl) | CH$_2$ | (structure) | LCMS: 1.71 min, 491 (M + 1). |

TABLE 1-continued

Examples of compound of formula (Iaa)

Formula Iaa

| Comp. No. | R$_{26}$ | R$_{20}$ | Xq | Structure | Phys. Data LCMS/NMR or Mpt |
|---|---|---|---|---|---|
| 1.066 | CH$_3$ | (1,3-dioxolan-2-ylmethyl) | CH$_2$ | 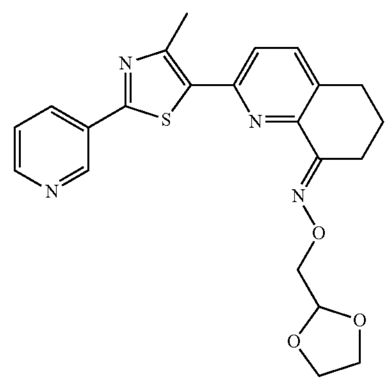 | LCMS: 1.44 min, 423 (M + 1). |
| 1.067 | CH$_3$ | (3,5-bis(trifluoromethyl)benzyl) | CH$_2$ | 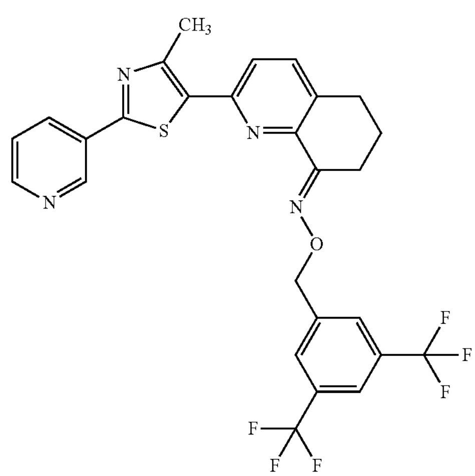 | LCMS: 0.99 min, 563 (M + 1). |

TABLE 1-continued

Examples of compound of formula (Iaa)

Formula Iaa

| Comp. No. | R$_{26}$ | R$_{20}$ | Xq | Structure | Phys. Data LCMS/NMR or Mpt |
|---|---|---|---|---|---|
| 1.068 | CH$_3$ | benzyl | CH$_2$ | 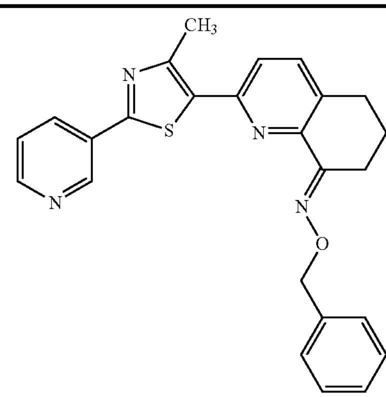 | LCMS: 1.90 min, 427 (M + 1). |
| 1.069 | CH$_3$ | 2-methylbutyl | CH$_2$ | 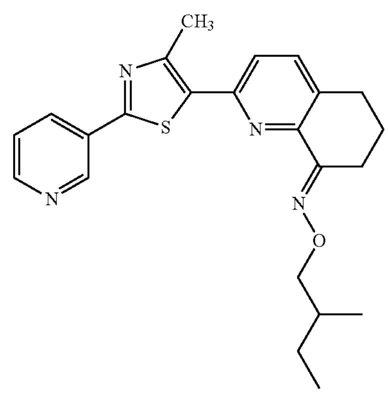 | LCMS: 1.09 min, 407 (M + 1). |
| 1.070 | CH$_3$ | 4,4,4-trifluorobutyl | CH$_2$ | 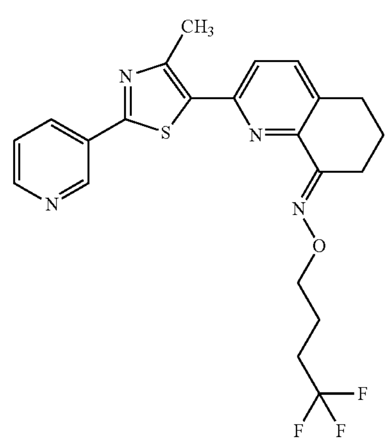 | LCMS: 1.02 min, 447 (M + 1). |

TABLE 1-continued

Examples of compound of formula (Iaa)

| Comp. No. | R$_{26}$ | R$_{20}$ | Xq | Structure | Phys. Data LCMS/NMR or Mpt |
|---|---|---|---|---|---|
| 1.071 | CH$_3$ | 6-chloropyridin-3-ylmethyl | CH$_2$ | 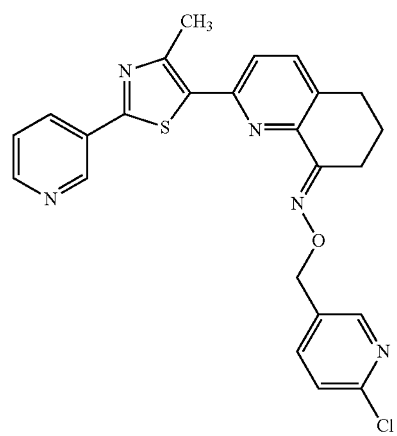 | LCMS: 1.75 min, 462 (M + 1). |
| 1.072 | CH$_3$ | 2-phenylethyl | CH$_2$ | 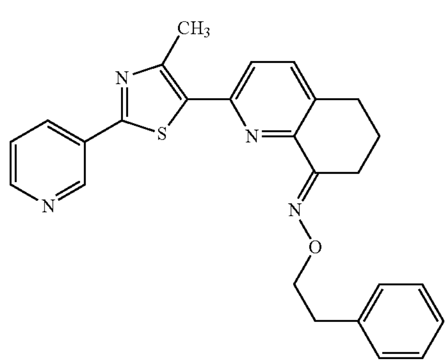 | LCMS: 2.0 min, 441 (M + 1). |

TABLE 1-continued

Examples of compound of formula (Iaa)

Formula Iaa

| Comp. No. | R26 | R20 | Xq | Structure | Phys. Data LCMS/NMR or Mpt |
|---|---|---|---|---|---|
| 1.073 | CH3 | (1-methyl-5-methylthio-1,2,4-triazol-3-yl)methyl | CH2 | 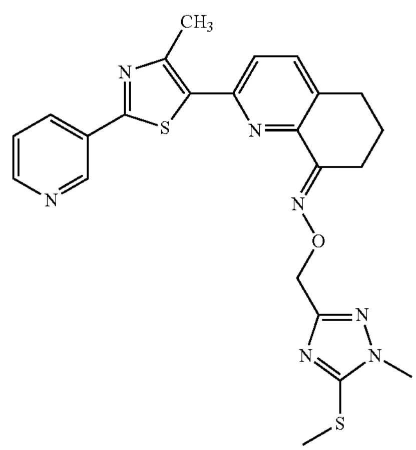 [SMILES: CSc1nc(CO/N=C2\CCCc3ccc(-c4sc(-c5cccnc5)nc4C)nc32)nn1C] | LCMS: 1.43 min, 478 (M + 1). |
| 1.074 | CH3 | (2-chloro-4-fluorobenzyl) | CH2 | 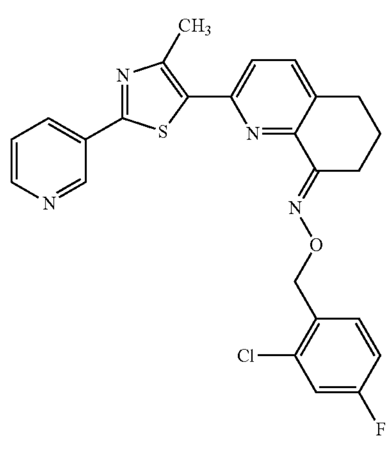 [SMILES: Cc1nc(-c2cccnc2)sc1-c1ccc2c(n1)/C(=N/OCc1ccc(F)cc1Cl)CCC2] | LCMS: 2.08 min, 479 (M + 1). |

TABLE 1-continued

Examples of compound of formula (Iaa)

Formula Iaa

| Comp. No. | R₂₆ | R₂₀ | Xq | Structure | Phys. Data LCMS/NMR or Mpt |
|---|---|---|---|---|---|
| 1.075 | CH₃ | (3-methylpentan-2-yl) | CH₂ | 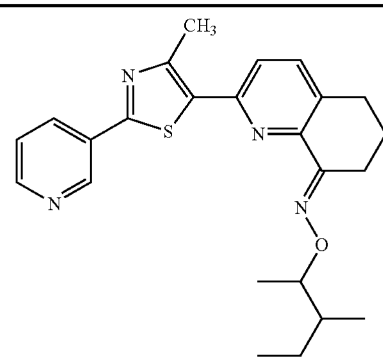 | LCMS: 1.52 min, 421 (M + 1). |
| 1.076 | CH₃ | (3-fluorobenzyl) | CH₂ | 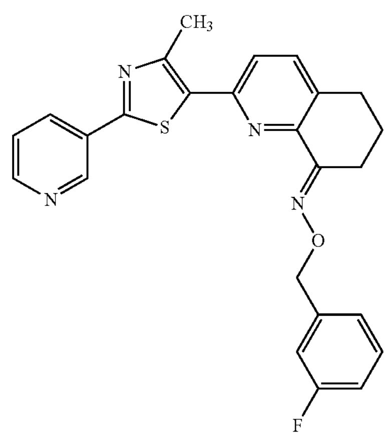 | LCMS: 1.78 min, 445 (M + 1). |
| 1.077 | CH₃ | (tetrahydropyran-2-ylmethyl) | CH₂ | 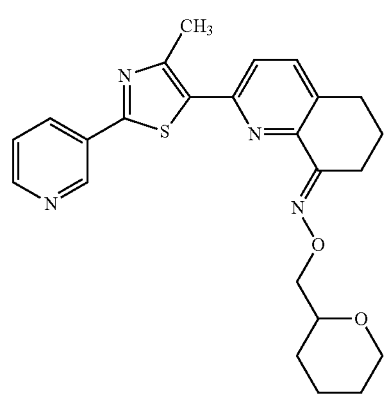 | LCMS: 1.93 min, 435 (M + 1). |

TABLE 1-continued

Examples of compound of formula (Iaa)

Formula Iaa

| Comp. No. | R$_{26}$ | R$_{20}$ | Xq | Structure | Phys. Data LCMS/NMR or Mpt |
|---|---|---|---|---|---|
| 1.078 | CH$_3$ | (2-(4,5-dimethyl-1,3-dioxolan-2-yl)methyl) | CH$_2$ | 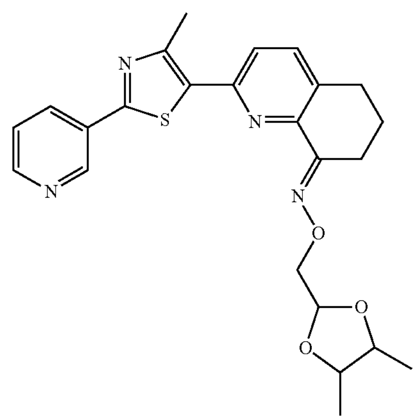 | LCMS: 1.86 min, 451 (M + 1). |
| 1.079 | CH$_3$ | (2,2-difluoropropyl) | CH$_2$ | 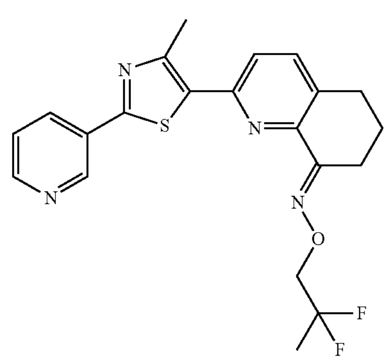 | LCMS: 1.15 min, 415 (M + 1). |

TABLE 2
Examples of compound of formula (Ibb)
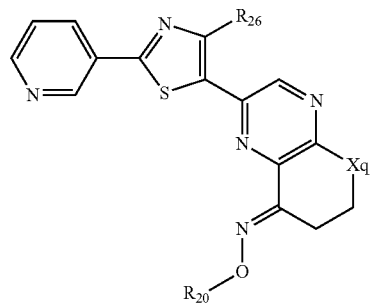
Formula Ibb
| Comp. No. | $R_{26}$ | $R_{20}$ | Xq | Structure | Phys. Data LCMS/NMR or Mpt |
|---|---|---|---|---|---|
| 2.001 | H | H | $CH_2$ | | |
| 2.002 | H | $CH_3$ | $CH_2$ | | |
| 2.003 | H | $CH_3CH_2$ | $CH_2$ | | |

TABLE 2-continued

Examples of compound of formula (Ibb)

Formula Ibb

| Comp. No. | $R_{26}$ | $R_{20}$ | Xq | Structure | Phys. Data LCMS/NMR or Mpt |
|---|---|---|---|---|---|
| 2.004 | H | $CH_3CH_2CH_2$ | $CH_2$ | 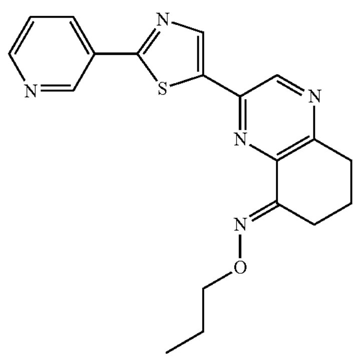 | |
| 2.005 | H | $(CH_3)_2CH$ | $CH_2$ | 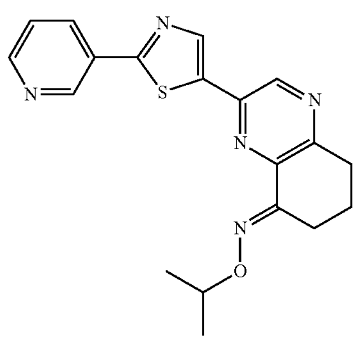 | |
| 2.006 | H | $CH_2C{=}CH_2$ | $CH_2$ | 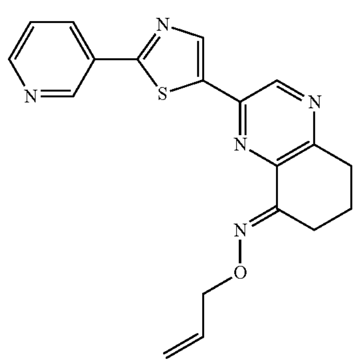 | |

TABLE 2-continued

Examples of compound of formula (Ibb)

Formula Ibb

| Comp. No. | $R_{26}$ | $R_{20}$ | Xq | Structure | Phys. Data LCMS/NMR or Mpt |
|---|---|---|---|---|---|
| 2.007 | H | H | O | 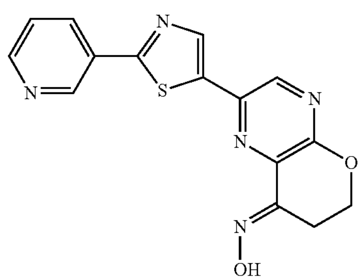 | |
| 2.008 | H | $CH_3$ | O | 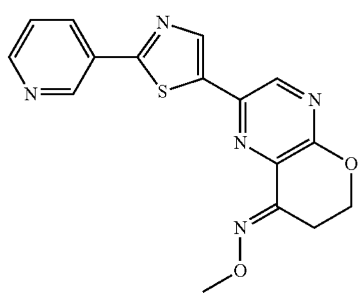 | |
| 2.009 | H | $CH_3CH_2$ | O | 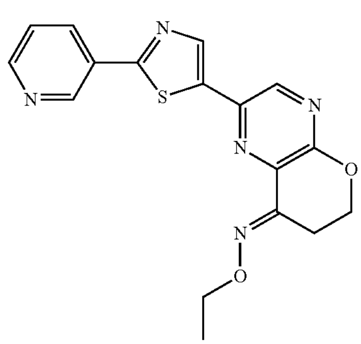 | |

TABLE 2-continued
Examples of compound of formula (Ibb)
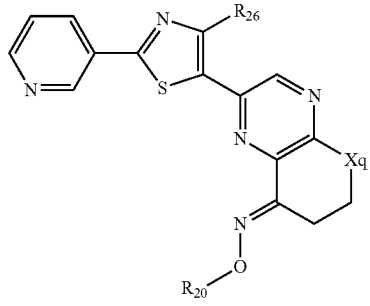
Formula Ibb
| Comp. No. | R_{26} | R_{20} | Xq | Structure | Phys. Data LCMS/NMR or Mpt |
|---|---|---|---|---|---|
| 2.010 | H | CH$_3$CH$_2$CH$_2$ | O | 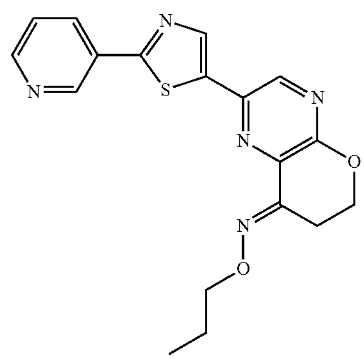 | |
| 2.011 | H | (CH$_3$)$_2$CH | O | 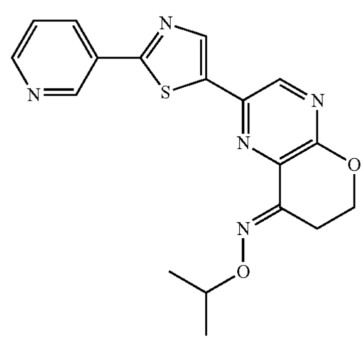 | |
| 2.012 | H | CH$_2$C=CH$_2$ | O | 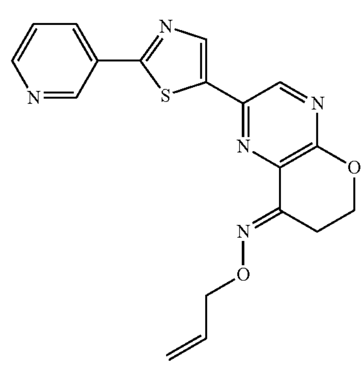 [SMILES: C=CCO/N=C1\CCOc2ncc(-c3cnc(-c4cccnc4)s3)nc21] | |

TABLE 2-continued

Examples of compound of formula (Ibb)

Formula Ibb

| Comp. No. | R$_{26}$ | R$_{20}$ | Xq | Structure | Phys. Data LCMS/NMR or Mpt |
|---|---|---|---|---|---|
| 2.013 | H | H | N—CH$_3$ | 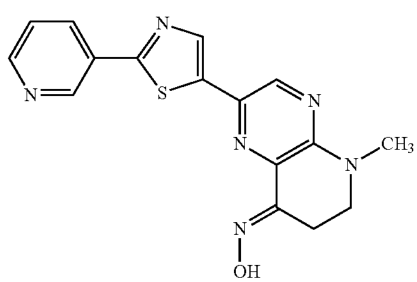 | |
| 2.014 | H | CH$_3$ | N—CH$_3$ | 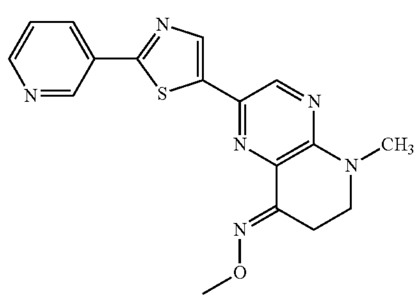 | |
| 2.015 | H | CH$_3$CH$_2$ | N—CH$_3$ | 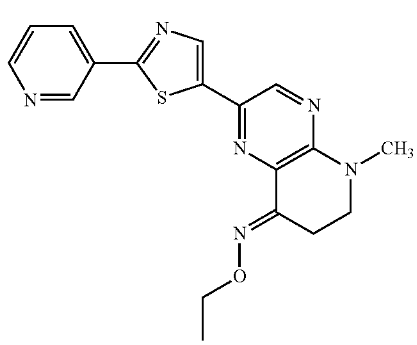 | |

TABLE 2-continued
Examples of compound of formula (Ibb)
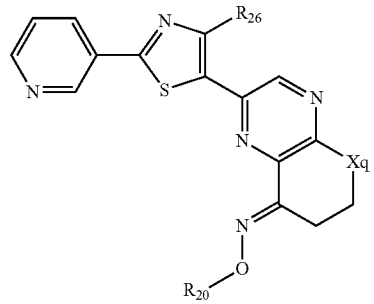
Formula Ibb
| Comp. No. | R$_{26}$ | R$_{20}$ | Xq | Structure | Phys. Data LCMS/NMR or Mpt |
|---|---|---|---|---|---|
| 2.016 | H | CH$_3$CH$_2$CH$_2$ | N—CH$_3$ | 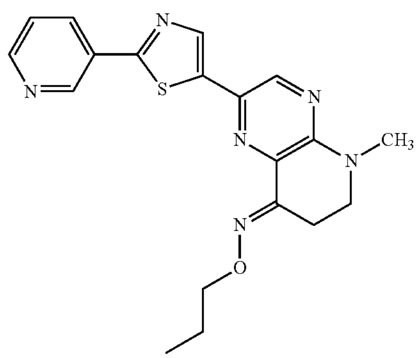 | |
| 2.017 | H | (CH$_3$)$_2$CH | N—CH$_3$ | 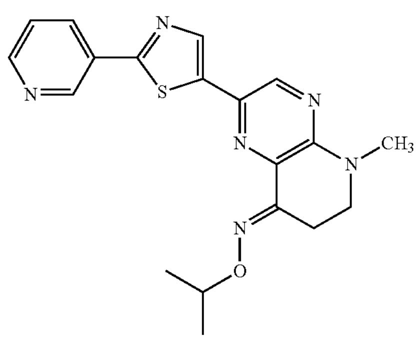 | |
| 2.018 | H | CH$_2$C═CH$_2$ | N—CH$_3$ | 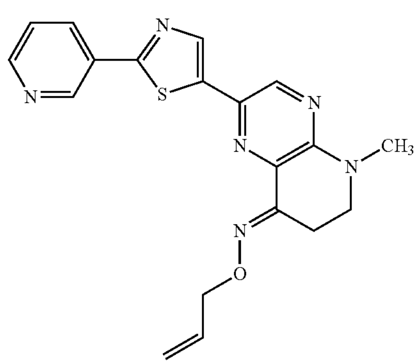 | |

TABLE 2-continued

Examples of compound of formula (Ibb)

Formula Ibb

| Comp. No. | $R_{26}$ | $R_{20}$ | Xq | Structure | Phys. Data LCMS/NMR or Mpt |
|---|---|---|---|---|---|
| 2.019 | H | H | N—SO$_2$CH$_3$ | 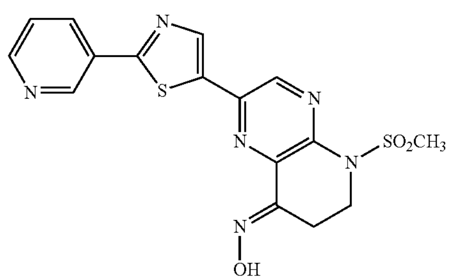 | |
| 2.020 | H | CH$_3$ | N—SO$_2$CH$_3$ | 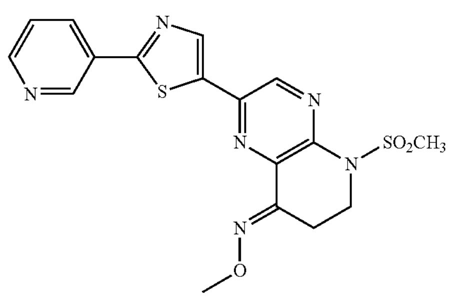 | |
| 2.021 | H | CH$_3$CH$_2$ | N—SO$_2$CH$_3$ | 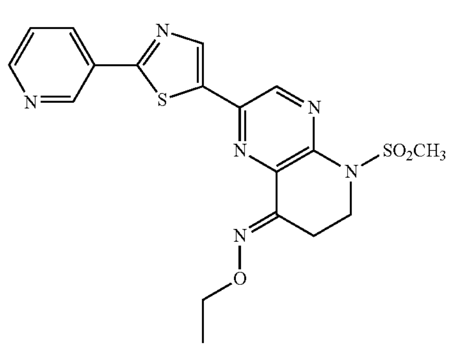 | |

TABLE 2-continued

Examples of compound of formula (Ibb)

Formula Ibb

| Comp. No. | $R_{26}$ | $R_{20}$ | Xq | Structure | Phys. Data LCMS/NMR or Mpt |
|---|---|---|---|---|---|
| 2.022 | H | $CH_3CH_2CH_2$ | N—$SO_2CH_3$ | 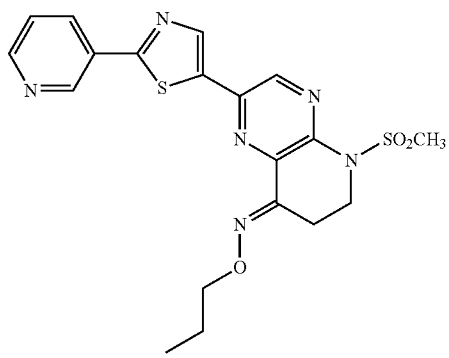 [SMILES: CCCO/N=C1\CCN(S(C)(=O)=O)c2ncc(-c3cnc(-c4cccnc4)s3)nc21] | |
| 2.023 | H | $(CH_3)_2CH$ | N—$SO_2CH_3$ | 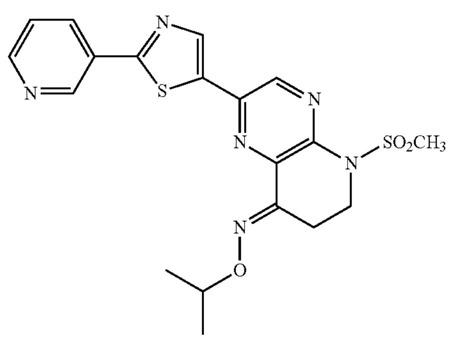 [SMILES: CC(C)O/N=C1\CCN(S(C)(=O)=O)c2ncc(-c3cnc(-c4cccnc4)s3)nc21] | |
| 2.024 | H | $CH_2C$=$CH_2$ | N—$SO_2CH_3$ | 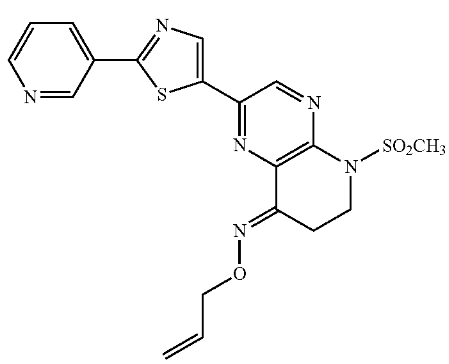 [SMILES: C=CCO/N=C1\CCN(S(C)(=O)=O)c2ncc(-c3cnc(-c4cccnc4)s3)nc21] | |

TABLE 2-continued
Examples of compound of formula (Ibb)
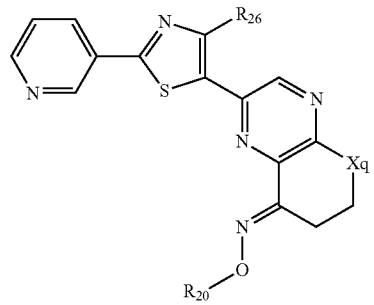
Formula Ibb
| Comp. No. | $R_{26}$ | $R_{20}$ | $X_q$ | Structure | Phys. Data LCMS/NMR or Mpt |
|---|---|---|---|---|---|
| 2.025 | $CH_3$ | H | $CH_2$ | 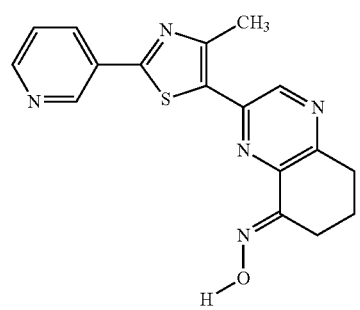 | |
| 2.026 | $CH_3$ | $CH_3$ | $CH_2$ | 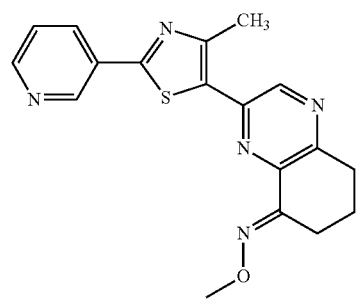 | |
| 2.027 | $CH_3$ | $CH_3CH_2$ | $CH_2$ | 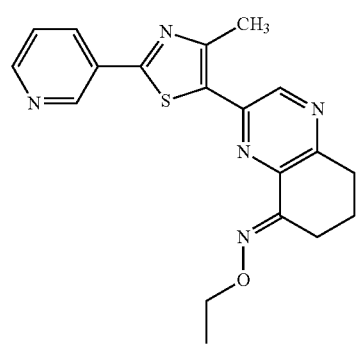 | |

TABLE 2-continued
Examples of compound of formula (Ibb)
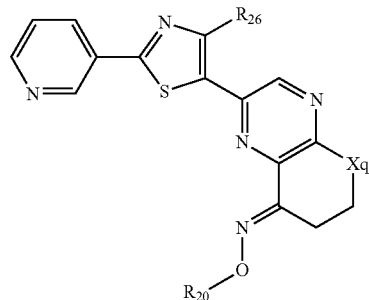
Formula Ibb
| Comp. No. | R$_{26}$ | R$_{20}$ | Xq | Structure | Phys. Data LCMS/NMR or Mpt |
|---|---|---|---|---|---|
| 2.028 | CH$_3$ | CH$_3$CH$_2$CH$_2$ | CH$_2$ | 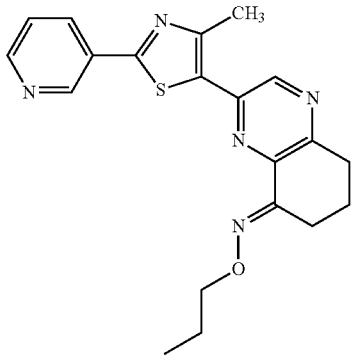 | |
| 2.029 | CH$_3$ | (CH$_3$)$_2$CH | CH$_2$ | 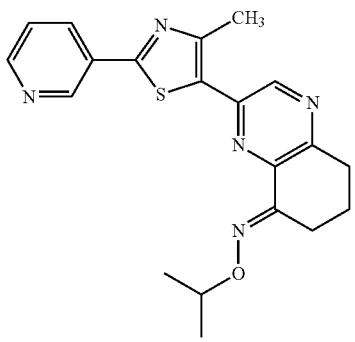 | |
| 2.030 | CH$_3$ | CH$_2$C═CH$_2$ | CH$_2$ | 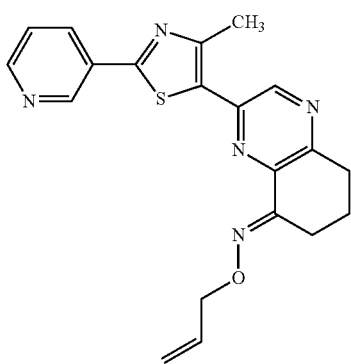 | |

TABLE 2-continued
Examples of compound of formula (Ibb)
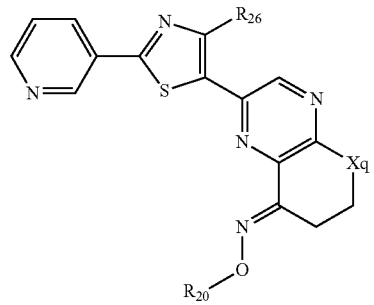
Formula Ibb
| Comp. No. | $R_{26}$ | $R_{20}$ | Xq | Structure | Phys. Data LCMS/NMR or Mpt |
|---|---|---|---|---|---|
| 2.031 | $CH_3$ | H | O | 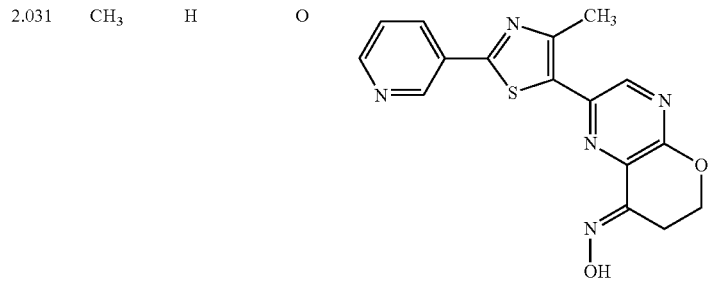 | |
| 2.032 | $CH_3$ | $CH_3$ | O | 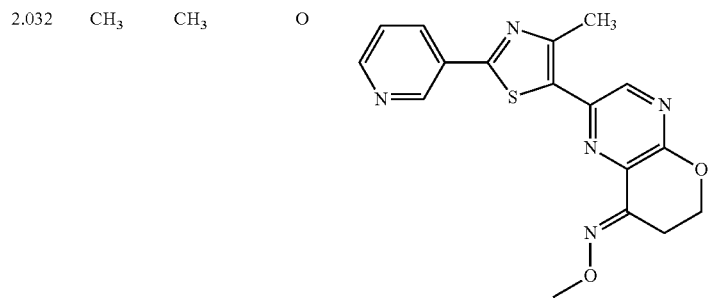 | |
| 2.033 | $CH_3$ | $CH_3CH_2$ | O | 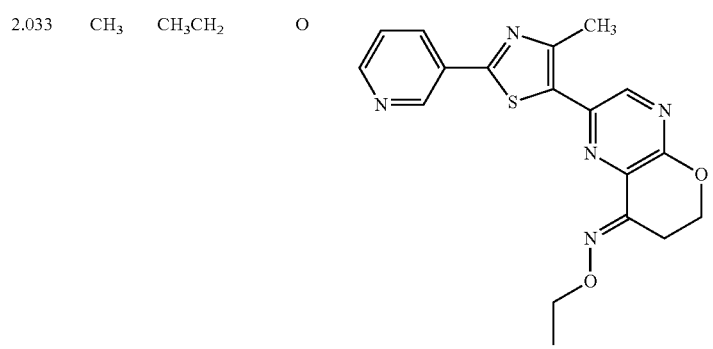 | |

TABLE 2-continued
Examples of compound of formula (Ibb)
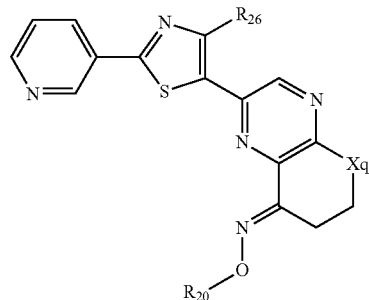
Formula Ibb
| Comp. No. | $R_{26}$ | $R_{20}$ | Xq | Structure | Phys. Data LCMS/NMR or Mpt |
|---|---|---|---|---|---|
| 2.034 | CH$_3$ | CH$_3$CH$_2$CH$_2$ | O | 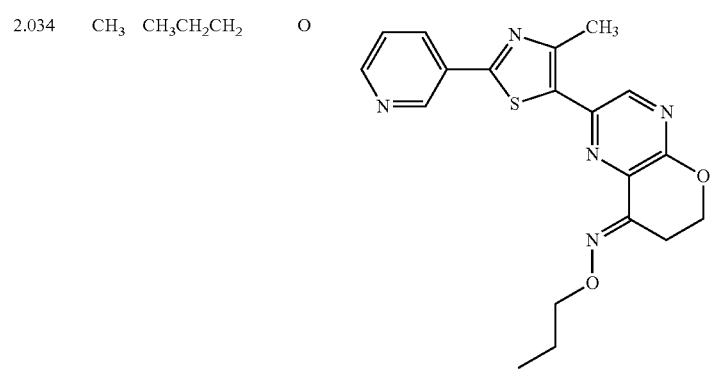 | |
| 2.035 | CH$_3$ | (CH$_3$)$_2$CH | O | 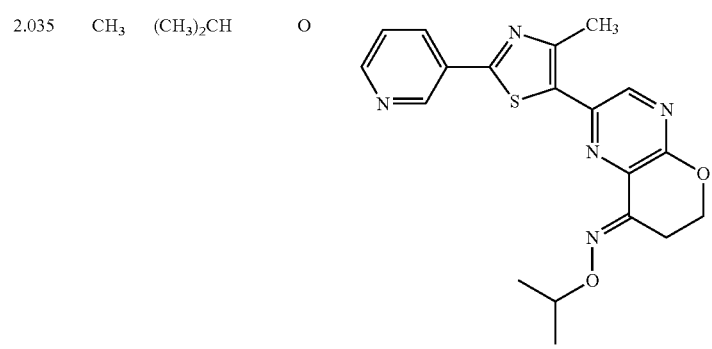 | |
| 2.036 | CH$_3$ | CH$_2$=CH$_2$ | O | 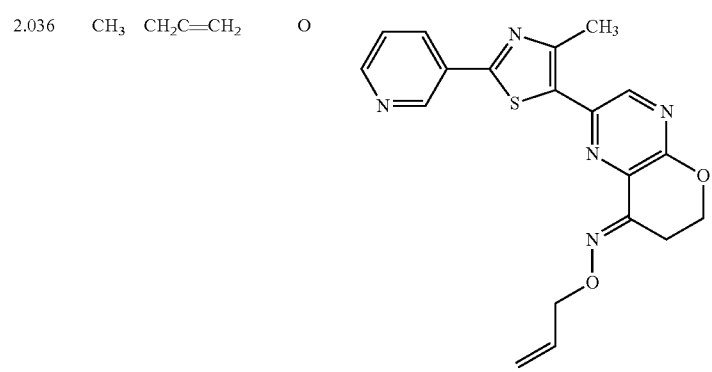 | |

TABLE 2-continued
Examples of compound of formula (Ibb)
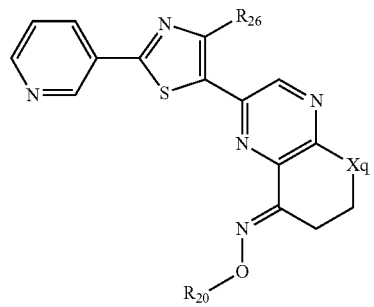
Formula Ibb
| Comp. No. | R26 | R20 | Xq | Structure | Phys. Data LCMS/NMR or Mpt |
|---|---|---|---|---|---|
| 2.037 | CH3 | H | N—CH3 | 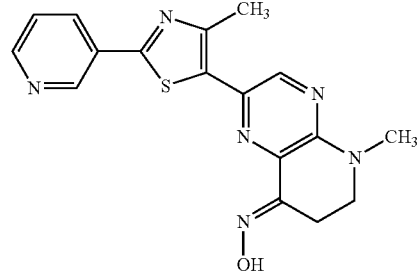 [SMILES: Cc1nc(-c2cccnc2)sc1-c1cnc2c(n1)/C(=N/O)CCN2C] | |
| 2.038 | CH3 | CH3 | N—CH3 | 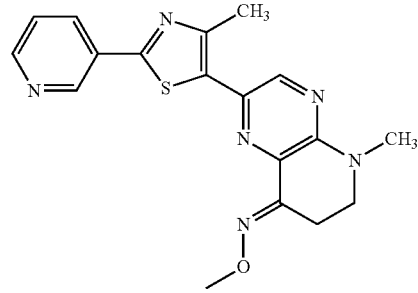 [SMILES: CO/N=C1\CCN(C)c2ncc(-c3sc(-c4cccnc4)nc3C)nc21] | |
| 2.039 | CH3 | CH3CH2 | N—CH3 | 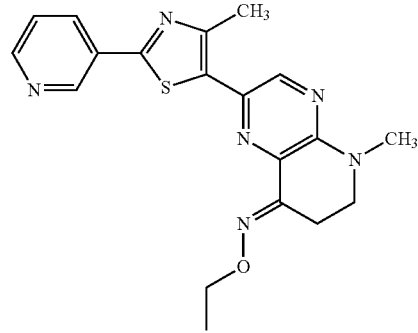 [SMILES: CCO/N=C1\CCN(C)c2ncc(-c3sc(-c4cccnc4)nc3C)nc21] | |

TABLE 2-continued
Examples of compound of formula (Ibb)
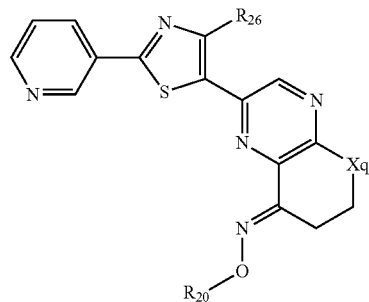
Formula Ibb
| Comp. No. | $R_{26}$ | $R_{20}$ | Xq | Structure | Phys. Data LCMS/NMR or Mpt |
|---|---|---|---|---|---|
| 2.040 | $CH_3$ | $CH_3CH_2CH_2$ | $N-CH_3$ | 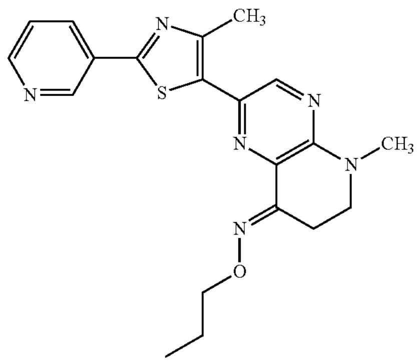 | |
| 2.041 | $CH_3$ | $(CH_3)_2CH$ | $N-CH_3$ | 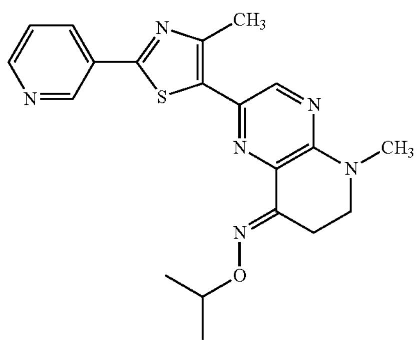 | |
| 2.042 | $CH_3$ | $CH_2=CH_2$ | $N-CH_3$ | 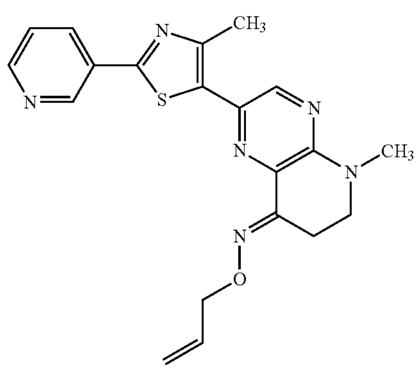 | |

TABLE 2-continued
Examples of compound of formula (Ibb)
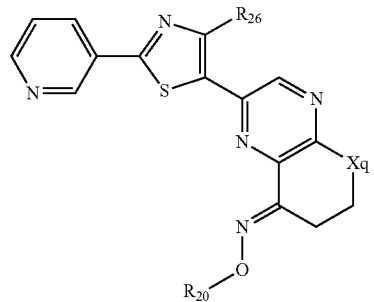
Formula Ibb
| Comp. No. | R<sub>26</sub> | R<sub>20</sub> | Xq | Structure | Phys. Data LCMS/NMR or Mpt |
|---|---|---|---|---|---|
| 2.043 | $CH_3$ | H | $N-SO_2CH_3$ | 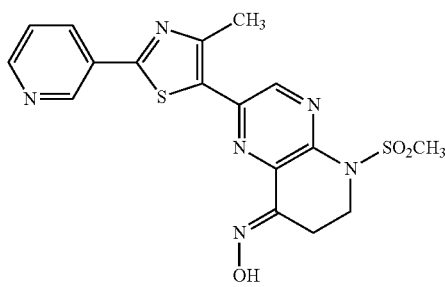 | |
| 2.044 | $CH_3$ | $CH_3$ | $N-SO_2CH_3$ | 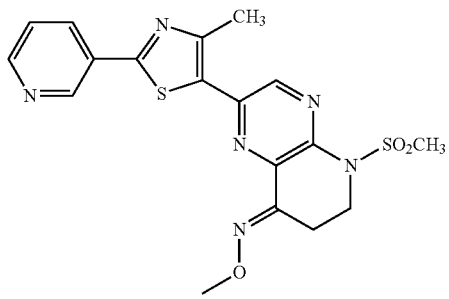 | |
| 2.045 | $CH_3$ | $CH_3CH_2$ | $N-SO_2CH_3$ | 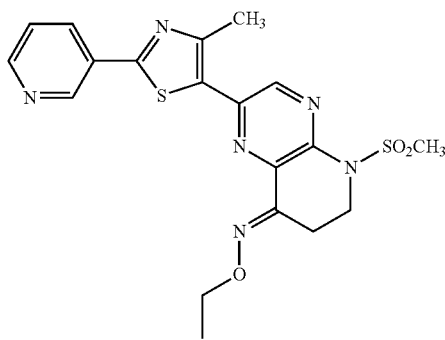 [SMILES: CCO/N=C1\CCN(S(C)(=O)=O)c2ncc(-c3sc(-c4cccnc4)nc3C)nc21] | |

TABLE 2-continued
Examples of compound of formula (Ibb)
Formula Ibb
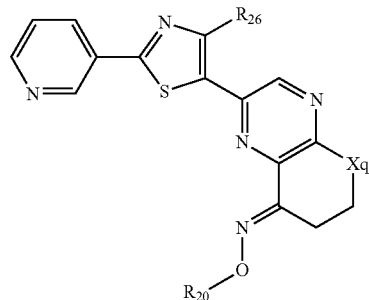
| Comp. No. | R$_{26}$ | R$_{20}$ | Xq | Structure | Phys. Data LCMS/NMR or Mpt |
|---|---|---|---|---|---|
| 2.046 | CH$_3$ | CH$_3$CH$_2$CH$_2$ | N—SO$_2$CH$_3$ | 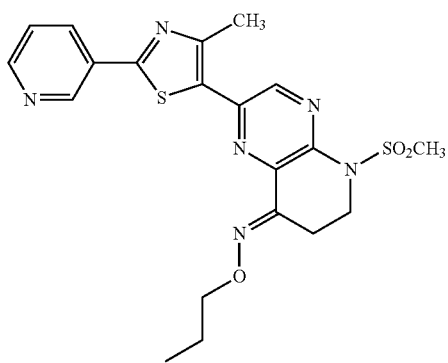 | |
| 2.047 | CH$_3$ | (CH$_3$)$_2$CH | N—SO$_2$CH$_3$ | 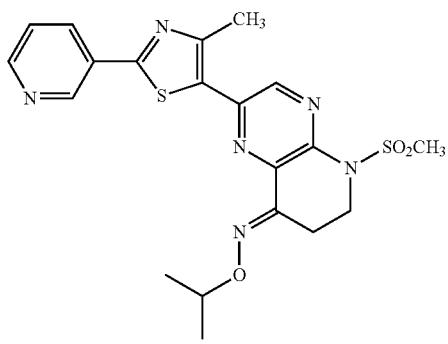 | |
| 2.048 | CH$_3$ | CH$_2$C=CH$_2$ | N—SO$_2$CH$_3$ | 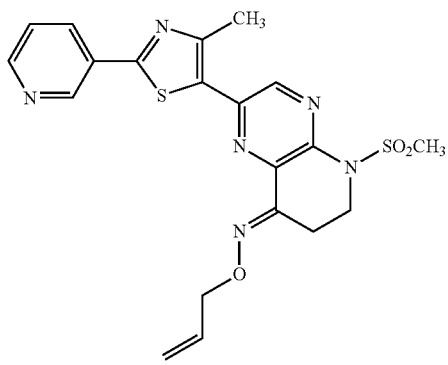 [SMILES: C=CCO/N=C1\CCN(S(C)(=O)=O)c2ncc(-c3sc(-c4cccnc4)nc3C)nc21] | |

TABLE 3
Examples of compound of formula (Icc)
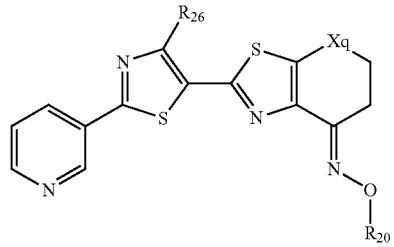
Formula Icc
| Comp. No. | R$_{26}$ | R$_{20}$ | Xq | Structure | Phys. Data LCMS/NMR or Mpt |
|---|---|---|---|---|---|
| 3.001 | H | H | CH$_2$ | 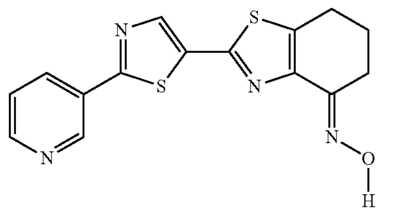 | |
| 3.002 | H | CH$_3$ | CH$_2$ | 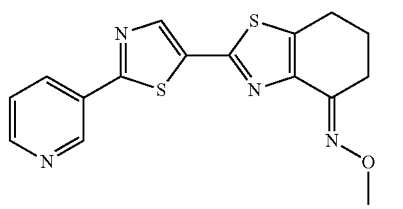 | |
| 3.003 | H | CH$_3$CH$_2$ | CH$_2$ | 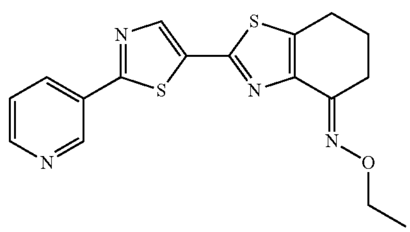 | |
| 3.004 | H | CH$_3$CH$_2$CH$_2$ | CH$_2$ | 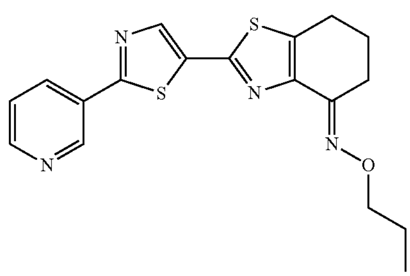 | |
| 3.005 | H | (CH$_3$)$_2$CH | CH$_2$ | 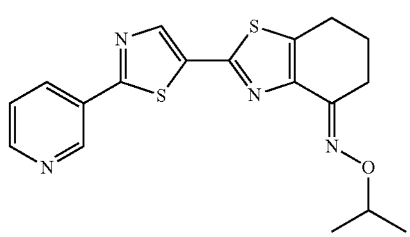 | |

TABLE 3-continued

Examples of compound of formula (Icc)

Formula Icc

| Comp. No. | $R_{26}$ | $R_{20}$ | Xq | Structure | Phys. Data LCMS/NMR or Mpt |
|---|---|---|---|---|---|
| 3.006 | H | CH$_2$C=CH$_2$ | CH$_2$ | 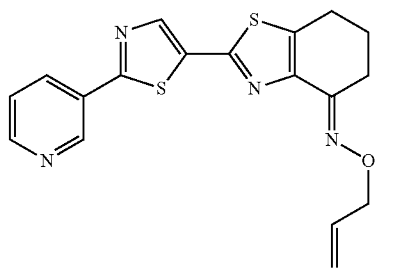 | |
| 3.007 | H | H | O | 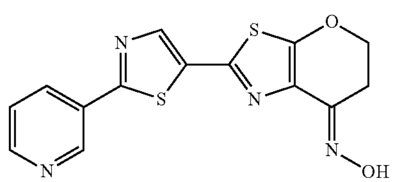 | |
| 3.008 | H | CH$_3$ | O | 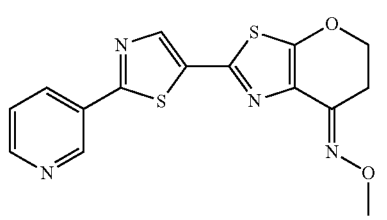 | |
| 3.009 | H | CH$_3$CH$_2$ | O | 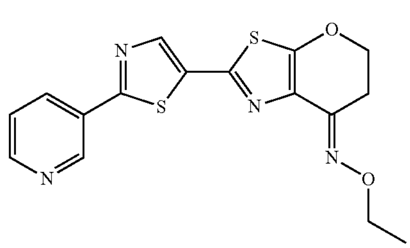 [SMILES: CCO/N=C1\CCOc2sc(-c3cnc(-c4cccnc4)s3)nc21] | |
| 3.010 | H | CH$_3$CH$_2$CH$_2$ | O | 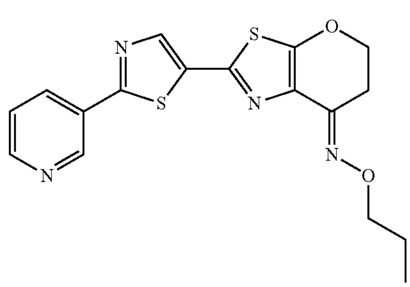 [SMILES: CCCO/N=C1\CCOc2sc(-c3cnc(-c4cccnc4)s3)nc21] | |

TABLE 3-continued

Examples of compound of formula (Icc)

Formula Icc

| Comp. No. | $R_{26}$ | $R_{20}$ | Xq | Structure | Phys. Data LCMS/NMR or Mpt |
|---|---|---|---|---|---|
| 3.011 | H | (CH$_3$)$_2$CH | O | 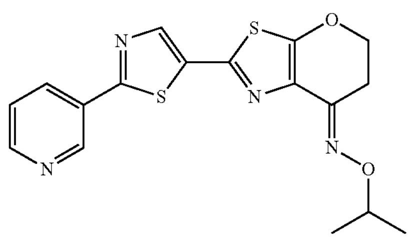 | |
| 3.012 | H | CH$_2$C=CH$_2$ | O | 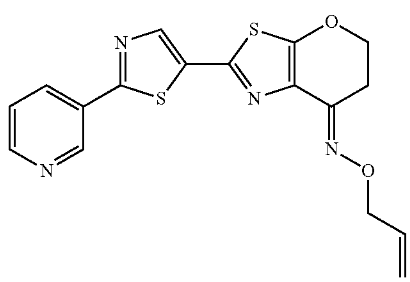 | |
| 3.013 | H | H | N—CH$_3$ | 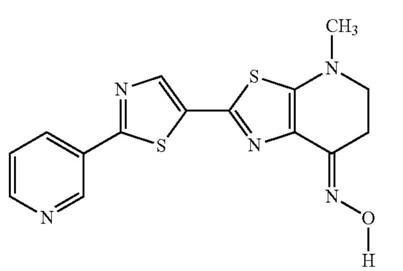 | |
| 3.014 | H | CH$_3$ | N—CH$_3$ | 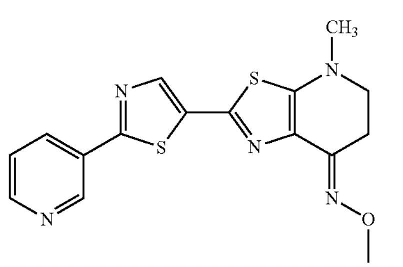 | |

TABLE 3-continued

Examples of compound of formula (Icc)

Formula Icc

| Comp. No. | $R_{26}$ | $R_{20}$ | Xq | Structure | Phys. Data LCMS/NMR or Mpt |
|---|---|---|---|---|---|
| 3.015 | H | CH$_3$CH$_2$ | N—CH$_3$ | 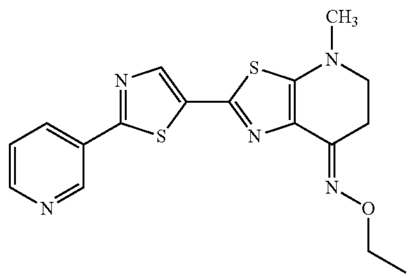 [SMILES: CCO/N=C1\CCN(C)c2sc(-c3cnc(-c4cccnc4)s3)nc21] | |
| 3.016 | H | CH$_3$CH$_2$CH$_2$ | N—CH$_3$ | 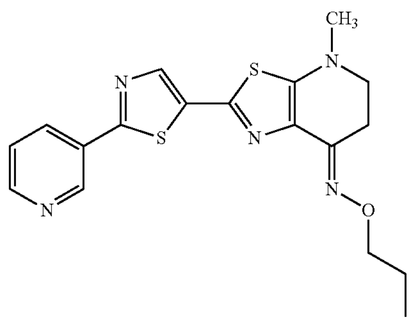 [SMILES: CCCO/N=C1\CCN(C)c2sc(-c3cnc(-c4cccnc4)s3)nc21] | |
| 3.017 | H | (CH$_3$)$_2$CH | N—CH$_3$ | 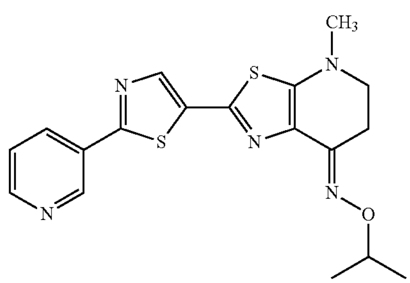 [SMILES: CC(C)O/N=C1\CCN(C)c2sc(-c3cnc(-c4cccnc4)s3)nc21] | |
| 3.018 | H | CH$_2$C=CH$_2$ | N—CH$_3$ | 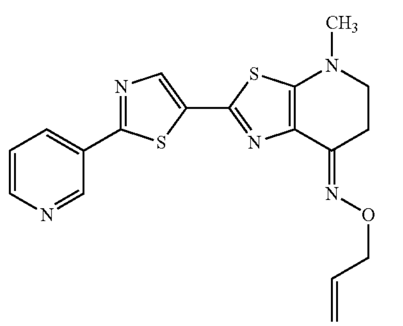 [SMILES: C=CCO/N=C1\CCN(C)c2sc(-c3cnc(-c4cccnc4)s3)nc21] | |

TABLE 3-continued

Examples of compound of formula (Icc)

Formula Icc

| Comp. No. | $R_{26}$ | $R_{20}$ | Xq | Structure | Phys. Data LCMS/NMR or Mpt |
|---|---|---|---|---|---|
| 3.019 | H | H | N—SO$_2$CH$_3$ | 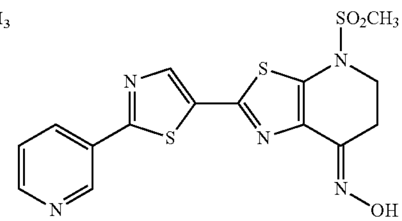 | |
| 3.020 | H | CH$_3$ | N—SO$_2$CH$_3$ | 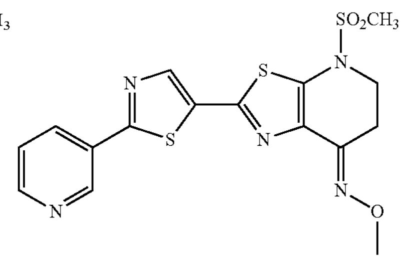 | |
| 3.021 | H | CH$_3$CH$_2$ | N—SO$_2$CH$_3$ | 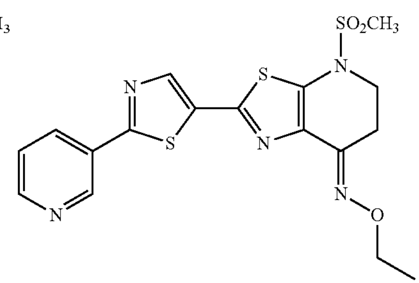 | |
| 3.022 | H | CH$_3$CH$_2$CH$_2$ | N—SO$_2$CH$_3$ | 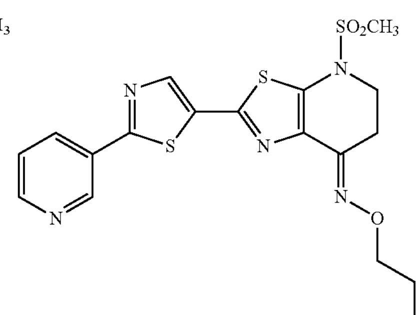 | |

TABLE 3-continued

Examples of compound of formula (Icc)

Formula Icc

| Comp. No. | R₂₆ | R₂₀ | Xq | Structure | Phys. Data LCMS/NMR or Mpt |
|---|---|---|---|---|---|
| 3.023 | H | (CH₃)₂CH | N—SO₂CH₃ | 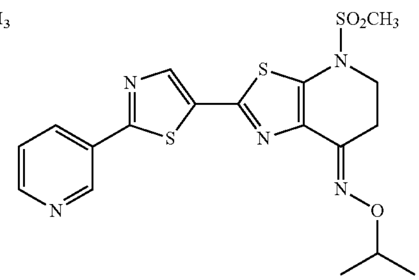 | |
| 3.024 | H | CH₂=CH₂ | N—SO₂CH₃ | 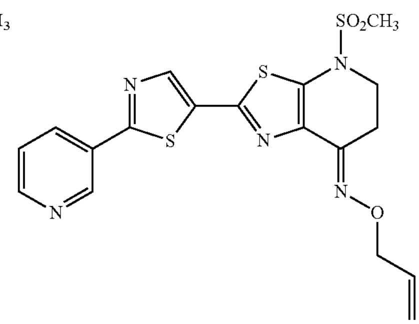 | |
| 3.025 | CH₃ | H | CH₂ | 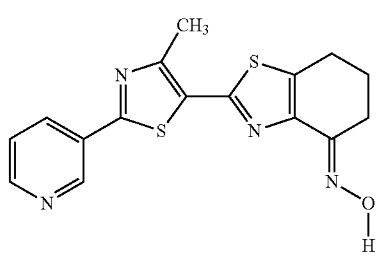 | |
| 3.026 | CH₃ | CH₃ | CH₂ | 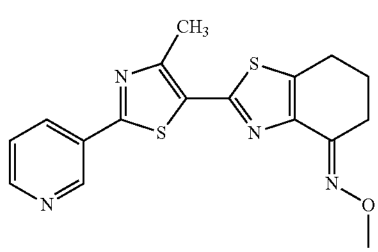 | |

TABLE 3-continued
Examples of compound of formula (Icc)
Formula Icc
| Comp. No. | $R_{26}$ | $R_{20}$ | Xq | Structure | Phys. Data LCMS/NMR or Mpt |
|---|---|---|---|---|---|
| 3.027 | $CH_3$ | $CH_3CH_2$ | $CH_2$ | 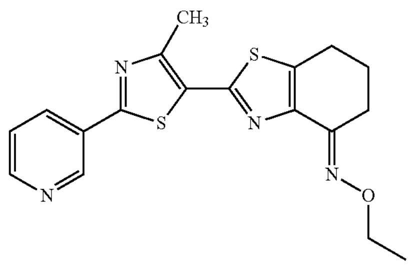 | |
| 3.028 | $CH_3$ | $CH_3CH_2CH_2$ | $CH_2$ | 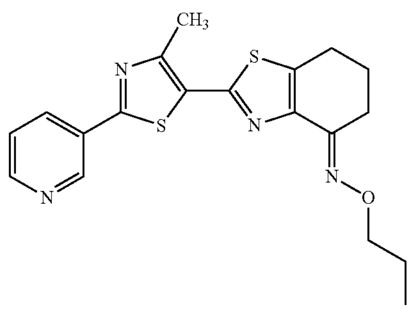 | |
| 3.029 | $CH_3$ | $(CH_3)_2CH$ | $CH_2$ | 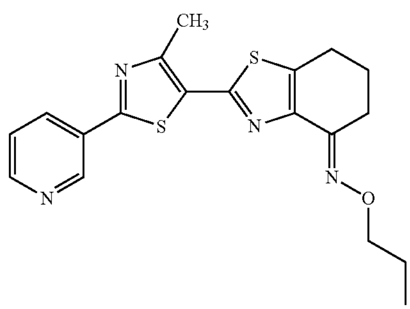 | |
| 3.030 | $CH_3$ | $CH_2{=}CH_2$ | $CH_2$ | 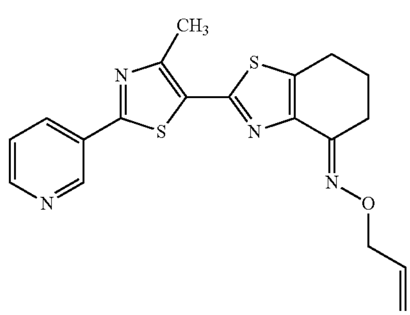 | |

TABLE 3-continued

Examples of compound of formula (Icc)

Formula Icc

| Comp. No. | $R_{26}$ | $R_{20}$ | Xq | Structure | Phys. Data LCMS/NMR or Mpt |
|---|---|---|---|---|---|
| 3.031 | $CH_3$ | H | O | 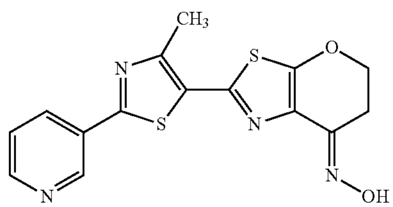 | |
| 3.032 | $CH_3$ | $CH_3$ | O | 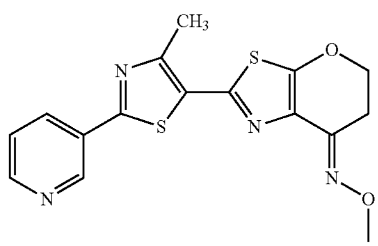 | |
| 3.033 | $CH_3$ | $CH_3CH_2$ | O | 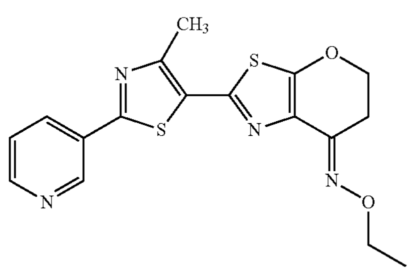 [SMILES: CCO/N=C1\CCOc2sc(-c3sc(-c4cccnc4)nc3C)nc21] | |
| 3.034 | $CH_3$ | $CH_3CH_2CH_2$ | O | 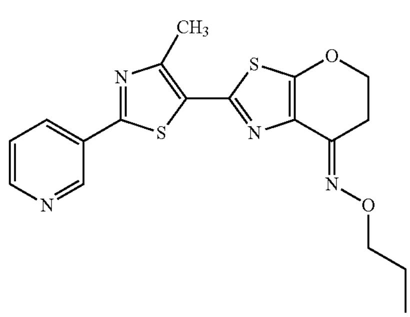 [SMILES: CCCO/N=C1\CCOc2sc(-c3sc(-c4cccnc4)nc3C)nc21] | |

TABLE 3-continued
Examples of compound of formula (Icc)
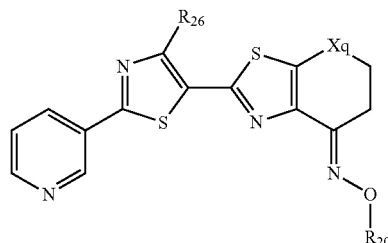
Formula Icc
| Comp. No. | R<sub>26</sub> | R<sub>20</sub> | Xq | Structure | Phys. Data LCMS/NMR or Mpt |
|---|---|---|---|---|---|
| 3.035 | $CH_3$ | $(CH_3)_2CH$ | O | 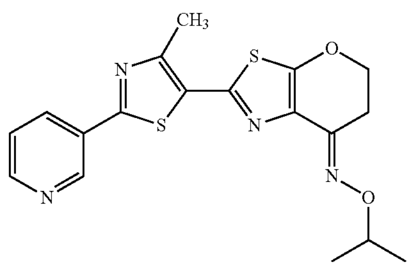 [SMILES: Cc1nc(-c2cccnc2)sc1-c1nc2c(s1)OCC/C2=N\OC(C)C] | |
| 3.036 | $CH_3$ | $CH_2C{=}CH_2$ | O | 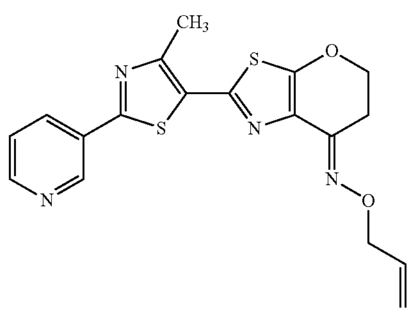 | |
| 3.037 | $CH_3$ | H | N—$CH_3$ | 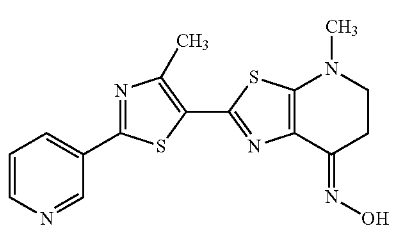 | |
| 3.038 | $CH_3$ | $CH_3$ | N—$CH_3$ | 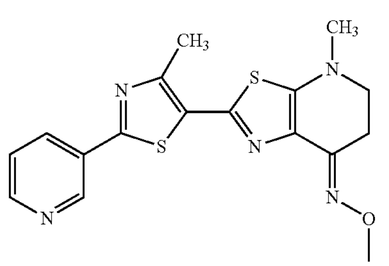 | |

TABLE 3-continued

Examples of compound of formula (Icc)

Formula Icc

| Comp. No. | $R_{26}$ | $R_{20}$ | Xq | Structure | Phys. Data LCMS/NMR or Mpt |
|---|---|---|---|---|---|
| 3.039 | $CH_3$ | $CH_3CH_2$ | N—$CH_3$ | 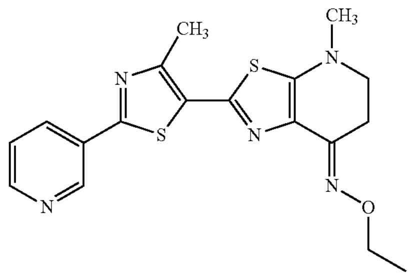 [SMILES: CCO/N=C1\CCN(C)c2sc(-c3sc(-c4cccnc4)nc3C)nc21] | |
| 3.040 | $CH_3$ | $CH_3CH_2CH_2$ | N—$CH_3$ | 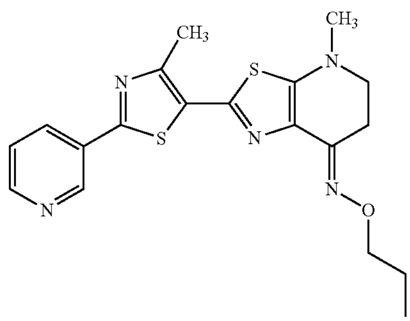 | |
| 3.041 | $CH_3$ | $(CH_3)_2CH$ | N—$CH_3$ | 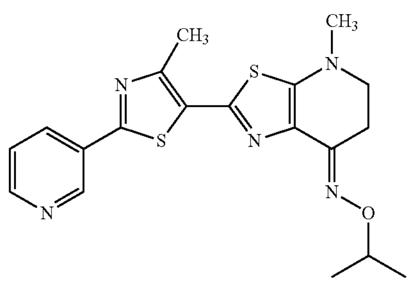 [SMILES: Cc1nc(-c2cccnc2)sc1-c1nc2c(s1)N(C)CC/C2=N\OC(C)C] | |
| 3.042 | $CH_3$ | $CH_2$=$CH_2$ | N—$CH_3$ | 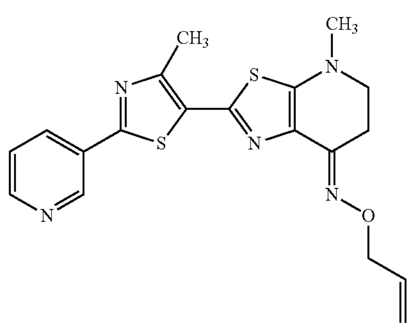 [SMILES: C=CCO/N=C1\CCN(C)c2sc(-c3sc(-c4cccnc4)nc3C)nc21] | |

TABLE 3-continued
Examples of compound of formula (Icc)
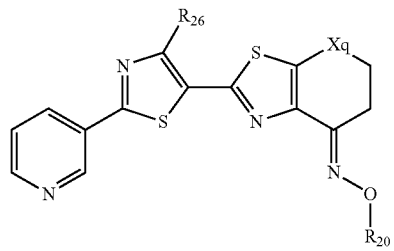
Formula Icc
| Comp. No. | $R_{26}$ | $R_{20}$ | Xq | Structure | Phys. Data LCMS/NMR or Mpt |
|---|---|---|---|---|---|
| 3.043 | $CH_3$ | H | $N-SO_2CH_3$ | 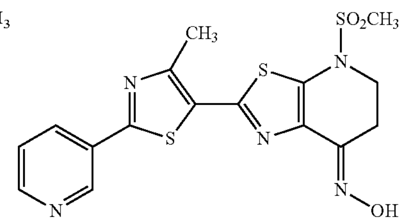 | |
| 3.044 | $CH_3$ | $CH_3$ | $N-SO_2CH_3$ | 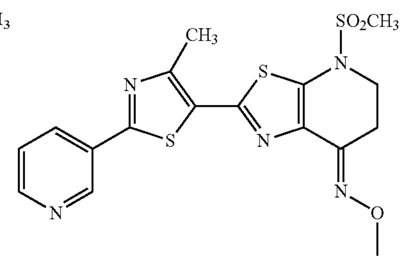 | |
| 3.045 | $CH_3$ | $CH_3CH_2$ | $N-SO_2CH_3$ | 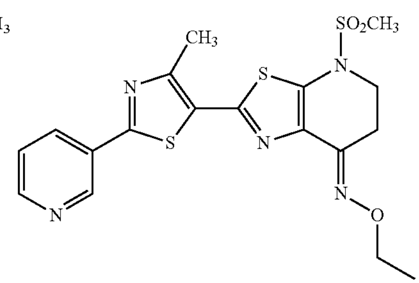 | |
| 3.046 | $CH_3$ | $CH_3CH_2CH_2$ | $N-SO_2CH_3$ | 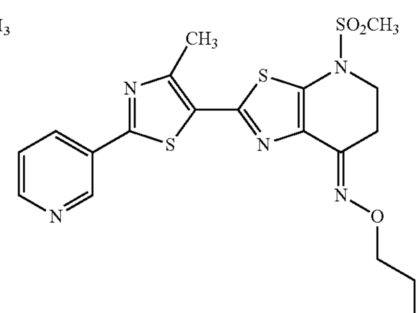 | |

TABLE 3-continued
Examples of compound of formula (Icc)
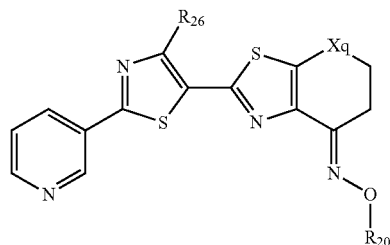
Formula Icc
| Comp. No. | R$_{26}$ | R$_{20}$ | Xq | Structure | Phys. Data LCMS/NMR or Mpt |
|---|---|---|---|---|---|
| 3.047 | CH$_3$ | (CH$_3$)$_2$CH | N—SO$_2$CH$_3$ | 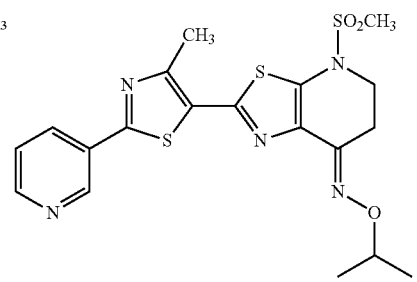 | |
| 3.048 | CH$_3$ | CH$_2$=CH$_2$ | N—SO$_2$CH$_3$ | 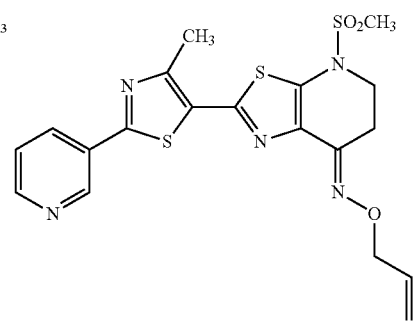 | |
| 3.049 | CH$_3$ | H | S | 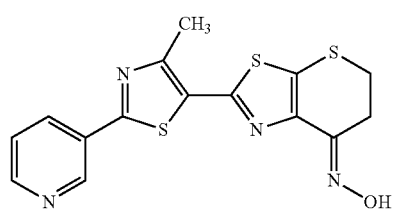 | |
| 3.050 | CH$_3$ | CH$_3$ | S | 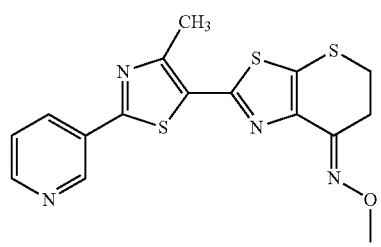 | Mpt 188-190° C. |

TABLE 3-continued
Examples of compound of formula (Icc)
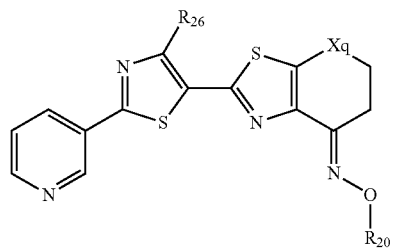
Formula Icc
| Comp. No. | $R_{26}$ | $R_{20}$ | $X_q$ | Structure | Phys. Data LCMS/NMR or Mpt |
|---|---|---|---|---|---|
| 3.051 | $CH_3$ | $CH_3CH_2$ | S | 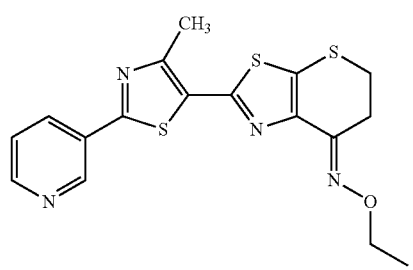 | |
| 3.052 | $CH_3$ | $(CH_3)_2CH$ | S | 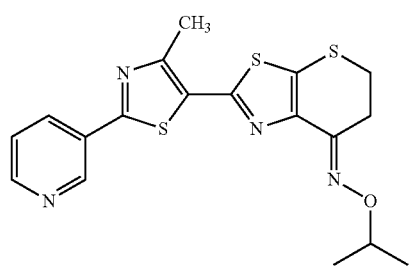 | Mpt 115-118° C. |
| 3.053 | $CH_3$ | $CH_2{=}CH_2$ | S | 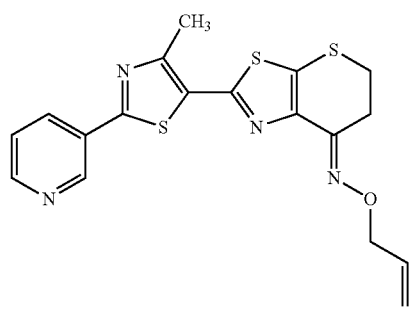 [SMILES: C=CCO/N=C1\CCSc2sc(-c3sc(-c4cccnc4)nc3C)nc21] | Mpt 65-67° C. |

TABLE 4

Examples of compound of formula (Idd)

Formula Idd

| Comp. No. | R26 | R20 | Xq | Structure | Phy. Data LCMS/NMR or Mpt |
|---|---|---|---|---|---|
| 4.001 | H | H | CH₂ | 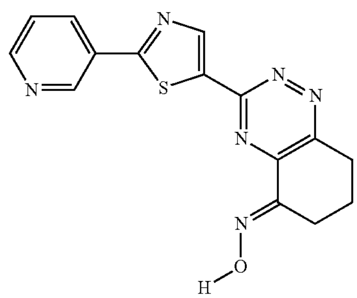 | |
| 4.002 | H | CH₃ | CH₂ | 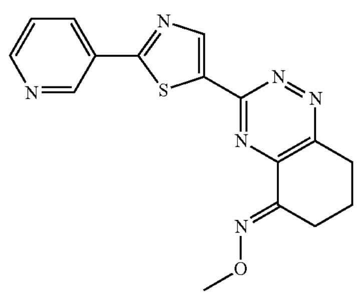 | |
| 4.003 | H | CH₃CH₂ | CH₂ | 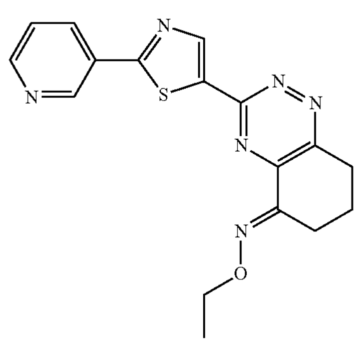 | |

TABLE 4-continued
Examples of compound of formula (Idd)
Formula Idd
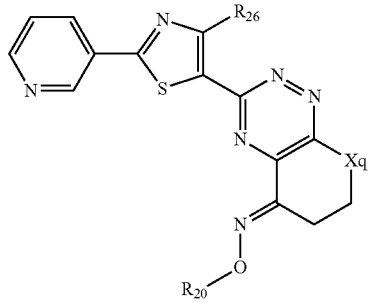
| Comp. No. | R₂₆ | R₂₀ | Xq | Structure | Phy. Data LCMS/NMR or Mpt |
|---|---|---|---|---|---|
| 4.004 | H | CH₃CH₂CH₂ | CH₂ | 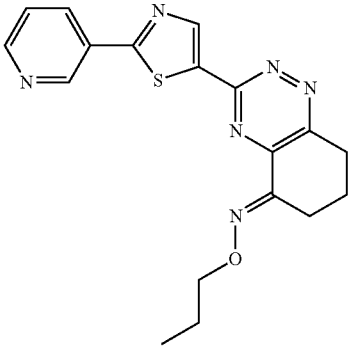 | |
| 4.005 | H | (CH₃)₂CH | CH₂ | 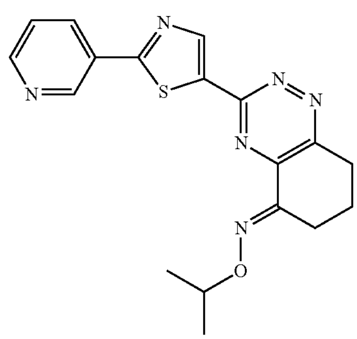 | |
| 4.006 | H | CH₂=CH₂ | CH₂ | 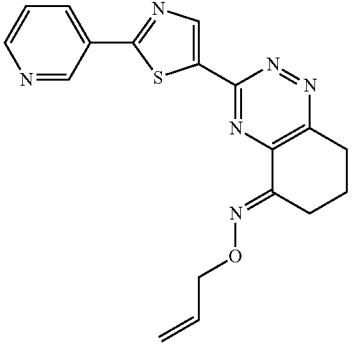 | |

TABLE 4-continued
Examples of compound of formula (Idd)
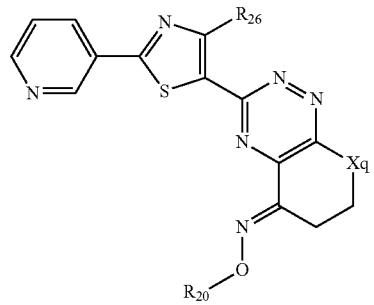
Formula Idd
| Comp. No. | $R_{26}$ | $R_{20}$ | Xq | Structure | Phy. Data LCMS/NMR or Mpt |
|---|---|---|---|---|---|
| 4.007 | H | H | O | 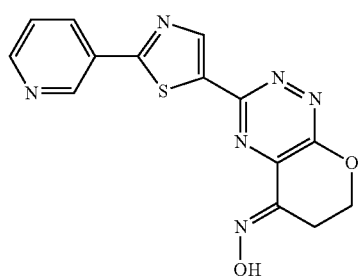 | |
| 4.008 | H | $CH_3$ | O | 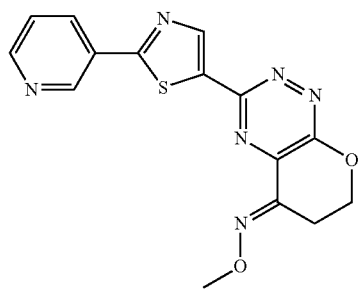 | |
| 4.009 | H | $CH_3CH_2$ | O | 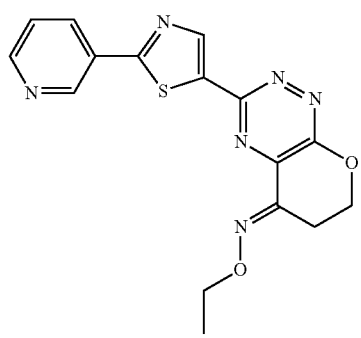 [SMILES: CCO/N=C1\CCOc2nnc(-c3cnc(-c4cccnc4)s3)nc21] | |

TABLE 4-continued
Examples of compound of formula (Idd)
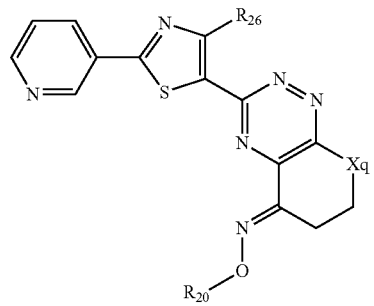
Formula Idd
| Comp. No. | $R_{26}$ | $R_{20}$ | Xq | Structure | Phy. Data LCMS/NMR or Mpt |
|---|---|---|---|---|---|
| 4.01 | H | $CH_3CH_2CH_2$ | O | 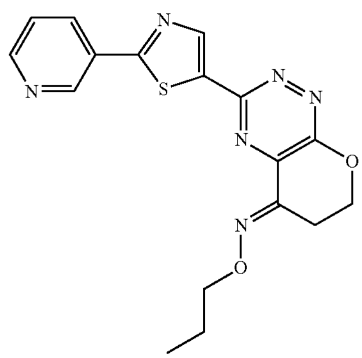 | |
| 4.011 | H | $(CH_3)_2CH$ | O | 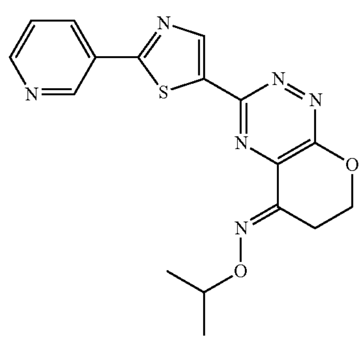 | |
| 4.012 | H | $CH_2=CH_2$ | O | 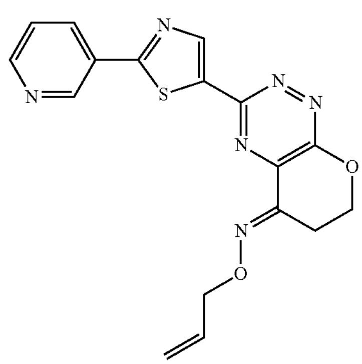 [SMILES: C=CCO/N=C1\CCOc2nnc(-c3cnc(-c4cccnc4)s3)nc21] | |

TABLE 4-continued

Examples of compound of formula (Idd)

Formula Idd

| Comp. No. | R₂₆ | R₂₀ | Xq | Structure | Phy. Data LCMS/NMR or Mpt |
|---|---|---|---|---|---|
| 4.013 | H | H | N—CH₃ | 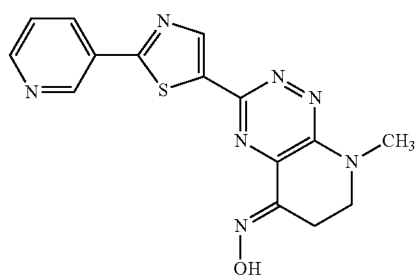 | |
| 4.014 | H | CH₃ | N—CH₃ | 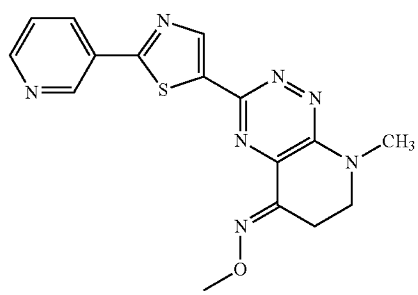 | |
| 4.015 | H | CH₃CH₂ | N—CH₃ | 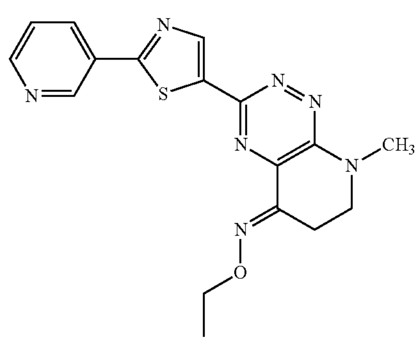 [SMILES: CCO/N=C1\CCN(C)c2nnc(-c3cnc(-c4cccnc4)s3)nc21] | |

TABLE 4-continued
Examples of compound of formula (Idd)
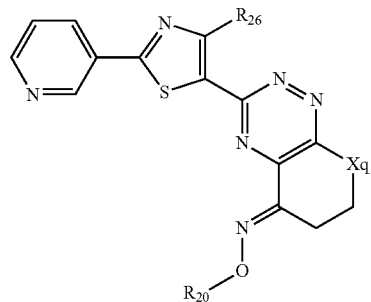
Formula Idd
| Comp. No. | R26 | R20 | Xq | Structure | Phy. Data LCMS/NMR or Mpt |
|---|---|---|---|---|---|
| 4.016 | H | CH3CH2CH2 | N—CH3 | 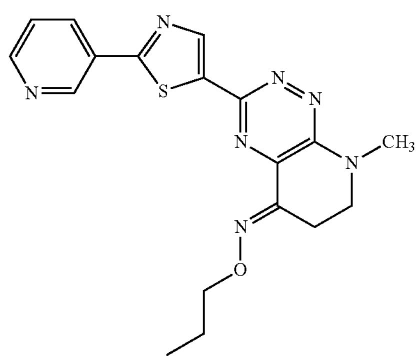 [SMILES: CCCO/N=C1\CCN(C)c2nnc(-c3cnc(-c4cccnc4)s3)nc21] | |
| 4.017 | H | (CH3)2CH | N—CH3 | 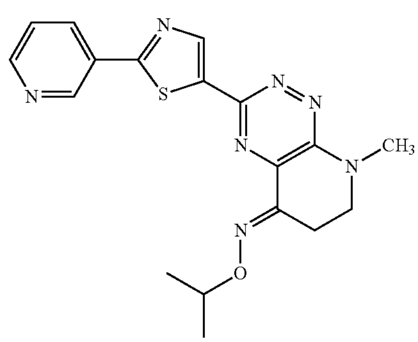 [SMILES: CC(C)O/N=C1\CCN(C)c2nnc(-c3cnc(-c4cccnc4)s3)nc21] | |
| 4.018 | H | CH2=CH2 | N—CH3 | 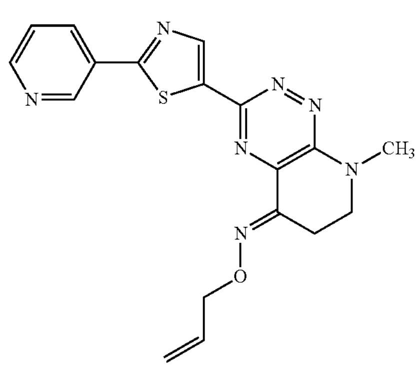 | |

TABLE 4-continued
Examples of compound of formula (Idd)
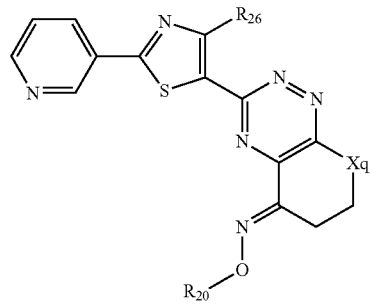
Formula Idd
| Comp. No. | $R_{26}$ | $R_{20}$ | Xq | Structure | Phy. Data LCMS/NMR or Mpt |
|---|---|---|---|---|---|
| 4.019 | H | H | N—SO$_2$CH$_3$ | 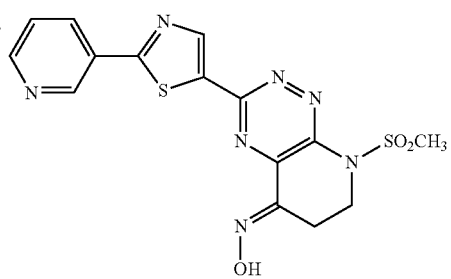 | |
| 4.020 | H | CH$_3$ | N—SO$_2$CH$_3$ | 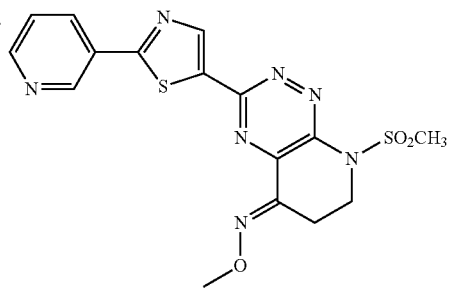 | |
| 4.021 | H | CH$_3$CH$_2$ | N—SO$_2$CH$_3$ | 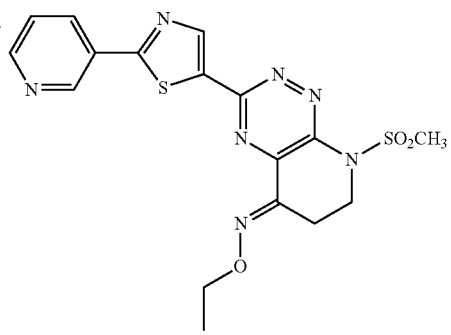 | |

TABLE 4-continued
Examples of compound of formula (Idd)
Formula Idd
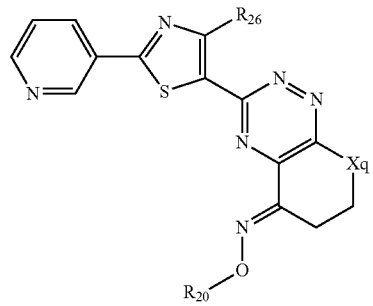
| Comp. No. | R26 | R20 | Xq | Structure | Phy. Data LCMS/NMR or Mpt |
|---|---|---|---|---|---|
| 4.022 | H | CH3CH2CH2 | N—SO2CH3 | 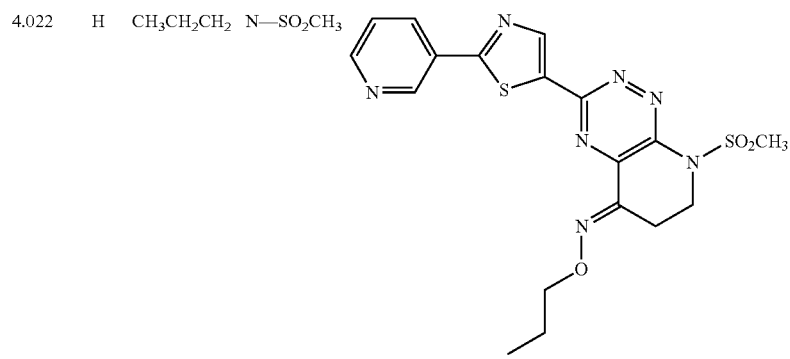 | |
| 4.023 | H | (CH3)2CH | N—SO2CH3 | 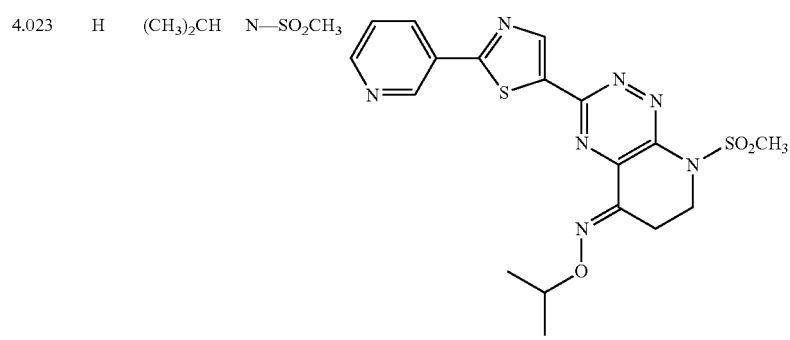 | |
| 4.024 | H | CH2=CH2 | N—SO2CH3 | 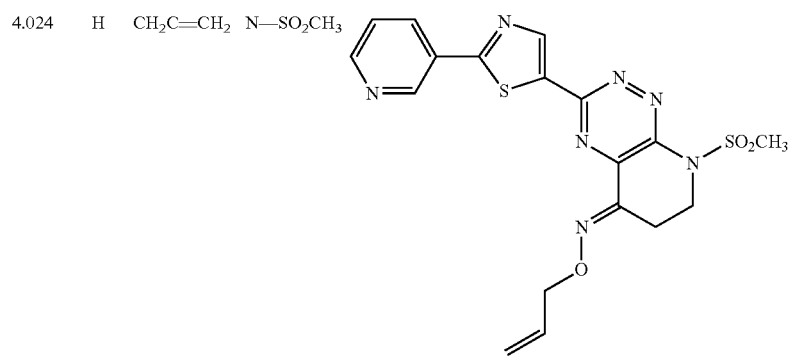 | |

TABLE 4-continued
Examples of compound of formula (Idd)
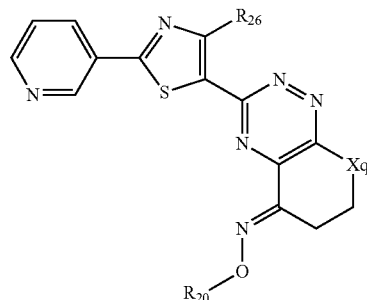
Formula Idd
| Comp. No. | R<sub>26</sub> | R<sub>20</sub> | Xq | Structure | Phy. Data LCMS/NMR or Mpt |
|---|---|---|---|---|---|
| 4.025 | CH$_3$ | H | CH$_2$ | 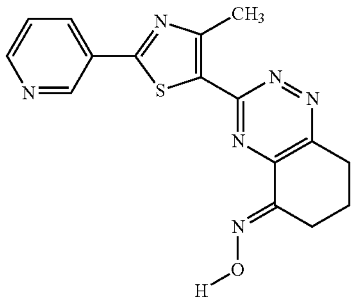 | |
| 4.026 | CH$_3$ | CH$_3$ | CH$_2$ | 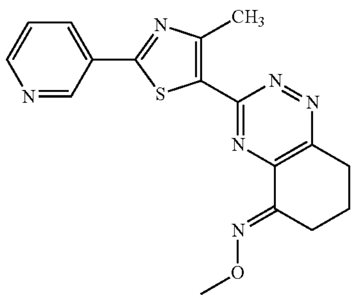 | |
| 4.027 | CH$_3$ | CH$_3$CH$_2$ | CH$_2$ | 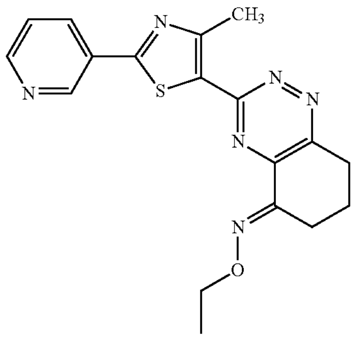 | |

TABLE 4-continued
Examples of compound of formula (Idd)
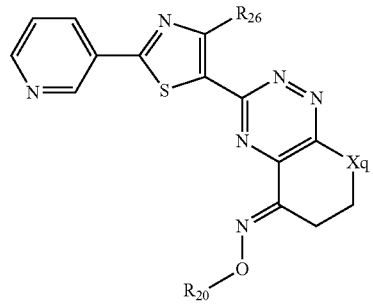
Formula Idd
| Comp. No. | R26 | R20 | Xq | Structure | Phy. Data LCMS/NMR or Mpt |
|---|---|---|---|---|---|
| 4.028 | CH3 | CH3CH2CH2 | CH2 | 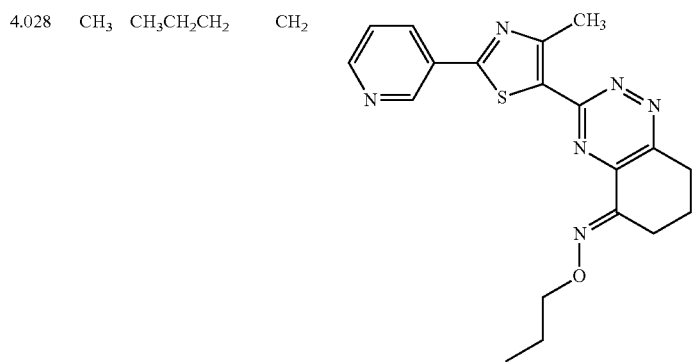 | |
| 4.029 | CH3 | (CH3)2CH | CH2 | 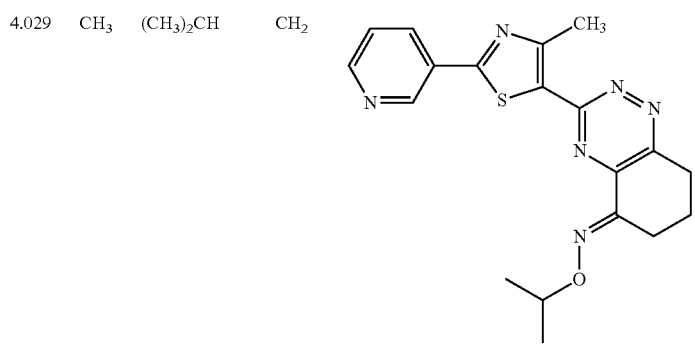 | |
| 4.030 | CH3 | CH2C=CH2 | CH2 | 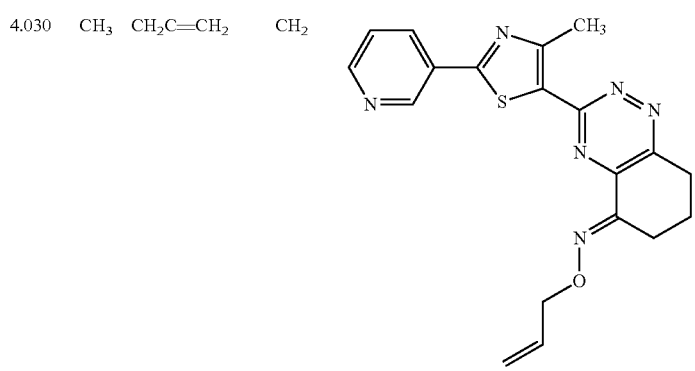 | |

TABLE 4-continued
Examples of compound of formula (Idd)
Formula Idd
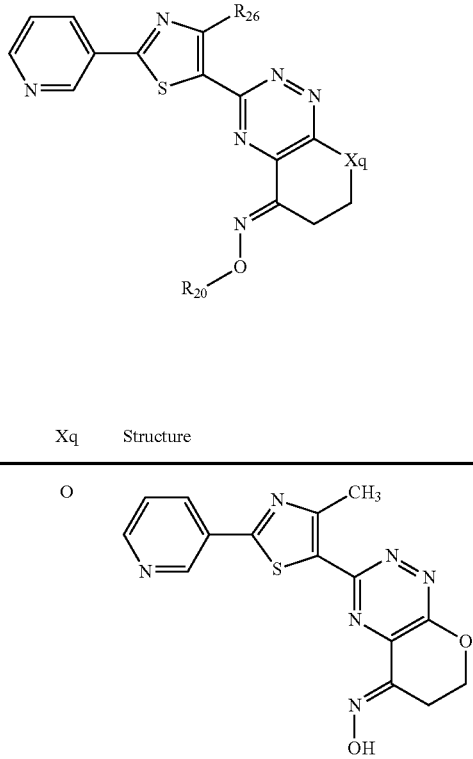
| Comp. No. | $R_{26}$ | $R_{20}$ | Xq | Structure | Phy. Data LCMS/NMR or Mpt |
|---|---|---|---|---|---|
| 4.031 | $CH_3$ | H | O | 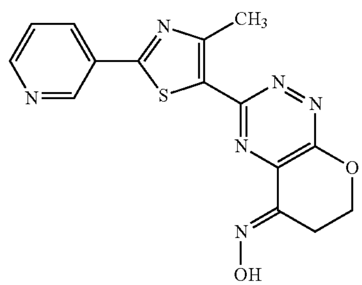 | |
| 4.032 | $CH_3$ | $CH_3$ | O | 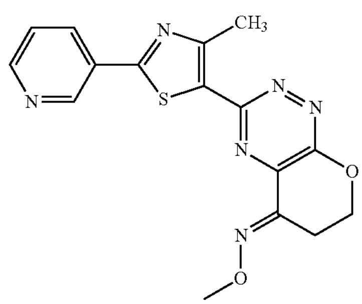 | |
| 4.033 | $CH_3$ | $CH_3CH_2$ | O | 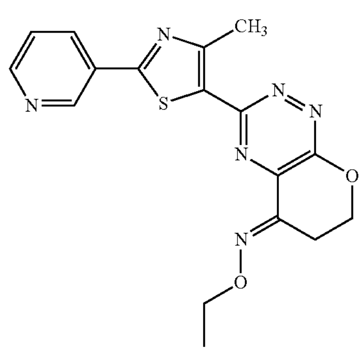 | |

TABLE 4-continued
Examples of compound of formula (Idd)
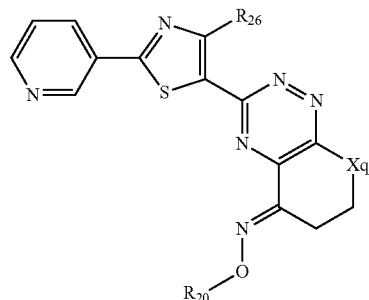
Formula Idd
| Comp. No. | R26 | R20 | Xq | Structure | Phy. Data LCMS/NMR or Mpt |
|---|---|---|---|---|---|
| 4.034 | CH₃ | CH₃CH₂CH₂ | O | 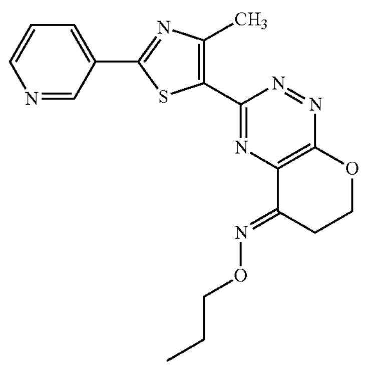 | |
| 4.035 | CH₃ | (CH₃)₂CH | O | 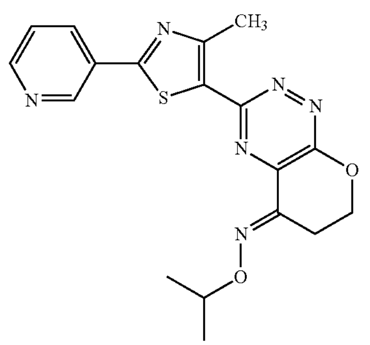 | |
| 4.036 | CH₃ | CH₂=CH₂ | O | 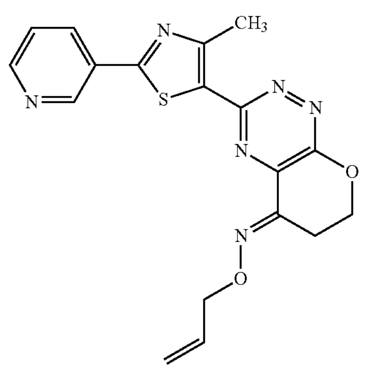 | |

TABLE 4-continued
Examples of compound of formula (Idd)
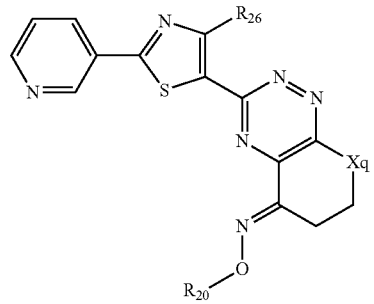
Formula Idd
| Comp. No. | R<sub>26</sub> | R<sub>20</sub> | Xq | Structure | Phy. Data LCMS/NMR or Mpt |
|---|---|---|---|---|---|
| 4.037 | $CH_3$ | H | N—$CH_3$ | 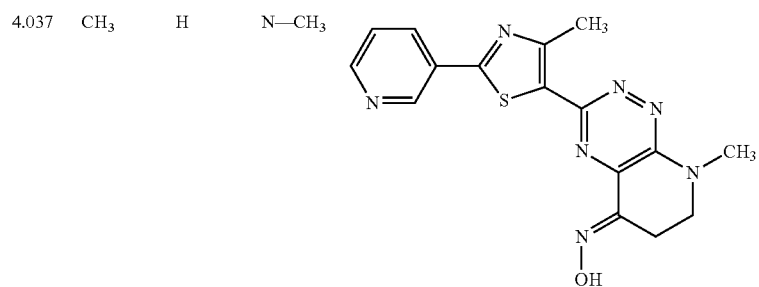 | |
| 4.038 | $CH_3$ | $CH_3$ | N—$CH_3$ | 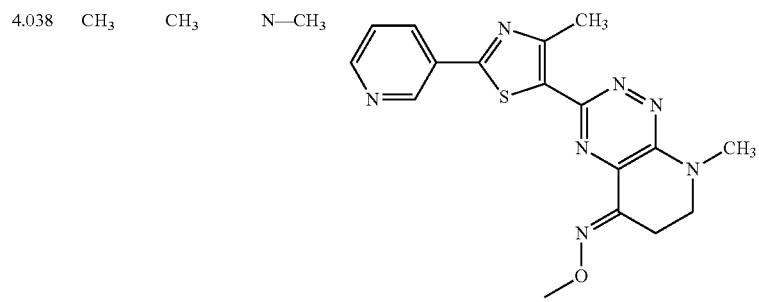 | |
| 4.039 | $CH_3$ | $CH_3CH_2$ | N—$CH_3$ | 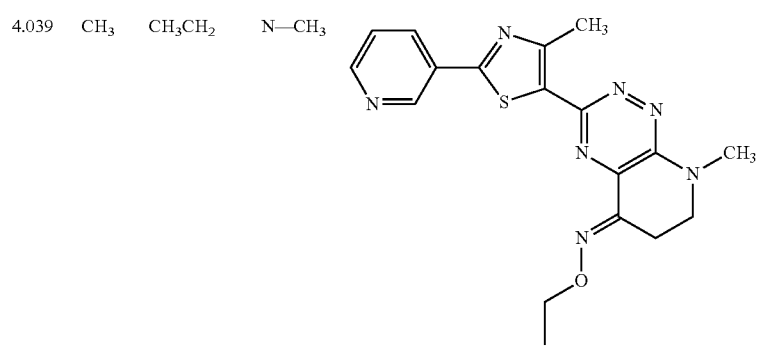 | |

TABLE 4-continued
Examples of compound of formula (Idd)
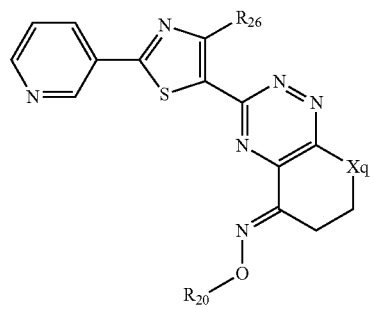
Formula Idd
| Comp. No. | R26 | R20 | Xq | Structure | Phy. Data LCMS/NMR or Mpt |
|---|---|---|---|---|---|
| 4.040 | CH3 | CH3CH2CH2 | N—CH3 | 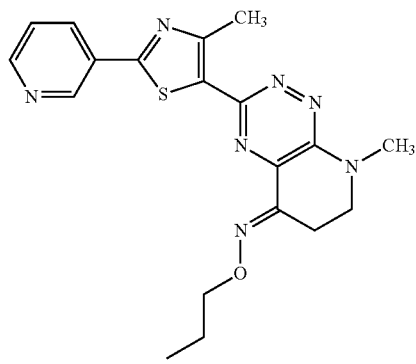 [SMILES: CCCO/N=C1\CCN(C)c2nnc(-c3sc(-c4cccnc4)nc3C)nc21] | |
| 4.041 | CH3 | (CH3)2CH | N—CH3 | 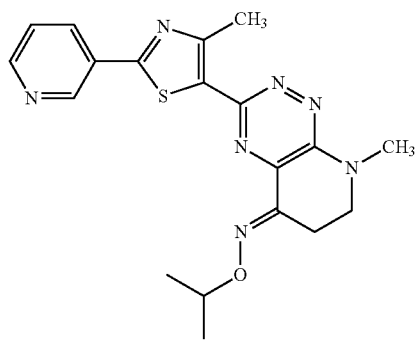 [SMILES: Cc1nc(-c2cccnc2)sc1-c1nnc2c(n1)/C(=N/OC(C)C)CCN2C] | |
| 4.042 | CH3 | CH2=CH2 | N—CH3 | 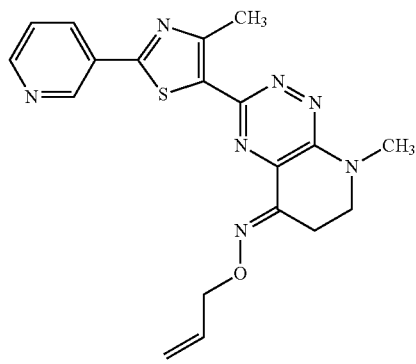 [SMILES: C=CCO/N=C1\CCN(C)c2nnc(-c3sc(-c4cccnc4)nc3C)nc21] | |

TABLE 4-continued

Examples of compound of formula (Idd)

Formula Idd

| Comp. No. | $R_{26}$ | $R_{20}$ | Xq | Structure | Phy. Data LCMS/NMR or Mpt |
|---|---|---|---|---|---|
| 4.043 | $CH_3$ | H | $N-SO_2CH_3$ | 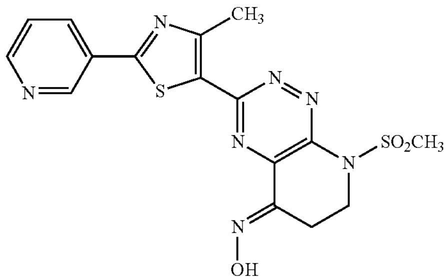 | |
| 4.044 | $CH_3$ | $CH_3$ | $N-SO_2CH_3$ | 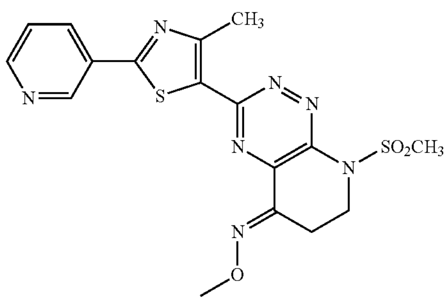 | |
| 4.045 | $CH_3$ | $CH_3CH_2$ | $N-SO_2CH_3$ | 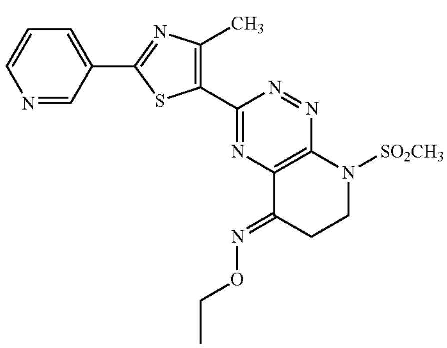 | |

TABLE 4-continued
Examples of compound of formula (Idd)
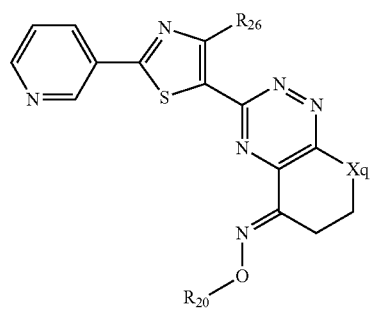
Formula Idd
| Comp. No. | $R_{26}$ | $R_{20}$ | Xq | Structure | Phy. Data LCMS/NMR or Mpt |
|---|---|---|---|---|---|
| 4.046 | $CH_3$ | $CH_3CH_2CH_2$ | $N—SO_2CH_3$ | 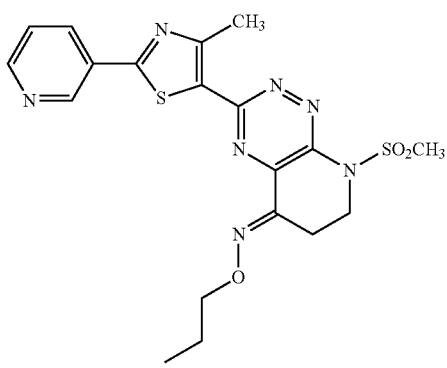 [SMILES: CCCO/N=C1\CCN(S(C)(=O)=O)c2nnc(-c3sc(-c4cccnc4)nc3C)nc21] | |
| 4.047 | $CH_3$ | $(CH_3)_2CH$ | $N—SO_2CH_3$ | 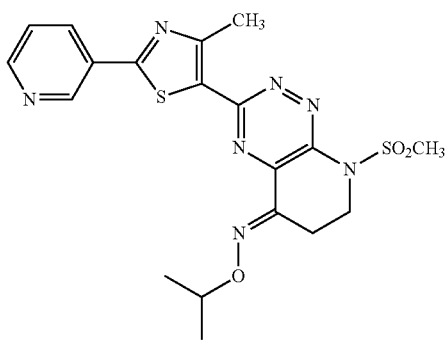 [SMILES: Cc1nc(-c2cccnc2)sc1-c1nnc2c(n1)/C(=N/OC(C)C)CCN2S(C)(=O)=O] | |
| 4.048 | $CH_3$ | $CH_2=CH_2$ | $N—SO_2CH_3$ | 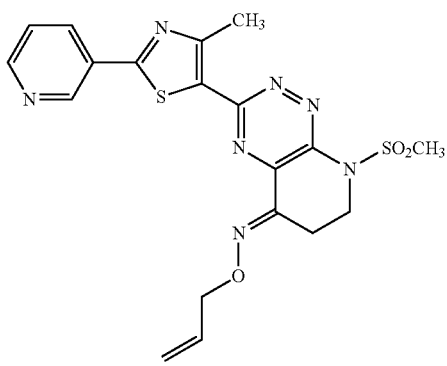 [SMILES: C=CCO/N=C1\CCN(S(C)(=O)=O)c2nnc(-c3sc(-c4cccnc4)nc3C)nc21] | |

TABLE 5
Examples of compound of formula (Iee)
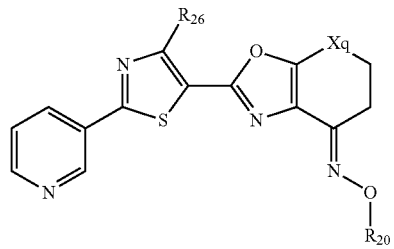
Formula Iee
| Comp. No. | R$_{24}$ | R$_{20}$ | Xq | Structure | Phy. Data LCMS/NMR or Mpt |
|---|---|---|---|---|---|
| 5.001 | H | H | CH$_2$ | 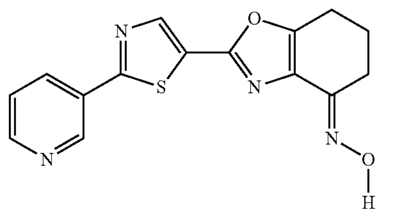 | |
| 5.002 | H | CH$_3$ | CH$_2$ | 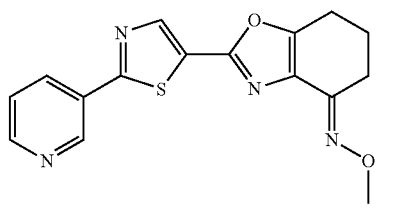 | |
| 5.003 | H | CH$_3$CH$_2$ | CH$_2$ | 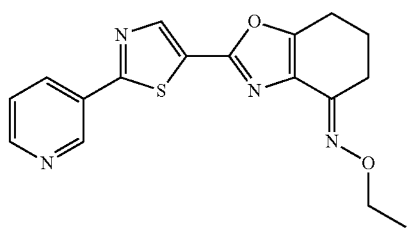 | |
| 5.004 | H | CH$_3$CH$_2$CH$_2$ | CH$_2$ | 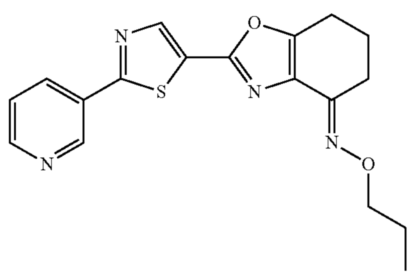 | |
| 5.005 | H | (CH$_3$)$_2$CH | CH$_2$ | 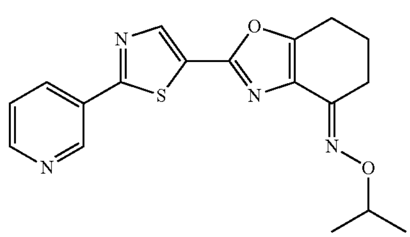 | |

TABLE 5-continued
Examples of compound of formula (Iee)
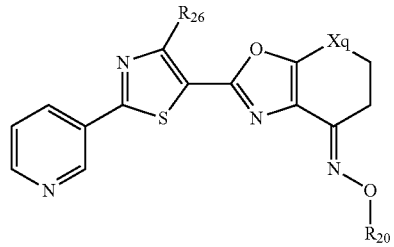
Formula Iee
| Comp. No. | R$_{24}$ | R$_{20}$ | Xq | Structure | Phy. Data LCMS/NMR or Mpt |
|---|---|---|---|---|---|
| 5.006 | H | CH$_2$C=CH$_2$ | CH$_2$ | 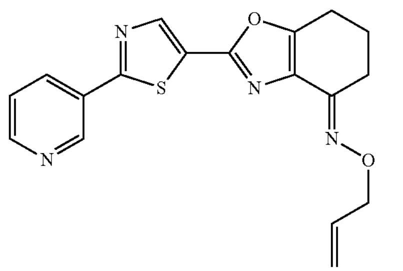 | |
| 5.007 | H | H | O | 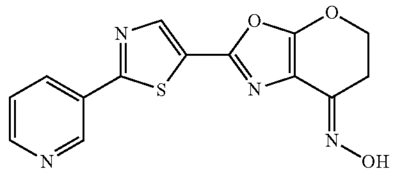 | |
| 5.008 | H | CH$_3$ | O | 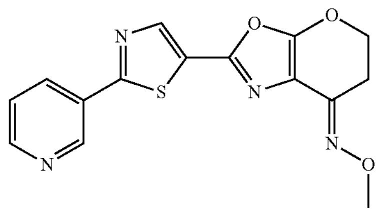 | |
| 5.009 | H | CH$_3$CH$_2$ | O | 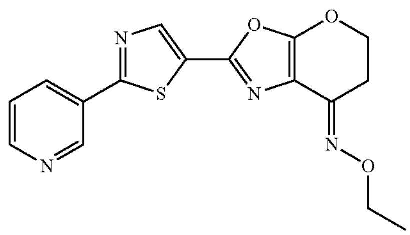 [SMILES: CCO/N=C1\CCOc2oc(-c3cnc(-c4cccnc4)s3)nc21] | |
| 5.01 | H | CH$_3$CH$_2$CH$_2$ | O | 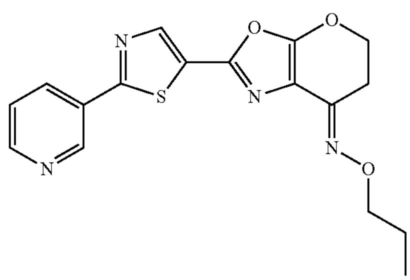 [SMILES: CCCO/N=C1\CCOc2oc(-c3cnc(-c4cccnc4)s3)nc21] | |

TABLE 5-continued
Examples of compound of formula (Iee)
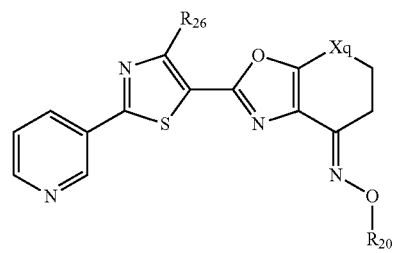
Formula Iee
| Comp. No. | R$_{24}$ | R$_{20}$ | Xq | Structure | Phy. Data LCMS/NMR or Mpt |
|---|---|---|---|---|---|
| 5.011 | H | (CH$_3$)$_2$CH | O | 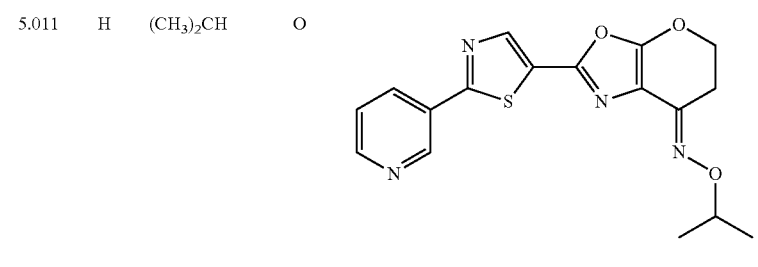 | |
| 5.012 | H | CH$_2$C=CH$_2$ | O | 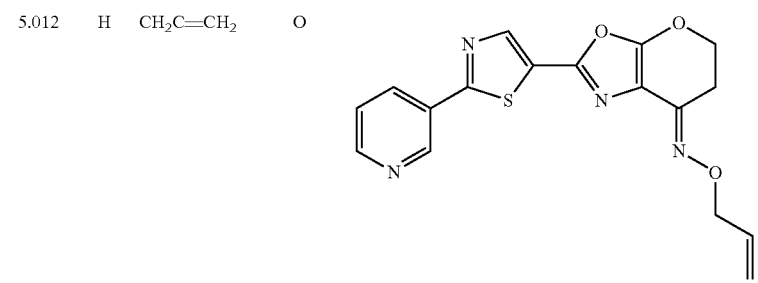 | |
| 5.013 | H | H | N—CH$_3$ | 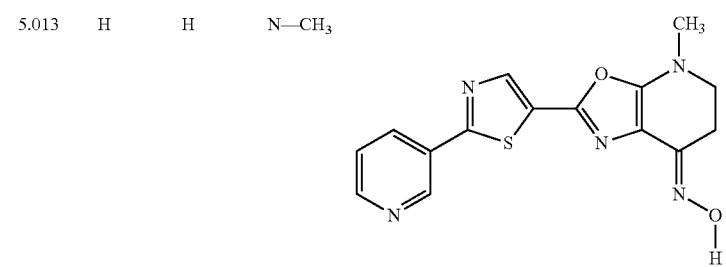 | |
| 5.014 | H | CH$_3$ | N—CH$_3$ | 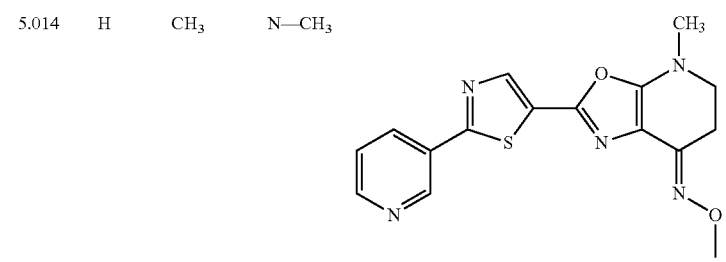 | |

TABLE 5-continued

Examples of compound of formula (Iee)

Formula Iee

| Comp. No. | R$_{24}$ | R$_{20}$ | Xq | Structure | Phy. Data LCMS/NMR or Mpt |
|---|---|---|---|---|---|
| 5.015 | H | CH$_3$CH$_2$ | N—CH$_3$ | 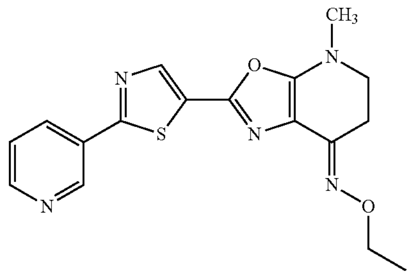 | |
| 5.016 | H | CH$_3$CH$_2$CH$_2$ | N—CH$_3$ | 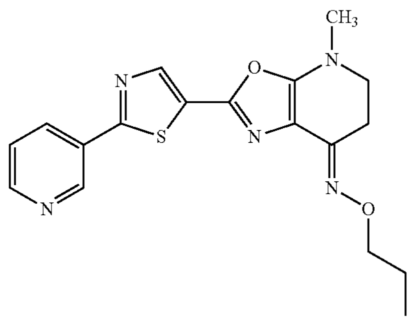 | |
| 5.017 | H | (CH$_3$)$_2$CH | N—CH$_3$ | 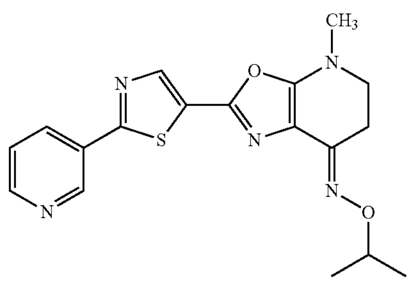 | |
| 5.018 | H | CH$_2$=CH$_2$ | N—CH$_3$ | 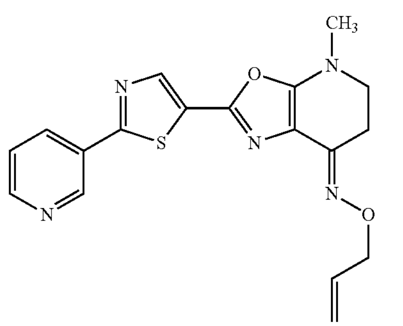 [SMILES: C=CCO/N=C1\CCN(C)c2oc(-c3cnc(-c4cccnc4)s3)nc21] | |

TABLE 5-continued
Examples of compound of formula (Iee)
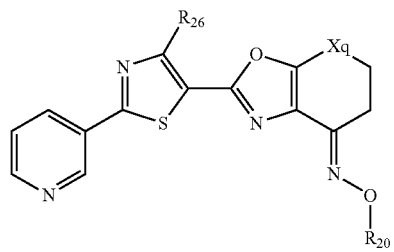
Formula Iee
| Comp. No. | R$_{24}$ | R$_{20}$ | Xq | Structure | Phy. Data LCMS/NMR or Mpt |
|---|---|---|---|---|---|
| 5.019 | H | H | N—SO$_2$CH$_3$ | 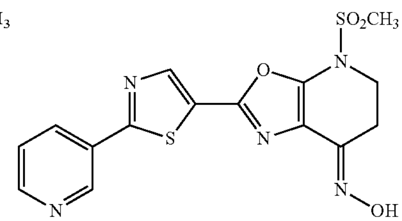 | |
| 5.020 | H | CH$_3$ | N—SO$_2$CH$_3$ | 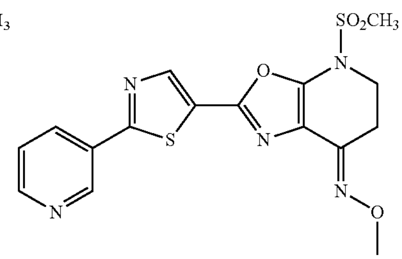 | |
| 5.021 | H | CH$_3$CH$_2$ | N—SO$_2$CH$_3$ | 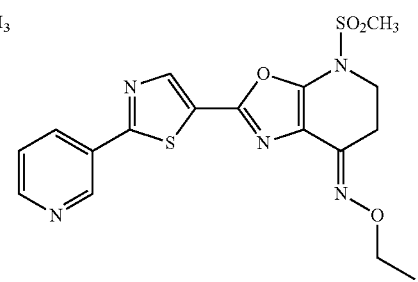 | |
| 5.022 | H | CH$_3$CH$_2$CH$_2$ | N—SO$_2$CH$_3$ | 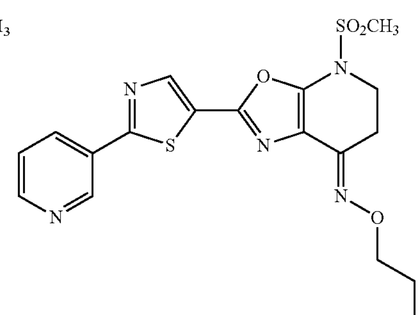 | |

TABLE 5-continued

Examples of compound of formula (Iee)

Formula Iee

| Comp. No. | $R_{24}$ | $R_{20}$ | $X_q$ | Structure | Phy. Data LCMS/NMR or Mpt |
|---|---|---|---|---|---|
| 5.023 | H | $(CH_3)_2CH$ | $N-SO_2CH_3$ | 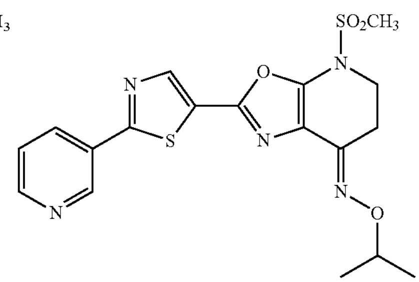 | |
| 5.024 | H | $CH_2C=CH_2$ | $N-SO_2CH_3$ | 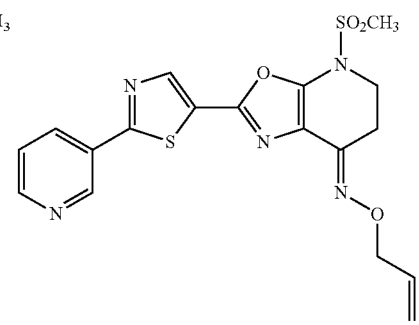 | |
| 5.025 | $CH_3$ | H | $CH_2$ | 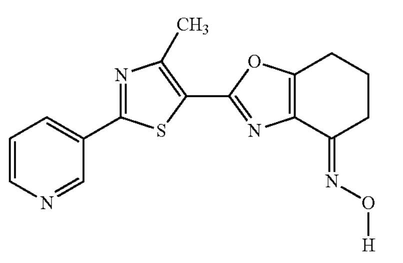 | |
| 5.026 | $CH_3$ | $CH_3$ | $CH_2$ | 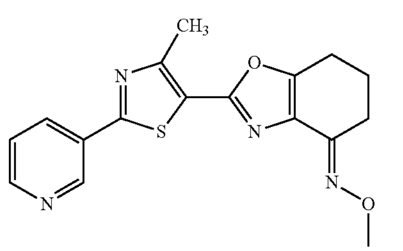 | |

TABLE 5-continued
Examples of compound of formula (Iee)
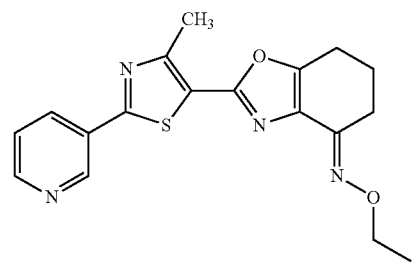
Formula Iee
| Comp. No. | R$_{24}$ | R$_{20}$ | Xq | Structure | Phy. Data LCMS/NMR or Mpt |
|---|---|---|---|---|---|
| 5.027 | CH$_3$ | CH$_3$CH$_2$ | CH$_2$ | 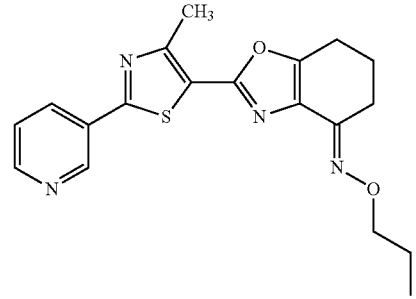 | |
| 5.028 | CH$_3$ | CH$_3$CH$_2$CH$_2$ | CH$_2$ | 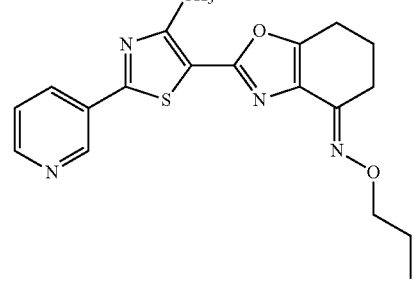 | |
| 5.029 | CH$_3$ | (CH$_3$)$_2$CH | CH$_2$ | 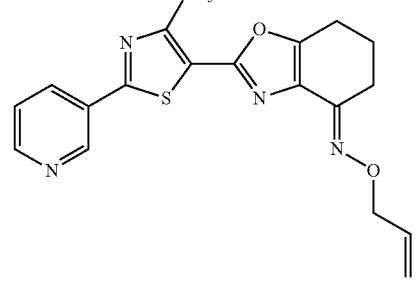 | |
| 5.030 | CH$_3$ | CH$_2$C=CH$_2$ | CH$_2$ | 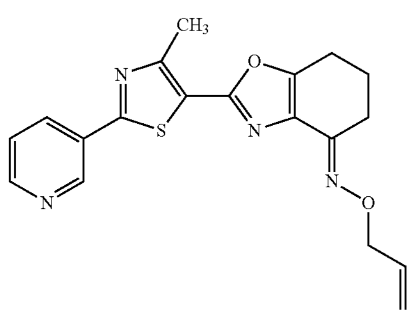 | |

TABLE 5-continued
Examples of compound of formula (Iee)
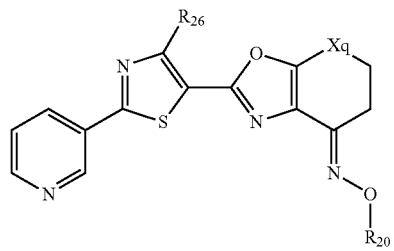
Formula Iee
| Comp. No. | $R_{24}$ | $R_{20}$ | Xq | Structure | Phy. Data LCMS/NMR or Mpt |
|---|---|---|---|---|---|
| 5.031 | $CH_3$ | H | O | 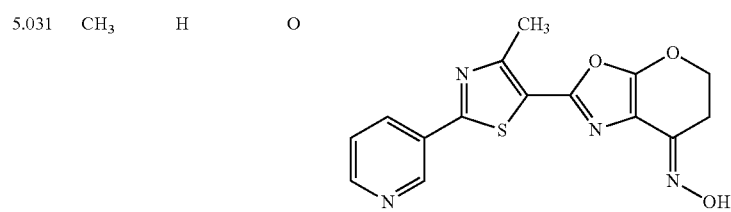 | |
| 5.032 | $CH_3$ | $CH_3$ | O | 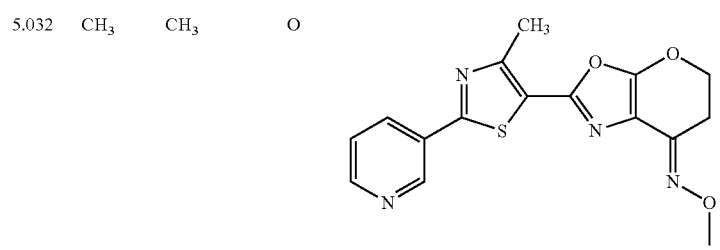 | |
| 5.033 | $CH_3$ | $CH_3CH_2$ | O | 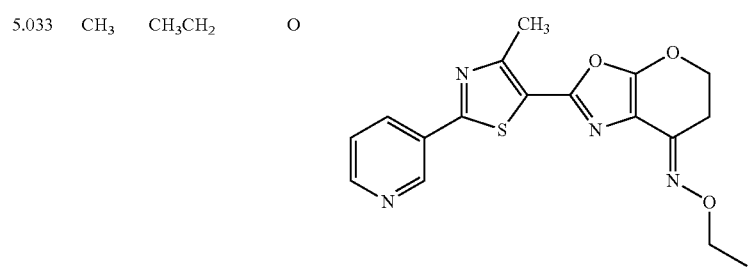 | |
| 5.034 | $CH_3$ | $CH_3CH_2CH_2$ | O | 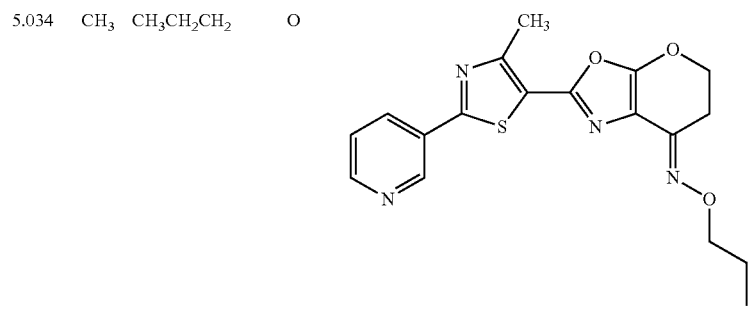 | |

TABLE 5-continued

Examples of compound of formula (Iee)

Formula Iee

| Comp. No. | $R_{24}$ | $R_{20}$ | Xq | Structure | Phy. Data LCMS/NMR or Mpt |
|---|---|---|---|---|---|
| 5.035 | $CH_3$ | $(CH_3)_2CH$ | O | 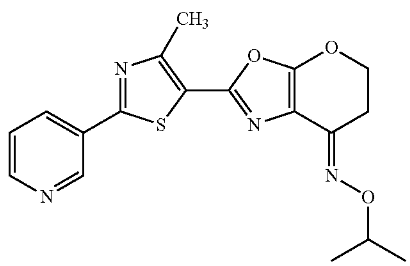 | |
| 5.036 | $CH_3$ | $CH_2C=CH_2$ | O | 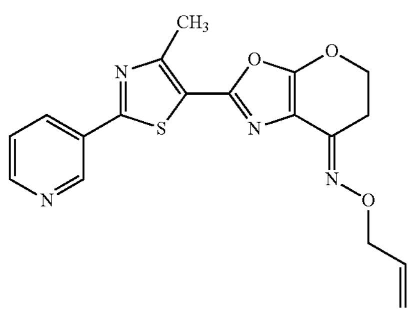 | |
| 5.037 | $CH_3$ | H | $N-CH_3$ | 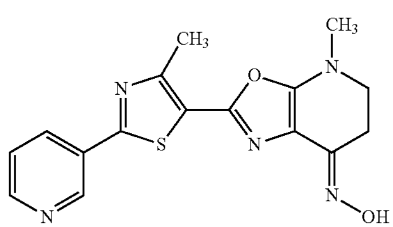 | |
| 5.038 | $CH_3$ | $CH_3$ | $N-CH_3$ | 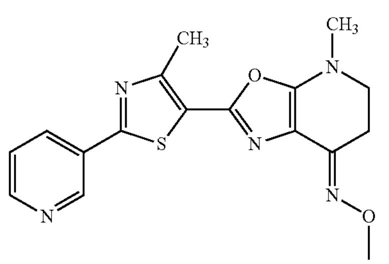 | |

TABLE 5-continued

Examples of compound of formula (Iee)

Formula Iee

| Comp. No. | $R_{24}$ | $R_{20}$ | Xq | Structure | Phy. Data LCMS/NMR or Mpt |
|---|---|---|---|---|---|
| 5.039 | $CH_3$ | $CH_3CH_2$ | N—$CH_3$ | 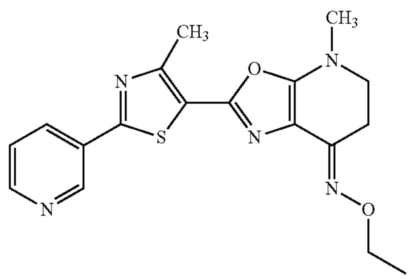 [SMILES: CCO/N=C1\CCN(C)c2oc(-c3sc(-c4cccnc4)nc3C)nc21] | |
| 5.040 | $CH_3$ | $CH_3CH_2CH_2$ | N—$CH_3$ | 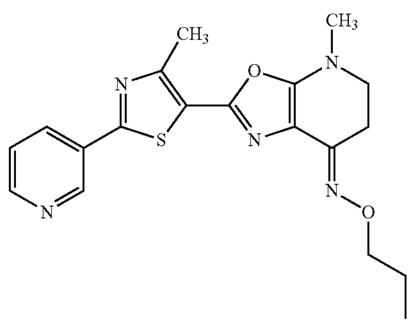 [SMILES: CCCO/N=C1\CCN(C)c2oc(-c3sc(-c4cccnc4)nc3C)nc21] | |
| 5.041 | $CH_3$ | $(CH_3)_2CH$ | N—$CH_3$ | 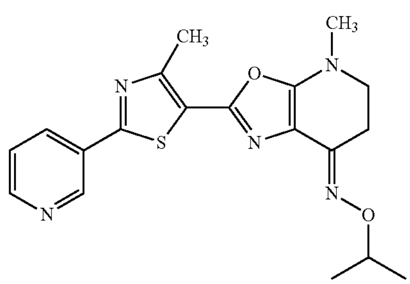 [SMILES: Cc1nc(-c2cccnc2)sc1-c1nc2c(o1)N(C)CC/C2=N\OC(C)C] | |
| 5.042 | $CH_3$ | $CH_2=CH_2$ | N—$CH_3$ | 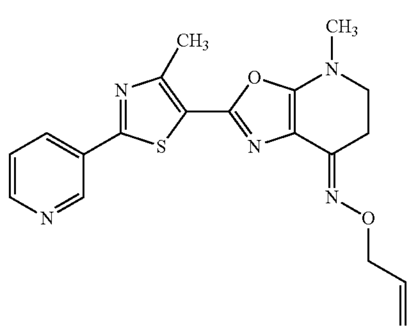 | |

TABLE 5-continued

Examples of compound of formula (Iee)

Formula Iee

| Comp. No. | $R_{24}$ | $R_{20}$ | Xq | Structure | Phy. Data LCMS/NMR or Mpt |
|---|---|---|---|---|---|
| 5.043 | $CH_3$ | H | $N-SO_2CH_3$ | 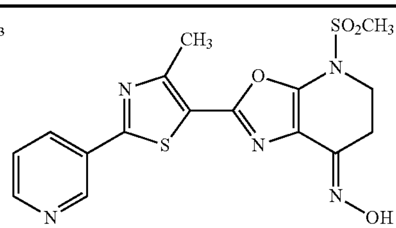 | |
| 5.044 | $CH_3$ | $CH_3$ | $N-SO_2CH_3$ | 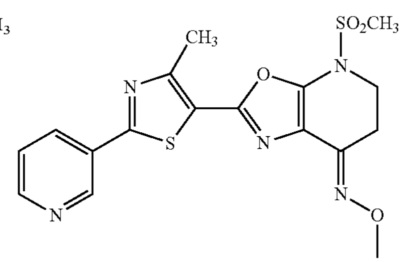 | |
| 5.045 | $CH_3$ | $CH_3CH_2$ | $N-SO_2CH_3$ | 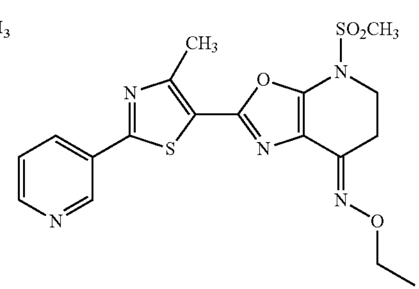 | |

TABLE 5-continued

Examples of compound of formula (Iee)

Formula Iee

| Comp. No. | R$_{24}$ | R$_{20}$ | Xq | Structure | Phy. Data LCMS/NMR or Mpt |
|---|---|---|---|---|---|
| 5.046 | CH$_3$ | CH$_3$CH$_2$CH$_2$ | N—SO$_2$CH$_3$ | 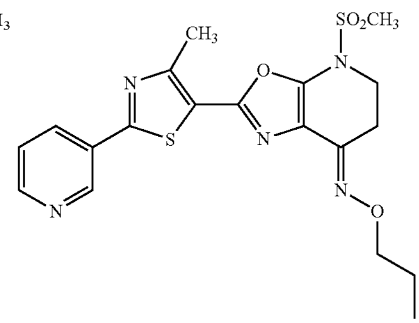 | |
| 5.047 | CH$_3$ | (CH$_3$)$_2$CH | N—SO$_2$CH$_3$ | 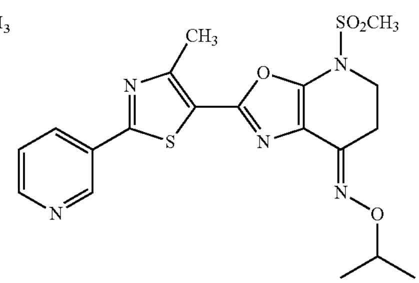 | |
| 5.048 | CH$_3$ | CH$_2$=CH$_2$ | N—SO$_2$CH$_3$ | 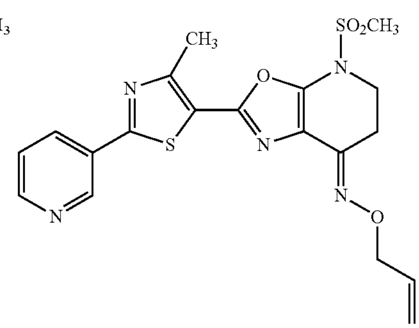 | |

TABLE 6
Examples of compound of formula (Iff)
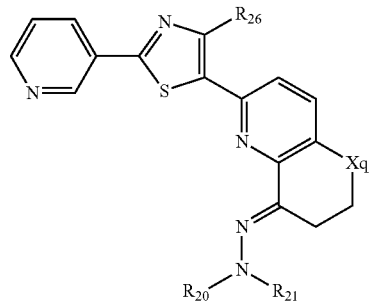
formula (Iff)
| Comp. No. | $R_{26}$ | $R_{20}$ | $R_{21}$ | Xq | Structure | Phys. Data LCMS/NMR or Mpt |
|---|---|---|---|---|---|---|
| 6.001 | H | H | H | $CH_2$ | 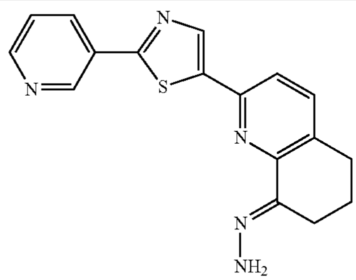 | |
| 6.002 | H | $CH_3$ | H | $CH_2$ | 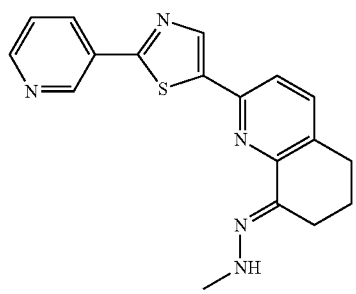 | |
| 6.003 | H | $CH_3$ | $CH_3$ | $CH_2$ | 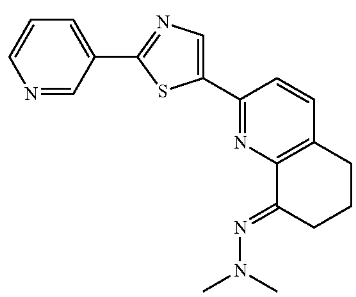 | |
| 6.004 | H | H | $CO_2CH_3$ | $CH_2$ | 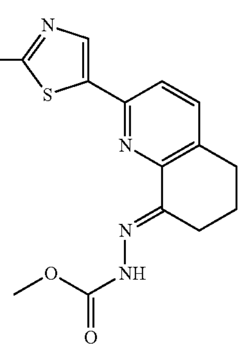 | |

TABLE 6-continued

Examples of compound of formula (Iff)

formula (Iff)

| Comp. No. | $R_{26}$ | $R_{20}$ | $R_{21}$ | Xq | Structure | Phys. Data LCMS/NMR or Mpt |
|---|---|---|---|---|---|---|
| 6.005 | H | $CH_3$ | $CO_2CH_3$ | $CH_2$ | 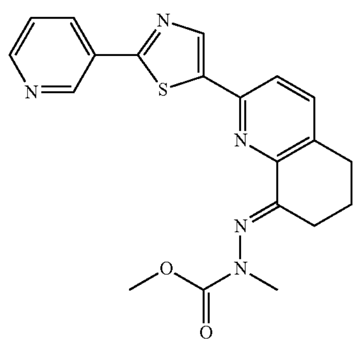 | |
| 6.006 | H | H | $SO_2CH_3$ | $CH_2$ | 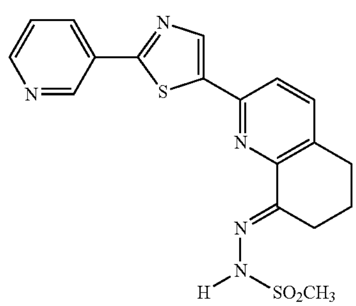 | |
| 6.007 | H | $CH_3$ | $SO_2CH_3$ | $CH_2$ | 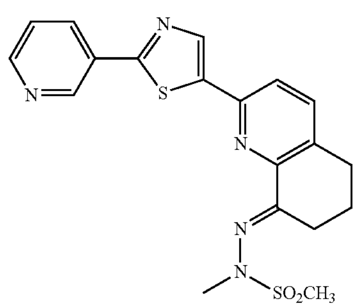 | |

TABLE 6-continued
Examples of compound of formula (Iff)
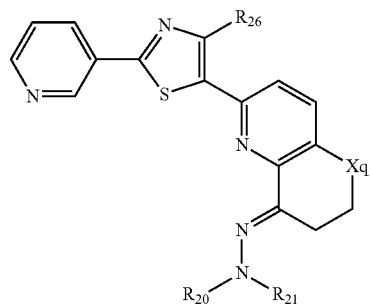
formula (Iff)
| Comp. No. | $R_{26}$ | $R_{20}$ | $R_{21}$ | Xq | Structure | Phys. Data LCMS/NMR or Mpt |
|---|---|---|---|---|---|---|
| 6.008 | $CH_3$ | H | H | $CH_2$ | 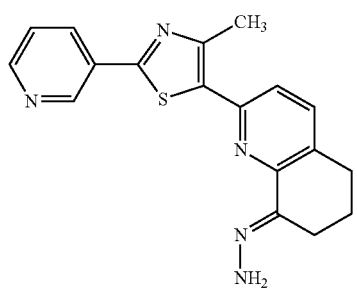 | |
| 6.009 | $CH_3$ | $CH_3$ | H | $CH_2$ | 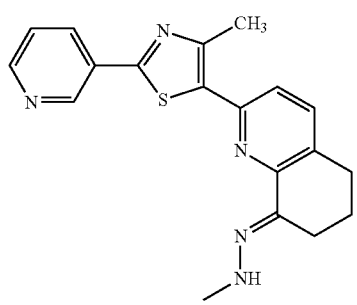 | LCMS: 1.49 min, 350 (M + 1). |
| 6.010 | $CH_3$ | $CH_3$ | $CH_3$ | $CH_2$ | 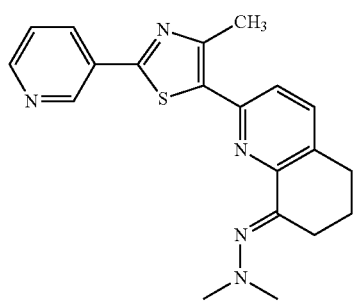 | LCMS: 1.84 min, 378 (M + 1). |

TABLE 6-continued
Examples of compound of formula (Iff)
formula (Iff)
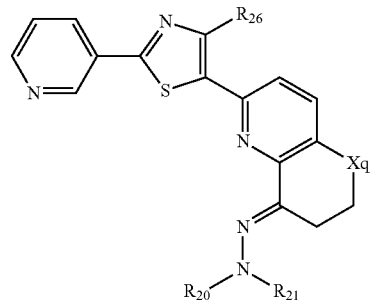
| Comp. No. | $R_{26}$ | $R_{20}$ | $R_{21}$ | $X_q$ | Structure | Phys. Data LCMS/NMR or Mpt |
|---|---|---|---|---|---|---|
| 6.011 | $CH_3$ | H | $CO_2CH_3$ | $CH_2$ | 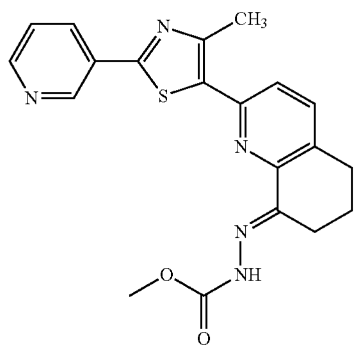 | $^1$H NMR (400 MHz, CHLOROFORM-d) σ ppm; 2.05 (quin, J = 6.0 Hz, 2 H); 2.78 (s, 3 H); 2.87 (br.s., 2 H); 2.94 (t, J = 6.0 Hz, 2 H); 3.91 (br.s., 3 H); 7.42 (dd, J = 7.70, 4.4 Hz, 1 H); 7.60 (d, J = 8.1 Hz, 1 H); 7.73 (d, J = 8.1 Hz, 1 H) 8.28 (d, J = 7.70 Hz, 1 H) 8.68 (d, J = 4.4 Hz, 1 H); 9.21 (br.s., 1 H); 14.01 (br.s., 1 H). Mp 194-200° C.; LCMS 0.94 min, 394 (M + 1) |
| 6.012 | $CH_3$ | $CH_3$ | $CO_2CH_3$ | $CH_2$ | 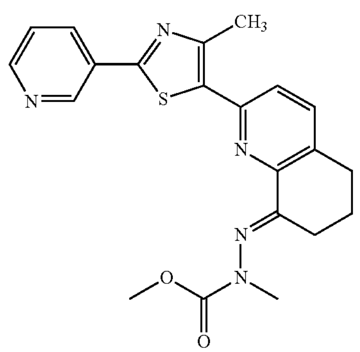 | |
| 6.013 | $CH_3$ | H | $SO_2CH_3$ | $CH_2$ | 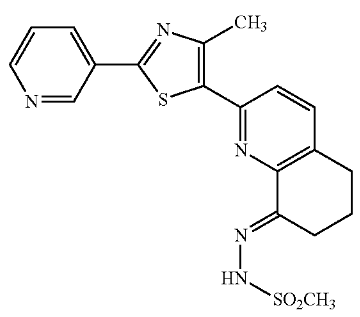 | |

TABLE 6-continued

Examples of compound of formula (Iff)

formula (Iff)

| Comp. No. | $R_{26}$ | $R_{20}$ | $R_{21}$ | Xq | Structure | Phys. Data LCMS/NMR or Mpt |
|---|---|---|---|---|---|---|
| 6.014 | CH$_3$ | CH$_3$ | SO$_2$CH$_3$ | CH$_2$ | 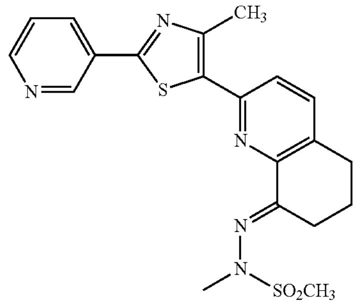 | |
| 6.015 | CH$_3$ | H | H | O | 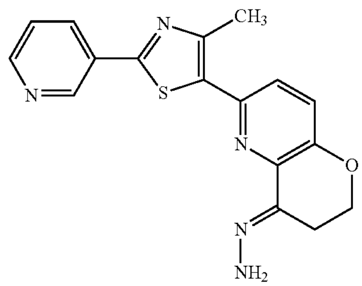 | |
| 6.016 | CH$_3$ | CH$_3$ | H | O | 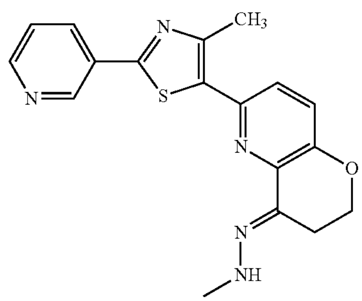 | Mpt 157-158° C. |
| 6.017 | CH$_3$ | CH$_3$ | CH$_3$ | O | 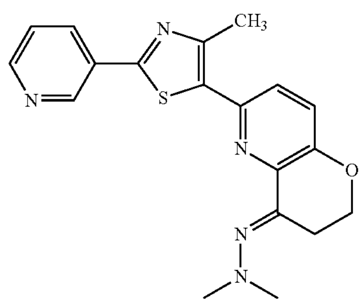 | |

TABLE 6-continued

Examples of compound of formula (Iff)

formula (Iff)

| Comp. No. | $R_{26}$ | $R_{20}$ | $R_{21}$ | Xq | Structure | Phys. Data LCMS/NMR or Mpt |
|---|---|---|---|---|---|---|
| 6.018 | $CH_3$ | H | $CO_2CH_3$ | O | 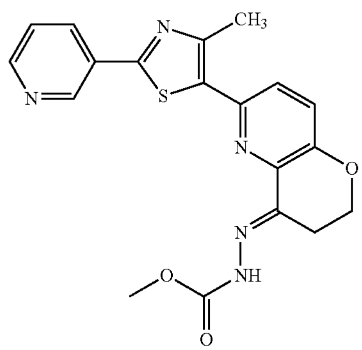 | Mpt 245-248° C. |
| 6.019 | $CH_3$ | $CH_3$ | $CO_2CH_3$ | O | 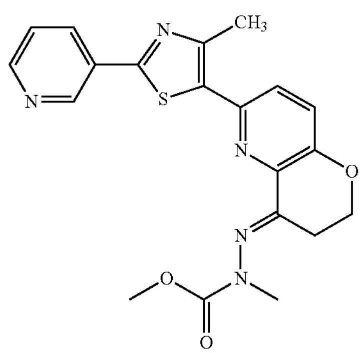 | Mpt 92-94° C. |
| 6.020 | $CH_3$ | H | $SO_2CH_3$ | O | 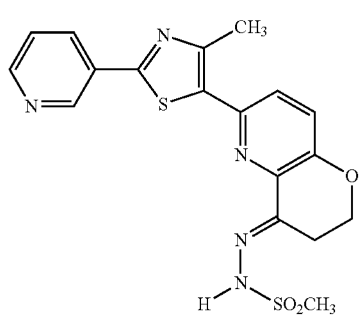 | Mpt 245-248° C. |

TABLE 6-continued

Examples of compound of formula (Iff)

formula (Iff)

| Comp. No. | R₂₆ | R₂₀ | R₂₁ | Xq | Structure | Phys. Data LCMS/NMR or Mpt |
|---|---|---|---|---|---|---|
| 6.021 | CH₃ | CH₃ | SO₂CH₃ | O | 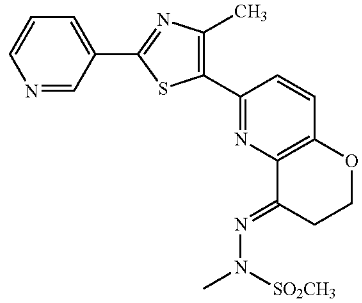 | Mpt 177-180° C. |
| 6.022 | CH₃ | H | H | N—CH₃ | 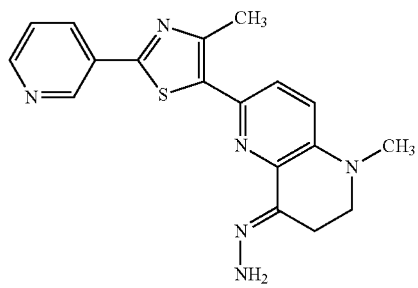 | |
| 6.023 | CH₃ | CH₃ | H | N—CH₃ | 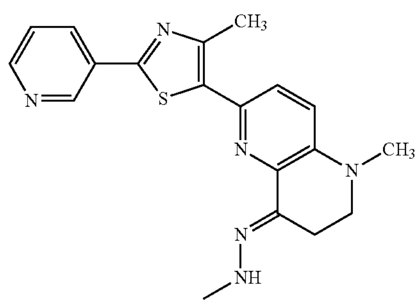 | |
| 6.024 | CH₃ | CH₃ | CH₃ | N—CH₃ | 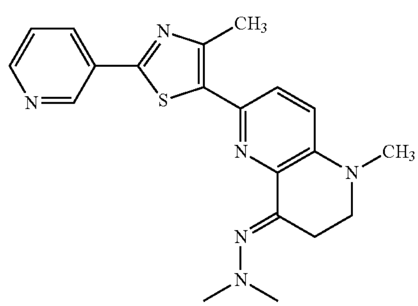 | |

TABLE 6-continued

Examples of compound of formula (Iff)

formula (Iff)

| Comp. No. | $R_{26}$ | $R_{20}$ | $R_{21}$ | Xq | Structure | Phys. Data LCMS/NMR or Mpt |
|---|---|---|---|---|---|---|
| 6.025 | CH$_3$ | H | CO$_2$CH$_3$ | N—CH$_3$ | 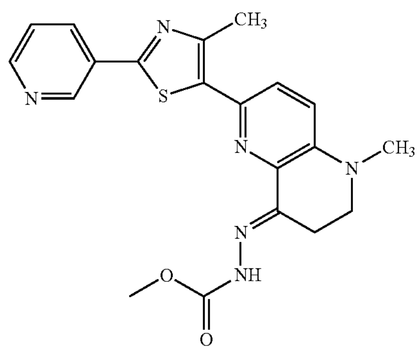 | |
| 6.026 | CH$_3$ | CH$_3$ | CO$_2$CH$_3$ | N—CH$_3$ | 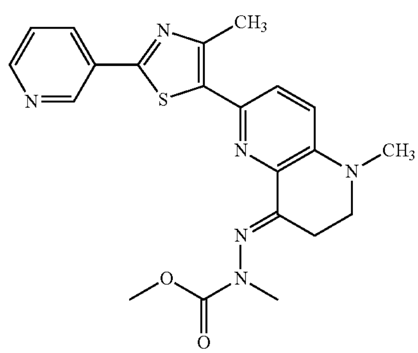 | |
| 6.027 | CH$_3$ | H | SO$_2$CH$_3$ | N—SO$_2$CH$_3$ | 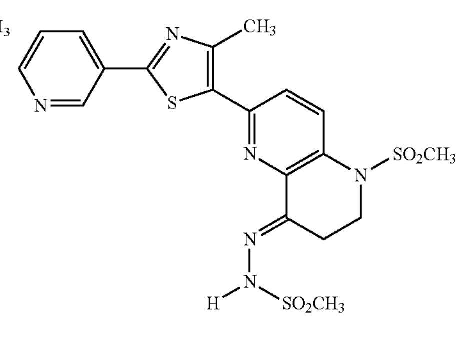 | |

TABLE 6-continued
Examples of compound of formula (Iff)
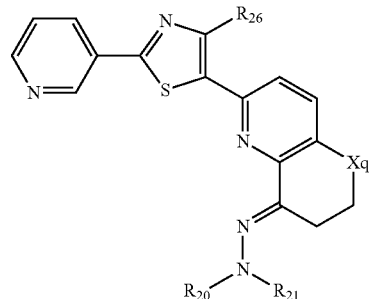
formula (Iff)
| Comp. No. | R26 | R20 | R21 | Xq | Structure | Phys. Data LCMS/NMR or Mpt |
|---|---|---|---|---|---|---|
| 6.028 | CH3 | CH3 | SO2CH3 | N—SO2CH3 | 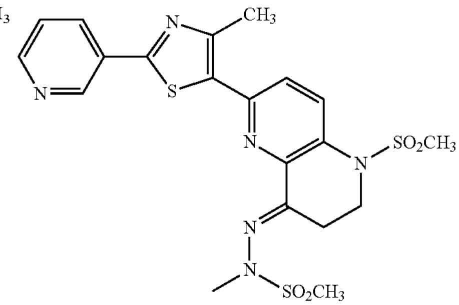 | |
| 6.029 | CH3 | H | 4-F-C6H4 | CH2 | 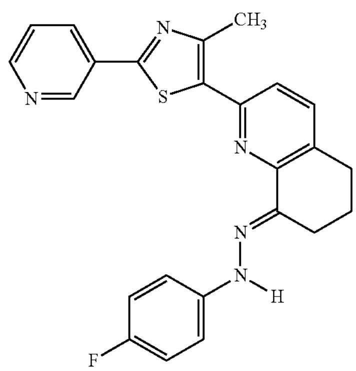 [SMILES: Cc1nc(-c2cccnc2)sc1-c1ccc2c(n1)/C(=N/Nc1ccc(F)cc1)CCC2] | LCMS: 2.27 min, 430 (M + 1). |
| 6.030 | CH3 | H | 2-OMe-C6H4 | CH2 | 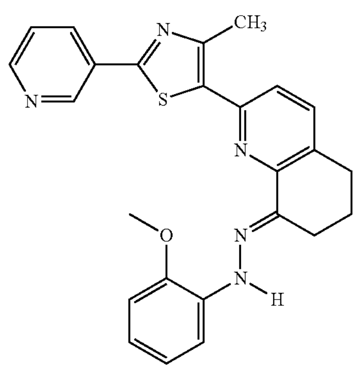 [SMILES: COc1ccccc1N/N=C1\CCCc2ccc(-c3sc(-c4cccnc4)nc3C)nc21] | LCMS: 1.81 min, 442 (M + 1). |

TABLE 6-continued
Examples of compound of formula (Iff)
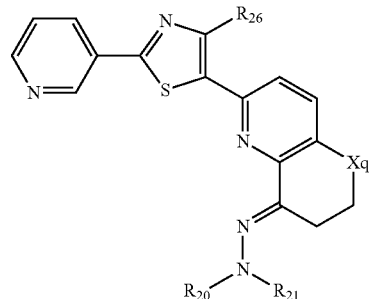
formula (Iff)
| Comp. No. | $R_{26}$ | $R_{20}$ | $R_{21}$ | Xq | Structure | Phys. Data LCMS/NMR or Mpt |
|---|---|---|---|---|---|---|
| 6.031 | $CH_3$ | H | 2-methoxyphenyl | $CH_2$ | 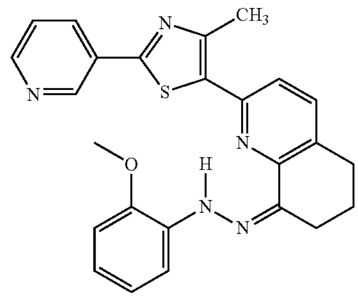 | LCMS: 2.16 min, 442 (M + 1). |
| 6.032 | $CH_3$ | H | 2,2,2-trifluoroethyl | $CH_2$ | 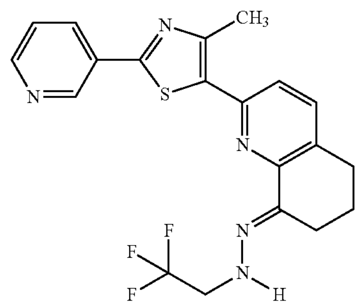 | LCMS: 1.37 min, 418 (M + 1). |
| 6.033 | $CH_3$ | H | 2,2,2-trifluoroethyl | $CH_2$ | 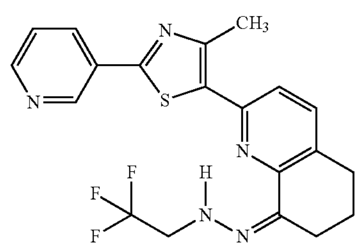 | LCMS: 1.83 min, 418 (M + 1). |

TABLE 6-continued
Examples of compound of formula (Iff)
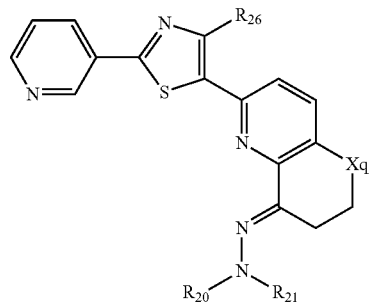
formula (Iff)
| Comp. No. | R26 | R20 | R21 | Xq | Structure | Phys. Data LCMS/NMR or Mpt |
|---|---|---|---|---|---|---|
| 6.034 | CH3 | H | 4-methoxyphenyl | CH2 | 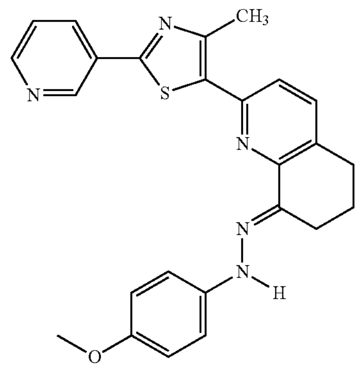 [SMILES: COc1ccc(N/N=C2\CCCc3ccc(-c4sc(-c5cccnc5)nc4C)nc32)cc1] | LCMS: 2.2 min, 442 (M + 1). |
| 6.035 | CH3 | H | tert-butyl | CH2 | 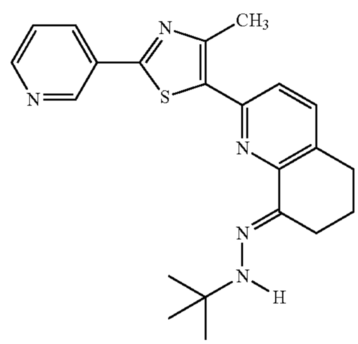 [SMILES: Cc1nc(-c2cccnc2)sc1-c1ccc2c(n1)/C(=N/NC(C)(C)C)CCC2] | LCMS: 2.12 min, 392 (M + 1). |
| 6.036 | CH3 | H | pyrimidin-2-yl | CH2 | 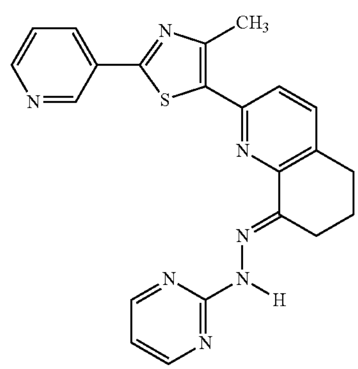 [SMILES: Cc1nc(-c2cccnc2)sc1-c1ccc2c(n1)/C(=N/Nc1ncccn1)CCC2] | LCMS: 1.43 min, 414 (M + 1). |

TABLE 6-continued
Examples of compound of formula (Iff)
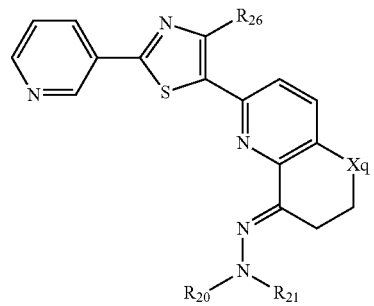
formula (Iff)
| Comp. No. | R26 | R20 | R21 | Xq | Structure | Phys. Data LCMS/NMR or Mpt |
|---|---|---|---|---|---|---|
| 6.037 | CH3 | H | 2-pyridyl | CH2 | 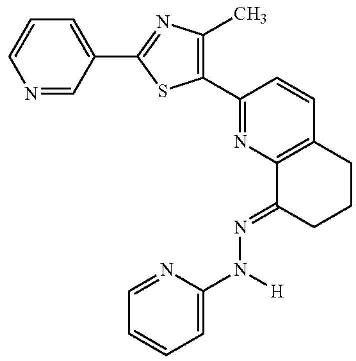 [SMILES: Cc1nc(-c2cccnc2)sc1-c1ccc2c(n1)/C(=N/Nc1ccccn1)CCC2] | LCMS: 0.95 min, 413 (M + 1). |
| 6.038 | CH3 | H | 2,4-difluorophenyl | CH2 | 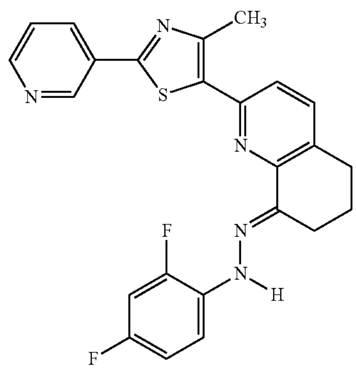 [SMILES: Cc1nc(-c2cccnc2)sc1-c1ccc2c(n1)/C(=N/Nc1ccc(F)cc1F)CCC2] | LCMS: 1.88 min, 448 (M + 1). |
| 6.039 | CH3 | H | 2-fluorophenyl | CH2 | 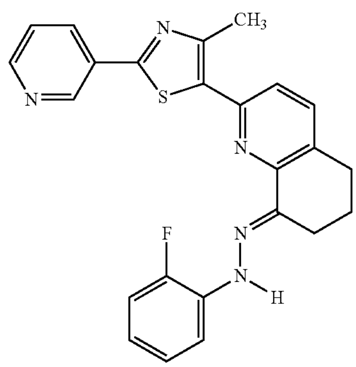 | LCMS: 2.26 min, 430 (M + 1). |

TABLE 6-continued
Examples of compound of formula (Iff)
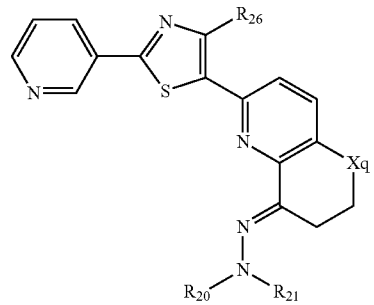
formula (Iff)
| Comp. No. | R26 | R20 | R21 | Xq | Structure | Phys. Data LCMS/NMR or Mpt |
|---|---|---|---|---|---|---|
| 6.040 | CH3 | H | 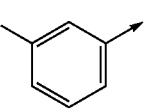 | CH2 | 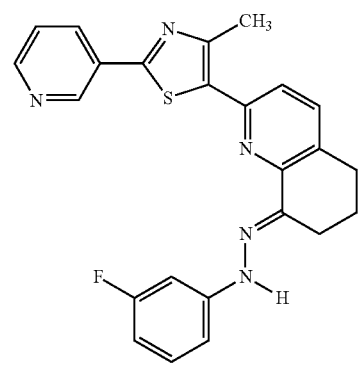 [SMILES: Cc1nc(-c2cccnc2)sc1-c1ccc2c(n1)/C(=N/Nc1cccc(F)c1)CCC2] | LCMS: 2.32 min, 430 (M + 1). |
| 6.041 | CH3 | H |  | CH2 | 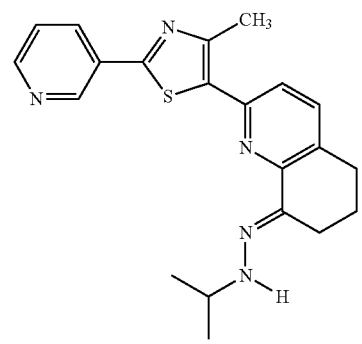 | LCMS: 2.32 min, 430 (M + 1). |

TABLE 7
Compounds of formula Igg
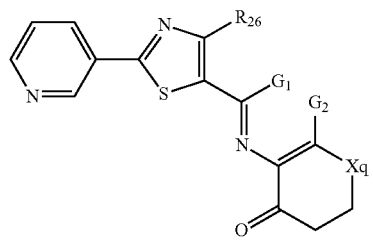
| Comp. No. | R26 | G1 | G2 | Xq | Structure | Phys. Data LCMS/NMR or Mpt |
|---|---|---|---|---|---|---|
| 7.001 | CH3 | CH | CH | CH2 | 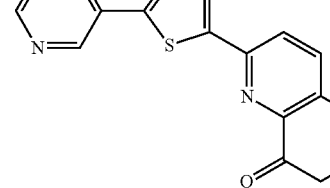 | $^1$H NMR (400 MHz, CHLOROFORM-d) σ ppm; 2.79 (s, 3 H); 2.84 (t, J = 6.42 Hz, 2 H); 3.07 (t, J = 6.42 Hz, 2 H); 7.35-7.43 (m, 1 H); 7.65-7.72 (m, 1 H); 7.72-7.78 (m, 1 H); 8.25 (d, J = 8.07 Hz, 1 H); 8.66 (d, J = 3.67 Hz, 1 H) 9.21 (s, 1 H). LCMS: 0.81 Min, 322 (M + 1). |
| 7.002 | H | CH | CH | CH2 | 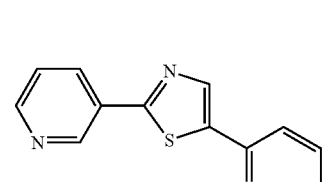 | LCMS: 0.76 min, 308 (M + 1). |
| 7.003 | CH3 | CH | CH | O | 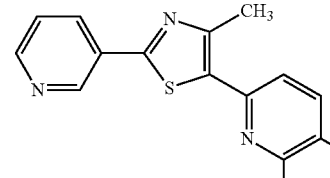 | |
| 7.004 | H | CH | CH | O | 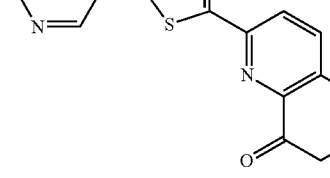 | $^1$H NMR (400 MHz, CHLOROFORM-d) σ ppm 2.76 (s, 3H); 3.02 (t, J = 6.6, 2H); 4.66 (t, J = 6.9, 2H); 7.49 (d, J = 9, 1H); 7.62-7.58 (m, 1H); 7.75 (d, J = 8.7, 1H); 8.45 (d, J = 7.8, 1H); 8.71(d, J = 3.9, 1H); 9.28 (s, 1 H). |

TABLE 7-continued
Compounds of formula Igg
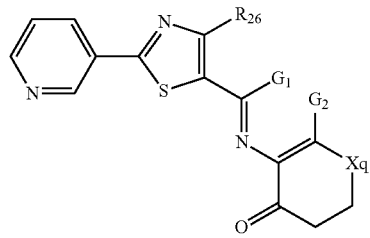
| Comp. No. | $R_{26}$ | $G_1$ | $G_2$ | Xq | Structure | Phys. Data LCMS/NMR or Mpt |
|---|---|---|---|---|---|---|
| 7.005 | $CH_3$ | CH | CH | NH | 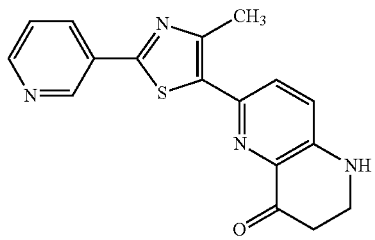 [SMILES: Cc1nc(-c2cccnc2)sc1-c1ccc2c(n1)C(=O)CCN2] | |
| 7.006 | H | CH | CH | NH | 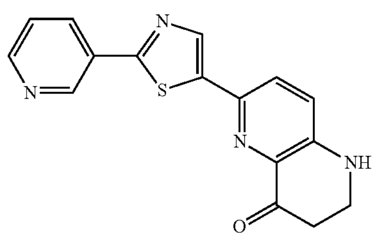 [SMILES: O=C1CCNc2ccc(-c3cnc(-c4cccnc4)s3)nc21] | |
| 7.007 | $CH_3$ | CH | CH | $N-CH_3$ | 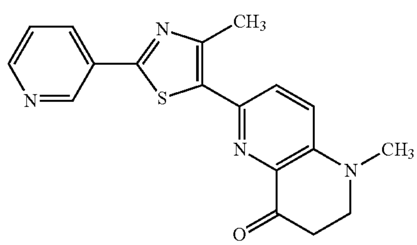 [SMILES: Cc1nc(-c2cccnc2)sc1-c1ccc2c(n1)C(=O)CCN2C] | |
| 7.008 | H | CH | CH | $N-CH_3$ | 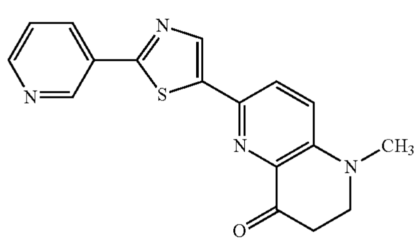 [SMILES: CN1CCC(=O)c2nc(-c3cnc(-c4cccnc4)s3)ccc21] | |
| 7.009 | $CH_3$ | CH | CH | $NSO_2CH_3$ | 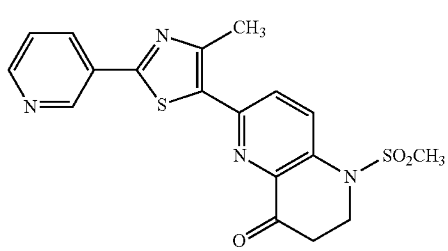 [SMILES: Cc1nc(-c2cccnc2)sc1-c1ccc2c(n1)C(=O)CCN2S(C)(=O)=O] | |

TABLE 7-continued

Compounds of formula Igg

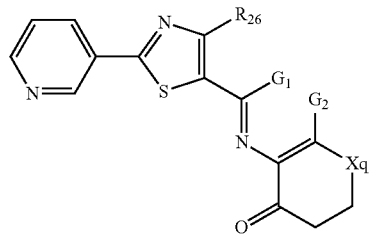

| Comp. No. | $R_{26}$ | $G_1$ | $G_2$ | $Xq$ | Structure | Phys. Data LCMS/NMR or Mpt |
|---|---|---|---|---|---|---|
| 7.010 | H | CH | CH | $NSO_2CH_3$ | 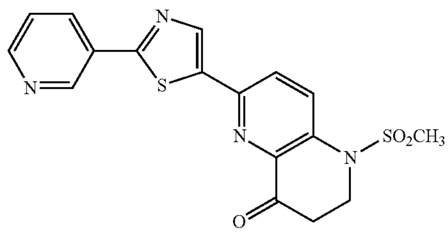 [SMILES: CS(=O)(=O)N1CCC(=O)c2nc(-c3cnc(-c4cccnc4)s3)ccc21] | |
| 7.011 | $CH_3$ | S | — | S | 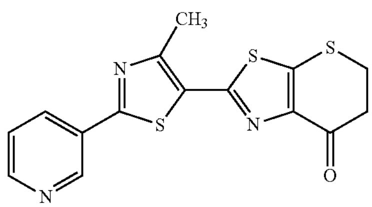 [SMILES: Cc1nc(-c2cccnc2)sc1-c1nc2c(s1)SCCC2=O] | $^1$H NMR (400 MHz, CHLOROFORM-d) σ ppm: 2.79 (s, 3 H), 3.04 (t, 2 H), 3.46 (t, 2 H), 7.43-7.45 (m, 1H), 8.43 (d, 1H), 8.69 (d, 1H), 9.20(s, 1H). |

$^1$H NMR Measurements: Measured on a Brucker 400 MHz spectrometer, chemical shifts given in ppm relevant to a TMS standard. Spectra measured in solvents indicated.

LCMS Method:

LCMS. Spectra were recorded on a ACQUITY SQD Mass Spectrometer (Waters Corp. Milford, Mass., USA) mass spectrometer equipped with an electrospray source (ESI; source temperature 150° C.; desolvation temperature 200° C.; cone voltage 30 V; cone gas flow 0 L/h, desolvation gas flow 650 L/h, mass range: 100 to 900 Da) and a Waters ACQUITY UPLC (column: Phenomenex Gemini C18, 3 µm, 30×2 mm (Phenomenex, Torrance, Calif., USA)); column temperature: 60° C.; flow rate 0.85 mL/min; eluent A: Water/Methanol 95:5, 0.05% formic acid; eluent B: Acetonitrile, 0.05% formic acid; gradient: 0 min 100% A; 0-1.2 min 100% A; 1.2-1.5 min 100% B; UV-detection: 210-500 nm, resolution 2 nm. The flow was split postcolumn prior to MS analysis.

FORMULATION EXAMPLES

%=Percent by Weight

Example F1

Emulsion Concentrates a) b) c)

| | | | |
|---|---|---|---|
| Active ingredient | 25% | 40% | 50% |
| Calcium dodecylbenzenesulfonate | 5% | 8% | 6% |

-continued

| | | | |
|---|---|---|---|
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

Solutions a) b) c) d)

| | | | | |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

Granules a) b) c) d)

| Active ingredient | 5% | 10% | 8% | 21% |
|---|---|---|---|---|
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

Dusts a) b)

| Active ingredient | 2% | 5% |
|---|---|---|
| Highly disperse silica | 1% | 5% |
| Talc | 97% | — |
| Kaolin | — | 90% |

Ready-to-use dusts are obtained by intimately mixing the carriers and the active ingredient.

Example F5

Wettable Powders a) b) c)

| Active ingredient | 25% | 50% | 75% |
|---|---|---|---|
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

Suspension Concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridyl-methyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 7 of the present invention"):
an adjuvant selected from the group of substances consisting of petroleum oils (alternative name) (628)+TX,
an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl- N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50,439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, ometothoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanfi* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methyl-rhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2](free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H naphtho [2,1-b]pyrano[3,4-e]pyran-4-yl]methyl-cyclopropanecarboxylate [915972-17-7]+TX and 1,3,5-trimethyl-N-(2-methyl-1-oxo-propyl)-N-[3-(2-methylpropyl)-4-[2,2,2-trifluoro-1-meth-oxy-1-(trifluoromethyl)ethyl]phenyl]-1H-pyrazole-4-car-boxamide [926914-55-8]+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood-.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1-7 with active ingredients described above comprises a compound selected from Tables 1-7 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures as described above can be used in a method for controlling pests, which comprises applying a composition comprising a mixture as described above to the pests or their environment, with the exception of a method for treatment of the human or animal body by surgery or therapy and diagnostic methods practiced on the human or animal body.

The mixtures comprising a compound of formula I selected from Tables 1-7 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1-7 and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scatte-ring or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

BIOLOGICAL EXAMPLES

Example B1

Activity Against *Myzus persicae* (Green Peach Aphid)

Sunflower leaf discs were placed on agar in a 24-well microtiter plate and sprayed with test solutions. After drying, the leaf discs were infested with an aphid population of mixed ages. After an incubation period of 6 days, samples were checked for mortality. In this test, compounds No. 1.026, 1.027, 1.030, 1.029, 1.028, 1.025, 1.049, 1.003, 1.032, 1.033, 1.036, 1.002, 1.051, 1.050, 1.054, 1.062, 1.063, 1.064, 1.053, 1.066, 1.068, 1.035, 3.050, 3.053, 3.051, 6.011, 6.029, 6.032, 6.033, 6.034, 6.035, 6.009, 6.016 and 6.019 showed an activity of over 80% at a concentration of 200 ppm.

Example B2

Activity Against *Bemisia tabaci* (Cotton White Fly)

Cotton leaf discs were placed on agar in a 24-well microtiter plate and sprayed with test solutions. After drying, the leaf discs were infested with 12 to 18 adults. After an incubation period of 6 days after infestation, samples were checked for mortality and special effects (e.g. phytotoxicity). In this test, compounds No. 1.026, 1.027, 1.030, 1.029, 1.028, 1.025, 1.049, 1.003, 1.032, 1.033, 1.036, 1.002, 1.035, 3.050, 3.053, 3.051, 6.011, 6.018, 6.021 and 6.019 showed an activity of over 80% at a concentration of 200 ppm.

Example B3

Activity Against *Spodoptera littoralis* (Egyptian Cotton Leaf Worm)

Test compounds were applied by pipette into 24 well plates and mixed with agar. Lettuce seeds were placed on the agar and the multi well plate is closed by another plate which contains also agar. After 7 days the roots have absorbed the compound and the lettuce has grown into the lid plate. The lettuce leafs were now cut off into the lid plate. *Spodoptera* eggs were pipetted through a plastic stencil on a humid gel blotting paper and the plate closed with it. The samples are checked for mortality, repellent effect, feeding behavior, and growth regulation 5 days after infestation. In this test, compounds No. 1.050, 1.052, 1.053 and 1.067 showed an activity of over 80% at a concentration of 12.5 ppm.

Example B4

Activity Against *Heliothis virescens* (Tobacco Budworm)

Eggs (0-24 h old) are placed in 24-well microtiter plate on artificial diet and treated with test solutions by pipetting. After an incubation period of 4 days, samples are checked for egg mortality, larval mortality, and growth regulation. In this test, compounds No. 1.002, 6.033 and 1.065 showed an activity of over 80% at a concentration of 200 ppm.

Example B5

Activity Against *Frankliniella occidentalis* (Western Flower Thrips)

Sunflower leaf discs are placed on agar in a 24-well microtiter plate and sprayed with test solutions. After drying, the leaf discs are infested with a *Frankliniella* population of mixed ages. After an incubation period of 7 days after treatment, samples are checked for mortality and special effects (e.g. phytotoxicity). In this test, compound No. 1.002 showed an activity of over 80% at a concentration of 200 ppm.

Example B6

Activity Against *Tetranychus urticae* (Two-Spotted Spider Mite)

Bean leaf discs on agar in 24-well microtiter plates are sprayed with test solutions. After drying, the leaf discs are infested with mite populations of mixed ages. 8 days later, discs are checked for egg mortality, larval mortality, and adult mortality. In this test In this test, compounds No. 1.028 and 1.063 showed an activity of over 80% at a concentration of 200 ppm.

Example B7

*Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Mortality was assessed at 24 and 48 hours after introduction. The following compounds gave at least 80% control of *Aedes aegypti* after 48 h and/or 24 h: No. 1.026, 1.027, 1.030 and 1.025.

Example B8

*Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Mortality was assessed at 24 and 48 hours after introduction. The following compounds gave at least 80% control of *Anopheles stephensi* after 48 h and/or 24 h: No. 1.026 and 1.030.

What is claimed is:
1. A compound of formula I

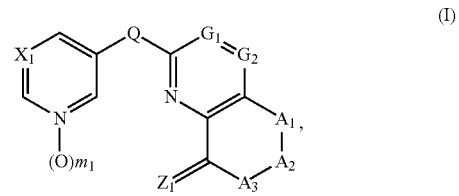

wherein
$X_1$ is nitrogen or $CR_1$;
$G_1$ is nitrogen or $CR_2$;
$G_2$ is nitrogen or $CR_3$;
or $G_1$-$G_2$ together is —S—, —O—, —NH—, or N—$CH_3$;
$A_1$ is oxygen, $S(O)n_1$, $S(O)(=NR_4)$, C=O, $NR_5$, $CR_6R_7$, —$CR_8CR_9$— or a direct bond;
$A_2$ is oxygen, $S(O)n_2$, $NR_{10}$ or $CR_{11}R_{12}$;
$A_3$ is oxygen, $NR_{13}$, $CR_{14}R_{15}$ or —$CR_{16}CR_{17}$—;
or $A_2$-$A_3$ together represents a group —$CR_{18}$=$CR_{19}$—;

with the provisos that;
a) not more than 1 substituent A can be oxygen or sulpher, and
b) not more than 2 substituents A can be nitrogen
c) 2 substituents A as nitrogen can be adjacent to each other or separated by a sulphur or carbon substituent;

$R_1$ is hydrogen or halogen;

$R_2$ and $R_3$, independently from each other, are hydrogen, halogen, $C_1$-$C_3$alkyl or $C_1$-$C_3$haloalkyl;

$R_4$, $R_5$, $R_{10}$ and $R_{13}$, independently from each other, are hydrogen, cyano, $C_1$-$C_2$alkyl, $C_3$-$C_6$cycloalkyl, $C_1$-$C_2$haloalkyl, C(O)$C_1$-$C_3$alkyl, (CO)O$C_1$-$C_3$alkyl, $SO_2$NH$C_1$-$C_3$alkyl, $SO_2$N($C_1$-$C_3$alkyl), $SO_2$$C_1$-$C_3$alkyl, $SO_2$-phenyl, wherein the said phenyl can be mono- or polysubstituted on the phenyl ring by substituents selected from the group consisting of $C_1$-$C_3$alkyl, $C_1$-$C_3$haloalkyl, $C_1$-$C_3$alkoxy, $C_1$-$C_3$haloalkoxy, halogen, cyano and nitro;

$R_6$, $R_7$, $R_8$, $R_9$, $R_{11}$, $R_{12}$, $R_{14}$, $R_{15}$, $R_{16}$ and $R_{17}$, independently from each other, are hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_1$-$C_4$alkylcarbonyl, $C_1$-$C_6$alkoxycarbonyl, $C_1$-$C_6$alkylaminocarbonyl, $C_3$-$C_6$dialkylaminocarbonyl, $C_1$-$C_6$alkoxycarbonyloxy, $C_1$-$C_6$alkylaminocarbonyloxy, $C_3$-$C_6$dialkylaminocarbonyloxy, $C_1$-$C_4$alkoxyimino-$C_1$-$C_4$alkyl, —CONHSO$_2$—$C_1$-$C_6$-alkyl, —CONHSO$_2$N($C_1$-$C_6$-alkyl)$_2$, or are a three- to ten-membered, monocyclic or fused bicyclic ring system which may be aromatic, partially saturated or fully saturated, said three- to ten-membered, monocyclic or fused bicyclic ring system can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_1$-$C_4$alkylcarbonyl, $C_1$-$C_6$alkoxycarbonyl, $C_1$-$C_6$alkylaminocarbonyl, and $C_2$-$C_8$dialkylaminocarbonyl;

$R_{18}$ and $R_{19}$, independently from each other, are hydrogen, halogen, nitro, cyano, hydroxy, CHO, $C_1$-$C_6$alkyl, $C_2$-$C_6$alkenyl, $C_2$-$C_6$alkynyl, $C_1$-$C_6$alkoxy, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkylsulfonyl, $C_1$-$C_4$alkylsulfonyl-$C_1$-$C_4$alkyl, $C_1$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, —CONHSO$_2$—$C_1$-$C_6$-alkyl, —CONHSO$_2$N($C_1$-$C_6$-alkyl)$_2$, or are a three- to ten-membered, monocyclic or fused bicyclic ring system which may be aromatic, partially saturated or fully saturated, said three- to ten-membered, monocyclic or fused bicyclic ring system can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_1$-$C_4$alkylcarbonyl, $C_2$-$C_6$alkoxycarbonyl, $C_2$-$C_6$alkylaminocarbonyl, and $C_2$-$C_8$ dialkylaminocarbonyl;

$Z_1$ is oxygen, NOR$_{20}$, NR$_{21}$, N—NR$_{22}$R$_{23}$, or N—N(R$_{24}$)SO$_2$(R$_{25}$), $R_{20}$, $R_{21}$, $R_{22}$ and $R_{25}$ independently from each other, are hydrogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkyl-$C_3$-$C_6$cycloalkylamino, $C_1$-$C_4$alkylcarbonyl, $C_1$-$C_6$alkoxycarbonyl, $C_1$-$C_6$alkylaminocarbonyl, $C_3$-$C_6$dialkylaminocarbonyl, —CONHSO$_2$—$C_1$-$C_6$-alkyl, —CONHSO$_2$N($C_1$-$C_6$-alkyl)$_2$ or are a five- to ten-membered monocyclic or fused bicyclic ring system which may be aromatic, saturated or partially saturated and may contain 1 to 4 heteroatoms selected from the group consisting of nitrogen, oxygen and sulfur, where the ring system is attached directly or via a $C_1$-$C_4$alkylene, $C_2$-$C_4$alkenyl-$C_1$-$C_4$alkylene, $C_2$-$C_4$alkynyl-$C_1$-$C_4$alkylene, —NH—$C_1$-$C_4$alkylene, —N($C_1$-$C_4$alkyl)$C_1$-$C_4$alkylene, SO—$C_1$-$C_4$alkylene, SO—$C_1$-$C_4$alkylene, —SO$_2$—$C_1$-$C_4$alkylene or O—$C_1$-$C_4$alkylene group to the heteroatom substituent, and where each ring system may not contain more than two oxygen atoms and not more than two sulfur atoms and the ring system for its part may be mono-, di- or trisubstituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, hydroxyl, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, halogen, cyano, nitro, phenyl and benzylthio, said phenyl and benzylthio can be mono- or polysubstituted on the phenyl ring by substituents selected from the group consisting of $C_1$-$C_3$alkyl, $C_1$-$C_3$haloalkyl, $C_1$-$C_3$alkoxy, $C_1$-$C_3$haloalkoxy, halogen, cyano and nitro, and where the substituents on the nitrogen in the heterocyclic ring are different from halogen;

$R_{23}$ and $R_{24}$ are hydrogen or $C_1$-$C_3$alkyl;

Q is a ring system $Q_1$

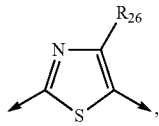
(Q$_1$)

wherein $R_{26}$ is hydrogen, halogen, $C_1$-$C_3$alkyl, $C_1$-$C_3$haloalkyl or is a three- to four-membered ring which can be partially saturated or fully saturated and can contain one heteroatom selected form the group consisting of nitrogen, oxygen and sulphur; said three- to four-membered ring system can be mono- to polysubstituted by substituents independently selected from the group consisting of halogen, methyl and trifluoromethyl; or
- $R_{26}$ is $C_2$-$C_6$alkenyl which can be mono- to polysubstituted by substituents independently selected from the group consisting of halogen, methyl and trifluoromethyl; or
- $R_{26}$ is $C_2$-$C_6$alkynyl which can be substituted by substituents selected from the group consisting of halogen, methyl and $C_1$-$C_2$haloalkyl;
- $m_1$ is 0 or 1; and
- $n_1$ and $n_2$, independently from each other, are 0, 1 or 2; and agrochemically acceptable salts, enantiomers, tautomers and N-oxides of those compounds.

2. A compound of formula I according to claim 1, wherein
$X_1$ is CH or C—F;
$A_1$ is oxygen, S(O)$n_1$, C=O, NR$_5$, CR$_6$R$_7$, —CR$_5$CR$_9$— or a direct bond;
$A_2$ is CR$_{11}$R$_{12}$; and
$A_3$ is CR$_{14}$R$_{15}$ or —CR$_{16}$CR$_{17}$— and
$R_{26}$ is hydrogen, halogen or $C_1$-$C_3$alkyl.

3. A compound of formula I according to claim 1, wherein
$X_1$ is CH or C—F;
$G_1$ is CR$_2$;
$G_2$ is CR$_3$; or
$G_1$-$G_2$ together is —S—, —O—;
$A_1$ is oxygen, S(O)$n_1$, C=O, NR$_5$, CR$_6$R$_7$, —CR$_5$CR$_9$— or a direct bond;
$A_2$ is CR$_{11}$R$_{12}$;
$A_3$ is CR$_{14}$R$_{15}$ or —CR$_{16}$CR$_{17}$—; and
$R_{26}$ is hydrogen, halogen or $C_1$-$C_3$alkyl.

4. A compound of formula I according to claim 1, wherein
$X_1$ is CH;
$G_1$ is CH;
$G_2$ is CH; or
$G_1$-$G_2$ together is —S—;
$A_1$ is oxygen, S(O)$n_1$, C=O, NR$_5$, CR$_6$R$_7$, —CR$_5$CR$_9$— or a direct bond;
$A_2$ is CR$_{11}$R$_{12}$;
$A_3$ is CR$_{14}$R$_{15}$ or —CR$_{16}$CR$_{17}$—; and
$R_{26}$ is hydrogen, halogen or $C_1$-$C_3$alkyl.

5. A compound of formula I according to claim 1, wherein
$X_1$ is CH;
$G_1$ is CH;
$G_2$ is CH; or
$G_1$-$G_2$ together is —S—;
$A_1$ is oxygen, S(O)$n_1$, C=O, NR$_5$, CR$_6$R$_7$, —CR$_5$CR$_9$— or a direct bond;

$A_2$ is CR$_{11}$R$_{12}$;
$A_3$ is CR$_{14}$R$_{15}$ or —CR$_{16}$CR$_{17}$—;
$R_{26}$ is hydrogen, halogen or $C_1$-$C_3$alkyl; and
$Z_1$ is NOR$_{20}$, N—NR$_{22}$R$_{23}$, or N—N(R$_{24}$)SO$_2$(R$_{25}$).

6. A compound of formula I according to claim 1, wherein
$X_1$ is CH;
$G_1$ is CH;
$G_2$ is CH; or
$G_1$-$G_2$ together is —S—;
$A_1$ is oxygen, S(O)$n_1$, C=O, NR$_5$, CR$_6$R$_7$, —CR$_8$CR$_9$— or a direct bond;
$A_2$ is CH$_2$;
$A_3$ is CH$_2$ or —CH$_2$CH$_2$—;
$R_{26}$ is hydrogen, halogen, $C_1$-$C_3$alkyl; and
$Z_1$ is NOR$_{20}$, N—NR$_{22}$R$_{23}$, or N—N(R$_{24}$)SO$_2$(R$_{25}$).

7. A compound of formula I according to claim 1, wherein
$X_1$ is CH;
$G_1$ is CH;
$G_2$ is CH;
$A_1$ is oxygen, S(O)$n_1$, C=O, NR$_5$, CH$_2$, —CH$_2$CH$_2$— or a direct bond;
$A_2$ is CH$_2$;
$A_3$ is CH$_2$ or —CH$_2$CH$_2$—;
$R_{26}$ is hydrogen, halogen or $C_1$-$C_3$alkyl; and
$Z_1$ is NOR$_{20}$, N—NR$_{22}$R$_{23}$, or N—N(R$_{24}$)SO$_2$(R$_{25}$).

8. A compound of formula I according to claim 1, wherein
$X_1$ is CH;
$G_1$ is CH;
$G_2$ is CH; or
$G_1$-$G_2$ together is —S—;
$A_1$ is oxygen, S(O)$n_1$, C=O, NR$_5$, CH$_2$, —CH$_2$CH$_2$— or a direct bond;
$A_2$ is CH$_2$;
$A_3$ is CH$_2$;
$R_{26}$ is hydrogen, halogen, $C_1$-$C_3$alkyl; and
$Z_1$ is NOR$_{20}$.

9. A compound of formula I according to claim 1, wherein
$X_1$ is CH;
$G_1$ is CH;
$G_2$ is CH;
$A_1$ is oxygen, S(O)$n_1$, NR$_5$, CH$_2$ or a direct bond;
$A_2$ is CH$_2$;
$A_3$ is CH$_2$;
$R_{24}$ is hydrogen, halogen or $C_1$-$C_3$alkyl; and
$Z_1$ is NOR$_{20}$, N—NR$_{22}$R$_{23}$, or N—N(R$_{24}$)SO$_2$(R$_{25}$).

10. A pesticidal composition, which comprises at least one compound of formula I according to claim 1 or, where appropriate, a tautomer thereof, in each case in free form or in agrochemically utilizable salt form, as active ingredient and at least one auxiliary.

11. A method for controlling pests, which comprises applying a composition according to claim 5 to the pests or their environment with the exception of a method for treatment of the human or animal body by surgery or therapy and diagnostic methods practiced on the human or animal body.

12. A method for the protection of plant propagation material from the attack by pests, which comprises treating the propagation material or the site, where the propagation material is planted, with a composition according to claim 10.

13. Plant propagation material treated in accordance with the method described in claim 12.

* * * * *